United States Patent
Schwartz et al.

(10) Patent No.: US 10,233,205 B2
(45) Date of Patent: Mar. 19, 2019

(54) MAGNETIC RESONANCE IMAGING CONTRAST AGENT CAPABLE OF DETECTING HYDROGEN PEROXIDE AND REDUCING REACTIVE OXYGEN SPECIES

(71) Applicant: Auburn University, Auburn, AL (US)

(72) Inventors: Dean D. Schwartz, Auburn, AL (US); Christian R. Goldsmith, Auburn, AL (US); Ronald J. Beyers, Auburn, AL (US); Meng Yu, Auburn, AL (US)

(73) Assignee: Auburn University, Auburn, AL (US)

( * ) Notice: Subject to any disclaimer, the term of this patent is extended or adjusted under 35 U.S.C. 154(b) by 178 days.

(21) Appl. No.: 15/230,030

(22) Filed: Aug. 5, 2016

(65) Prior Publication Data

US 2017/0057986 A1     Mar. 2, 2017

Related U.S. Application Data

(60) Provisional application No. 62/202,556, filed on Aug. 7, 2015.

(51) Int. Cl.
*A61K 49/00* (2006.01)
*C07F 13/00* (2006.01)
*A61K 49/10* (2006.01)

(52) U.S. Cl.
CPC ............ *C07F 13/00* (2013.01); *A61K 49/103* (2013.01)

(58) Field of Classification Search
CPC ................................ A61K 49/00; A61K 49/10
See application file for complete search history.

(56) References Cited

U.S. PATENT DOCUMENTS

| | | | |
|---|---|---|---|
| 5,716,598 | A | 2/1998 | Golman et al. |
| 5,980,863 | A | 11/1999 | Harnish et al. |
| 6,165,963 | A | 12/2000 | Delroisse et al. |
| 2004/0067201 | A1 | 4/2004 | Perkins et al. |
| 2015/0005259 | A1 | 1/2015 | Karlsson et al. |

FOREIGN PATENT DOCUMENTS

| | | |
|---|---|---|
| WO | 98/22148 A1 | 5/1998 |
| WO | 2010/026545 A1 | 3/2010 |
| WO | 2014/107722 A1 | 7/2014 |

OTHER PUBLICATIONS

Christan Goldsmith et al., A Mopnonuclear Manganese (II) Complex Demonstrates a Strategy to Simultaneously Image and Treat Oxidative Stress, J. am. Chem. Soc., 2014, 136, 12836-12839. (Year: 2014).*
Meng Yu et al. A Magnetic Resonance Imaging Contrast Agent Capable of Detecting Hydrogen Peroxide, InOrg. Chem, 51, 9153-9155. (Year: 2012).*
Tu, Chuqiao, et al. "Multimodal Magnetic-Resonance/Optical-Imaging Contrast Agent Sensitive to NADH", Angew Chem Int. Ed Engl. (2009); 48(35): 6547-6551.
Liu, Guanshu, et al. "Design and Characterization of a New Irreversible Responsive PARACEST MRI Contrast Agent that Detects Nitric Oxide", Magnetic Resonance in Medicine (2007) 58: 1249-1256.
Song, Bo, et al. "A europium (iii)-based PARACEST agent for sensing singlet oxygen by MRIt", The Royal Society of Chemistry, (2013), 42: 8066-8069.
Mialane, Pierre, et al. "Structures of Fe(II) Complexes with N,N,N'-Tris(2-pyridylmethyl)ethane-1,2-diamine Type Ligands. Bleomycin-like DNA Cleavage and Enhancement by an Alkylammonium Substituent on the N' Atom of the Ligand", Inorg. Chem (1999), 38: 1085-1092.
Yu, Meng, et al. "A Magnetic Resonance Imaging Contrast Agent Capable of Detecting Hydrogen Peroxide" Inorganic Chemistry (2012), 51: 9153-9155.
Yu, Meng, et al. "A Mononuclear Manganese (II) complex Demonstrates a Strategy to Simultaneously Image and Treat Oxidative Stress", Journal Am. Chem. Soc. (2014) 136: 12836-12839.
Loving, Galen S., et al. "Redox-Activated Manganese-Based MR Contrast Agent", Journal Am. Chem. Soc. (2013) 135:4620-4623.

* cited by examiner

*Primary Examiner* — Michael G. Hartley
*Assistant Examiner* — Jagadishwar R Samala
(74) *Attorney, Agent, or Firm* — McKee, Voorhees & Sease, PLC

(57) ABSTRACT

The current invention provides metal ion complexes with an organic ligand, compositions comprising such complexes. In particular, these complexes are capable of reacting with a reactive oxygen species in a subject and increase their $T_1$-weighted relaxivities so a clinical MRI scanner can detect an oxidative stress hotspot in the subject. The disclosed complexes also exhibit excellent anti-oxidant properties and low cell toxicity, therefore can be used as a therapeutic agent to relieve oxidative stress in the subject, or as both a MRI contrast agent and therapeutic agent in a composition.

20 Claims, 28 Drawing Sheets

MAGNETIC RESONANCE IMAGING CONTRAST AGENT CAPABLE OF DETECTING HYDROGEN PEROXIDE AND REDUCING REACTIVE OXYGEN SPECIES

CROSS-REFERENCE TO RELATED APPLICATIONS

This application is a nonprovisional application of U.S. Provisional Application No. 62/202,556, filed Aug. 7, 2015, titled "Coordination Complexes Capable of Simultaneously Imaging and Treating Oxidative Stress," which is herein incorporated by reference in its entirety.

FIELD OF THE INVENTION

The invention relates to metal complexes with an organic ligand, magnetic resonance imaging contrast agents, MRI methods, and pharmaceutical compositions that can be used to detect an oxidant in a subject and reduce it at the same time. In particular, the invention is related to metal complexes that have an organic ligand containing one or more oxidizable groups, increase their $T_1$-weighted relaxivities upon the ligand's oxidation, and function as both MRI contrast agents for detecting an oxidant and potent antioxidants.

BACKGROUND OF THE INVENTION

The over-production of reactive oxygen species (ROSs), such as $H_2O_2$, $O_2^-$, and hydroxyl radicals, has been associated with several lethal and debilitating health conditions. Heightened oxidative damage to proteins and other biomolecules has been observed in the biopsies and post-mortem examinations of patients suffering from a wide variety of cardiovascular and neurological diseases. Understanding the roles that ROSs play in the progressions of these and other conditions requires probes that can monitor their production and traffic within biological systems. Currently, most sensors capable of directly detecting ROSs rely on either fluorescent or luminescent outputs. Although these probes provide high spatial resolution, the short wavelengths of light needed to excite the reporter make imaging activity in samples other than thin tissues and cell cultures difficult.

Magnetic resonance imaging (MRI), conversely, uses radio-frequency photons to excite the hydrogen nuclei in water molecules and can be used to visualize tissues and organs deep within thicker biological samples. Therefore, magnetic resonance imaging (MRI) is commonly used as a non-invasive diagnostic tool in medicine. Since the bulk of the body's $^1H$ nuclei are from water molecules, MRI often differentiates tissues on the basis of their water content. Contrast agents are often added to accelerate the relaxation of the excited $^1H$ nuclei back to the ground state; this increases the amount of RF radiation that can be absorbed, thereby enhancing the contrast between water-rich and water-deficient regions. Either spin-lattice ($T_1$) or spin-spin ($T_2$) relaxation times can be monitored, but small molecule contrast agents generally induce larger changes in $T_1$. The use of a responsive contrast agent, which exhibits a different relaxivity ($r_1$) upon exposure to an analyte, can allow researchers to visualize a biochemical process within a whole-body subject in concert with clinically approved MRI instrumentation.

Most small molecule MRI contrast agents shorten the longitudinal relaxation times ($T_1$) of excited protons, allowing sharper contrast between regions with high and low water contents. The ability to accelerate these relaxations defines the $T_1$-weighted relaxivity ($r_1$) of the contrast agent. A molecule that displays a different $r_1$ value upon the addition of an analyte can serve as a sensor when monitored by MRI.

Several such MRI contrast agent sensors have been developed, but few have been directed towards imaging oxidative activity. The probes capable of detecting oxidants often either require a co-analyte or display a similar response to $O_2$ or another analyte. Most redox-responsive contrast agent probes with mononuclear metal centers function via changes in the oxidation state of the metal, with the more paramagnetic species having the greater $r_1$. Caravan and co-workers, for instance, reported a series of manganese-containing contrast agents capable of switching between the +2 and +3 oxidation states through reactions with glutathione and $H_2O_2$. (Loving, G. S.; Mukherjee, S.; Caravan, P. J. Am. Chem. Soc. 2013, 135, 4620-4623.) Morrow's group recently reported an oxygen-sensitive cobalt complex that toggles between paramagnetic +2 and diamagnetic +3 oxidation states; it should be noted that this contrast agent operates through a PARACEST mechanism, rather than changes in $T_1$. (Tsitovich, P. B.; Spernyak, J. A.; Morrow, J. R. Angew. Chem. Int. Ed. 2013, 52, 13997-14000.)

An alternative strategy is to couple the change in the MRI properties to a change in the oxidation state of the ligand, rather than the metal. The research groups of Sherry, Louie, and Pagel used this approach to develop lanthanide complexes that activate either upon reduction by β-NADH or ascorbic acid or upon oxidation by mixtures of NO and $O_2$ or singlet oxygen. (Ratnakar, S. J.; Viswanathan, S.; Kovacs, Z.; Jindal, A. K.; Green, K. N.; Sherry, A. D. J. Am. Chem. Soc. 2012, 134, 5798-5800; Tu, C.; Nagao, R.; Louie, A. Y. Angew. Chem. Int. Ed. 2009, 48, 6547-6551; Liu, G.; Li, Y.; Pagel, M. D. Magn. Reson. Med. 2007, 58, 1249-1256; Song, B.; Wu, Y; Yu, M.; Zhao, P.; Zhou, C.; Kiefer, G. E.; Sherry, A. D. Dalton Trans. 2013, 42, 8066-8069.)

Recently, a mononuclear manganese complex capable of directly detecting $H_2O_2$; notably, the complex lacks a chemical response to $O_2$ was reported. (Yu, M.; Beyers, R. J.; Gorden, J. D.; Cross, J. N.; Goldsmith, C. R. Inorg. Chem. 2012, 51, 9153-9155.) However, upon oxidation, the mononuclear complexes irreversibly couple into binuclear Mn(II) species. The reaction with $H_2O_2$ decreases the $T_1$-weighted relaxivity per manganese ion; that the response is a reduction in contrast enhancement limits the probe's ability to resolve different levels of $H_2O_2$. Needless to say, a better MRI contrast agent for detecting $H_2O_2$ or other oxidants is desired.

The objective of this invention is to develop metal complexes with ligands that are redox-responsive to oxidants, preferably reactive oxygen species.

The other objective of this invention is to develop a MRI contrast agent that is not only capable of directly detecting a reactive oxygen species, but also lacks a chemical response to $O_2$ and displays an increase in its $T_1$-weighted relaxivity upon the ligand's oxidation.

Another objective of this invention is to develop a pharmaceutical agent that is capable of being both a MRI contrast agent and a therapeutic agent for reducing reactive oxygen species in a subject, such as in a mammal or human.

Other objects, advantages, and features of the present invention will become apparent from the following specification taken in conjunction with the accompanying examples, figures, and drawings.

BRIEF SUMMARY OF THE INVENTION

An advantage of the present invention is that the disclosed metal complexes are responsive to a reactive oxygen species in a novel mechanism. Upon oxidation, the metal ion of the complexes does not change its oxidation state, instead the ligand is oxidized. More importantly, the $T_1$-weighted relaxivities of the disclosed complexes increase upon oxidation, providing a signal that can be detected and quantified by magnetic resonance imaging.

Serendipitously, the disclosed metal complexes not only respond to biologically relevant oxidants with increases in their respective relaxivities, providing a signal for MRI imaging, but also exhibit good antioxidant properties and low cytotoxicities. Therefore, the disclosed complexes can serve as potent antioxidants to alleviate oxidative stress in a subject. Alternately, the disclosed metal complex can be used in a composition that can function as a MRI contrast agent for detecting a reactive oxygen species (ROS) hotspot through MRI imaging and as a therapeutic agent to alleviate oxidative stress caused by aberrantly high concentrations of ROSs in a subject.

In one aspect, the present invention is a composition comprising a complex of a metal ion M with a ligand A, or a salt thereof, wherein the complex has a generic formula,

wherein M is $Mn^{2+}$, $Ni^{2+}$, $Co^{2+}$, $Fe^{2+}$, or a combination thereof, B is acetonitrile, methanol, $Cl^-$, $Br^-$, $I^-$, ethanol, water, perchlorate, triflate, a small inorganic or organic molecule or ion, or a combination thereof;

A is a ligand of formula II

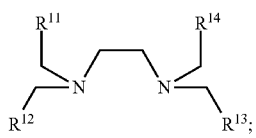

x is an integer between 6 and −6, wherein $R^{11}$, $R^{12}$, $R^{13}$, and $R^{14}$ are independently a substituted or unsubstituted pyridinyl, pyrazinyl, pyrimidinyl, pyridazinyl, 1,2,3-triazinyl, 1,2,4-trazinyl, 1,3,5-triazinyl, quinolyl, phenolyl group, or an isomer thereof and at least one of $R^{11}$, $R^{12}$, $R^{13}$, and $R^{14}$ is a substituted or unsubstituted quinolyl group.

In yet another aspect, the present invention is a magnetic resonance imaging (MRI) contrast agent composition comprising such a complex. In other words, such a complex is a reactive oxygen species sensor (ROS) by MRI scanner for a subject.

In yet another aspect, the present invention is a method of detecting a reactive oxygen species hotspot in a subject using a MRI contrast agent composition. The MRI contrast agent composition used in the method may be one comprising such a complex.

In another aspect, the present invention is a pharmaceutical composition comprising an effective amount of such a complex, a stereoisomer thereof, a tautomer thereof, a tautomer of the stereoisomer, a pharmaceutically acceptable salt of any of the foregoing.

In yet another aspect, the present invention is a method of treatment comprising administering to a subject having oxidative stress such a pharmaceutical composition.

In another aspect, the present invention is method of detecting high localized concentrations of reactive oxygen species within a subject and alleviating the oxidative stress thereof at the same time, comprising administering to a subject a therapeutically and magnetic resonance imaging effective amount of such a composition.

While multiple embodiments are disclosed, still other embodiments of the present invention will become apparent to those skilled in the art from the following detailed description, which shows and describes illustrative embodiments of the invention. Accordingly, the examples, figures, drawings, and detailed description are to be regarded as illustrative in nature and not restrictive.

Figure 1:
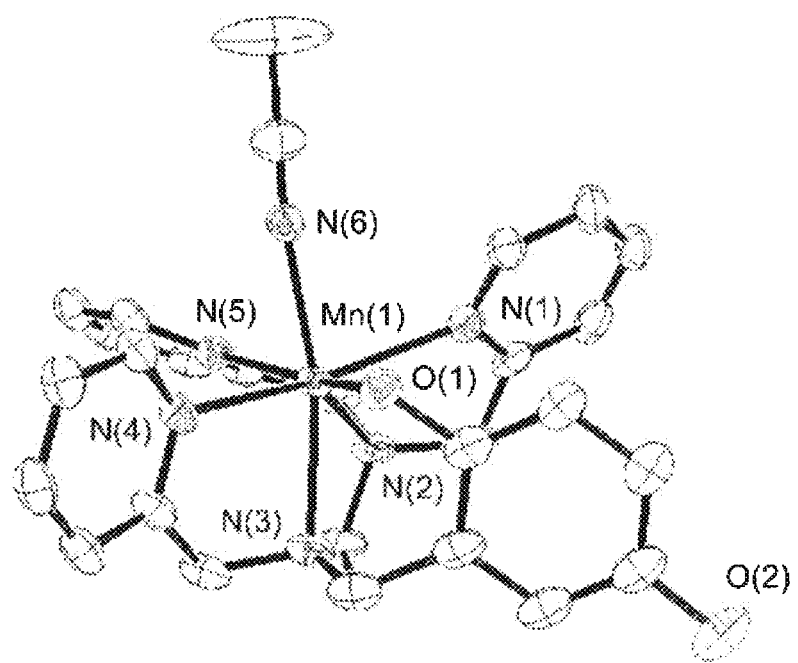
FIG. 1. Structure of $[Mn(H_2qtp1)(MeCN)]^{2+}$.

Various embodiments of the present invention will be described in detail with reference to the examples, figures, and drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The present invention is related to novel metal complexes that respond to $H_2O_2$ or other reactive oxygen species (ROS) with an altogether different molecular mechanism. The disclosed metal complexes do not change the metal ion's oxidation state after the reaction with $H_2O_2$ or other ROSs. Instead, in these novel metal complexes, the oxidation is directed to the organic ligand portion. This differs from a complex in the prior art, in which the manganese reporter toggles between the +2 and +3 oxidation states, depending on the local redox environment. Due to the lessened paramagnetism associated with the +3 oxidation state, this prior art sensor has a turn-off response to biologically relevant oxidants.

Also, oxidation of the disclosed complexes results in an increase in their respective $T_1$-weighted relaxivity, allowing MRI detection. This property of the disclosed complexes also differ from one of a similar complex in the prior art, which reduces its $T_1$-weighted relaxivity upon oxidation.

The present invention is also related to novel MRI contrast agents that respond to $H_2O_2$ or other reactive oxygen species (ROS) with an altogether different molecular mechanism. The disclosed metal complexes do not change the metal ion's oxidation state and increase their respective $T_1$-weighted relaxivity after the reaction with $H_2O_2$ or other ROSs.

The present invention is also related to a MRI method that can detect localized high concentrations of reactive oxygen species within a subject. The method uses a contrast agent comprising a metal complex with an organic ligand. The metal complex does not change its oxidation state, instead the organic ligand is oxidized by ROSs. In addition, the ligand's oxidation is reversible and the complex's $T_1$-weighted relaxivity increases upon oxidation. More importantly, the metal complexes have low toxicity.

The present invention is also related to pharmaceutical compositions that contains the disclosed metal complexes. These disclosed metal complexes have a good antioxidant and cytotoxicity properties as well. The pharmaceutical compositions therefore can be tolerated in high doses and function both as MRI contrast agent to locate hotspots of oxidative activity and as therapeutic agents to alleviate oxidative stress at the same time.

The disclosed metal complexes, contrast agents, MRI methods, and pharmaceutical compositions are related to a metal complex with an oxidizable organic ligand. The existence of an oxidizable group in the ligand part of the complexes enable a fundamentally different chemical response of the complex to oxidants. One such metal complex comprises a $Mn^{2+}$ and a ligand containing a quinolyl group, which is oxidized to a more weakly metal-coordinating para-quinone upon exposure to a ROS, such as $H_2O_2$, instead of oxidatively coupling to other groups in the ligand as in the prior art. Although manganese was not previously known to catalyze quinol oxidation, other redox-active transition metal ions have been reported to do so. The metal ion in the disclosed metal complexes therefore serves as both the paramagnetic reporter for the metal complexes and the catalyst for the oxidation of the ligand.

The embodiments of this invention are not limited to particular compositions and methods of use, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "independently" means that where more than one substituent is selected from a number of possible substituents, those substituents may be the same or different.

As used herein, "substituted" refers to an organic group as defined below (i.e., an alkyl group) in which one or more bonds to a hydrogen atom contained therein are replaced by a bond to non-hydrogen or non-carbon atoms. Substituted groups also include groups in which one or more bonds to carbon(s) or hydrogen(s) atom replaced by one or more bonds, including double or triple bonds, to a heteroatom. Thus, a substituted group is substituted with one or more substituents, unless otherwise specified. A substituted group can be substituted with 1, 2, 3, 4, 5, or 6 substituents.

Substituted ring groups include rings and ring systems in which a bond to a hydrogen atom is replaced with a bond to a carbon atom. Therefore, substituted cycloalkyl, aryl, heterocyclyl, and heteroaryl groups may also be substituted with substituted or unsubstituted alkyl, alkenyl, and alkynyl groups are defined herein.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Alkenyl groups or alkenes are straight chain, branched, or cyclic alkyl groups having two to about 30 carbon atoms, and further including at least one double bond. In some embodiments alkenyl groups have from 2 to about 20 carbon, or typically, from 2 to 10 carbon atoms. Alkenyl groups may be substituted or unsubstituted. Alkenyl groups may be substituted similarly to alkyl groups.

As used herein, the terms "alkylene", cycloalkylene", alkynylene, and alkenylene", alone or as part of another substituent, refer to a divalent radical derived from an alkyl, cycloalkyl, or alkenyl group, respectively, as exemplified by —$CH_2CH_2CH_2$—. For alkylene, cycloalkylene, alkynylene, and alkenylene groups, no orientation of the linking group is implied.

As used herein, "aryl" or "aromatic" groups are cyclic aromatic hydrocarbons that do not contains heteroatoms. Aryl groups include monocyclic, bicyclic, and polycyclic ring systems. Thus, aryl groups include, but are not limited to, phenyl, azulenyl, heptalenyl, biphenylenyl, indacenyl, florenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, in others from 6 to 12 or 6-10 carbon atoms in the ring portions of the groups. The phrase "aryl groups" includes groups containing fused rings, such as fused aromatic-aliphatic ring systems. Aryl groups may substituted or unsubstituted.

A heterocyclic group is a cyclic group having, as ring members, atoms of at least two different elements, which cyclic group may be saturated, partially unsaturated (non-aromatic) or fully unsaturated (aromatic). The terms "heterocyclic" or "heterocyclyl" includes heterocycloalkyl and heteroaryl groups. It is to be understood that the terms heterocyclic, heterocyclyl, heteroaryl, and heterocycloalkyl, are intended to encompass stable groups where a ring nitrogen heteroatom is optionally oxidized (e.g., heteroaryl groups containing an N-oxide, such as oxo-pyridyl (pyridyl-N-oxide) and oxo-oxadiazolyl (oxo-4,5-dihydro-1,3,4-oxadiazolyl) or where a ring sulfur heteroatom is optionally oxidized (e.g., heterocycloalkyl groups containing sulfones or sulfoxide moieties, such as tetrahydrothienyl-1-oxide (tetrahydrothienyl sulfoxide, tetrahydrothiophenyl sulfoxide) and tetrahydrothienyl-1,1-dioxide (tetrahydrothienyl sulfone)).

"Heterocycloalkyl" refers to a non-aromatic, monocyclic or bicyclic group containing 3-10 ring atoms, being saturated or having one or more degrees of unsaturation and containing one or more (generally one or two) heteroatom substitutions independently selected from oxygen, sulfur, and nitrogen. Examples of "heterocycloalkyl" groups include, but are not limited to, aziridinyl, thiiranyl, oxiranyl, azetidinyl, oxetanyl, thietanyl, pyrrolidinyl, pyrrolinyl, pyrazolidinyl, pyrazolinyl, imidazolidinyl, imidazolinyl, oxazolinyl, thiazolinyl, tetrahydrofuranyl, dihydrofuranyl, tetrahydrothienyl, 1,3-dioxolanyl, piperidinyl, piperazinyl, tetrahydropyranyl, dihydropyranyl, tetrahydrothiopyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, 1,4-dithianyl, morpholinyl, thiomorpholinyl, hexahydro-1H-1,4-diazepinyl, azabicylo[3.2.1]octyl, azabicylo[3.3.1]nonyl, azabicylo[4.3.0]nonyl, oxabicylo[2.2.1]heptyl, 1,1-dioxido-tetrahydro-2H-thiopyranyl, and 1,5,9-triazacyclododecyl.

Examples of "4-membered heterocycloalkyl" groups include oxetanyl, thietanyl and azetidinyl.

The term "5-6-membered heterocycloalkyl" represents a non-aromatic, monocyclic group, which is saturated or partially unsaturated, containing 5 or 6 ring atoms, which includes one or two heteroatoms selected independently from oxygen, sulfur, and nitrogen. Illustrative examples of 5 to 6-membered heterocycloalkyl groups include, but are not limited to pyrrolidinyl, piperidinyl, piperazinyl, tetrahydrofuranyl, tetrahydrothienyl, tetrahydropyranyl, tetrahydrothiopyranyl, morpholinyl, and thiomorpholinyl.

"Heteroaryl" represents a group or moiety comprising an aromatic monocyclic or bicyclic radical, containing 5 to 10 ring atoms, including 1 to 4 heteroatoms independently selected from nitrogen, oxygen and sulfur. This term also encompasses bicyclic heterocyclic-aryl groups containing either an aryl ring moiety fused to a heterocycloalkyl ring moiety or a heteroaryl ring moiety fused to a cycloalkyl ring moiety.

Illustrative examples of heteroaryls include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl (pyridyl), oxopyridyl (pyridyl-N-oxide), pyridazinyl, pyrazinyl, pyrimidinyl, triazinyl, benzofuranyl, isobenzofuryl, 2,3-dihydrobenzofuryl, 1,3-benzodioxolyl, dihydrobenzodioxinyl, benzothienyl, indolizinyl, indolyl, isoindolyl, dihydroindolyl, benzimidazolyl, dihydrobenzimidazolyl, benzoxazolyl, dihydrobenzoxazolyl, benzothiazolyl, benzoisothiazolyl, dihydrobenzoisothiazolyl, indazolyl, imidazopyridinyl, pyrazolopyridinyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

As used herein, "5-6-membered heteroaryl" represents an aromatic monocyclic group containing 5 or 6 ring atoms, including at least one carbon atom and 1 to 4 heteroatoms independently selected from nitrogen, oxygen and sulfur. Selected 5-membered heteroaryl groups contain one nitrogen, oxygen, or sulfur ring heteroatom, and optionally contain 1, 2, or 3 additional nitrogen ring atoms. Selected 6-membered heteroaryl groups contain 1, 2, or 3 nitrogen ring heteroatoms. Examples of 5-membered heteroaryl groups include furyl (furanyl), thienyl, pyrrolyl, imidazolyl, pyrazolyl, triazolyl, tetrazolyl, thiazolyl, isothiazolyl, thiadiazolyl, oxazolyl, isoxazolyl, oxadiazolyl and oxo-oxadiazolyl. Selected 6-membered heteroaryl groups include pyridinyl, oxo-pyridyl, pyrazinyl, pyrimidinyl, pyridazinyl and triazinyl.

Bicyclic heteroaryl groups include 6,5-fused heteroaryl (9-membered heteroaryl) and 6,6-fused heteroaryl (10-membered heteroaryl) groups. Examples of 6,5-fused heteroaryl (9-membered heteroaryl) groups include benzothienyl, benzofuranyl, indolyl, indolinyl, isoindolyl, isoindolinyl, indazolyl, indolizinyl, isobenzofuryl, 2,3-dihydrobenzofuryl, benzoxazolyl, benzthiazolyl, benzimidazolyl, benzoxadiazolyl, benzthiadiazolyl, benzotriazolyl, 1,3-benzoxathiol-2-on-yl (2-oxo-1,3-benzoxathiolyl), purinyl and imidazopyridinyl.

Examples of 6,6-fused heteroaryl (10-membered heteroaryl) groups include quinolyl, isoquinolyl, phthalazinyl, naphthridinyl (1,5-naphthyridinyl, 1,6-naphthyridinyl, 1,7-naphthyridinyl, 1,8-naphthyridinyl), quinazolinyl, quinoxalinyl, 4H-quinolizinyl, tetrahydroquinolinyl, cinnolinyl, and pteridinyl.

Unless otherwise specified, all bicyclic ring systems may be attached at any suitable position on either ring.

The terms "halogen" and "halo" represent chloro, fluoro, bromo, or iodo substituents. "Oxo" represents a double-bonded oxygen moiety; for example, if attached directly to a carbon atom forms a carbonyl moiety (C=O). "Hydroxy" or "hydroxyl" is intended to mean the radical —OH. As used herein, the term "cyano" refers to the group —CN.

As used herein, the term "optionally substituted" indicates that a group (such as an alkyl, cycloalkyl, alkoxy, heterocycloalkyl, aryl, or heteroaryl group) or ring or moiety (such as a carbocyclic or heterocyclic ring or moiety) may be unsubstituted, or the group, ring or moiety may be substituted with one or more substituent(s) as defined. In the case where groups may be selected from a number of alternative groups, the selected groups may be the same or different.

As used here, "denticity" refers to the number of donor groups in a single ligand that bind to a central atom in a coordination complex, such as ones disclosed here. In many cases, only one atom in the ligand binds to the metal, so the denticity equals one, and the ligand is said to be monodentate (sometimes called unidentate). Ligands with two bonded atoms are called bidentate (sometimes called didentate). Ligands with more than one bonded atoms are called polydentate or multidentate.

As used herein, the term "substantially free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

Composition Comprising a Metal Complex

In one aspect, the present invention is a composition comprising a complex of a metal ion M with a ligand A, or salt thereof, wherein the complex has a generic formula, $$[M(A)(B)]^x$$

wherein M is $Mn^{2+}$, $Ni^{2+}$, $Co^{2+}$, $Fe^{2+}$, or a combination thereof;

B is absent, acetonitrile, methanol, $Cl^-$, $Br^-$, $I^-$, ethanol, water, perchlorate, triflate, a small inorganic or organic molecule or ion, monodentate, bidentate, or a combination thereof;

A is a ligand of formula II

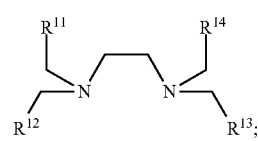

x is an integer between 6 and −6, wherein $R^{11}$, $R^{12}$, $R^{13}$, and $R^{14}$ are independently a substituted or unsubstituted 5-6-membered heteroaryl group and at least one of $R^{11}$, $R^{12}$, $R^{13}$, and $R^{14}$ is a substituted or unsubstituted quinolyl group.

In some embodiments, in the disclosed metal complexes, B is absent. In some other embodiments, B is acetonitrile, methanol, $Cl^-$, $Br^-$, $I^-$, ethanol, water, perchlorate, triflate, a small inorganic or organic molecule or ion, monodentate, bidentate, or a combination thereof. A small inorganic or organic molecule or ion as used here means a molecule or ion that is similar to those specified above and contains a heteronuclear atom to provide a lone electron pair to the metal ion M.

In some embodiments, the metal complexes is neutral, i.e., x is 0. In some other embodiments, the metal complexes has a charge of 6, 5, 4, 3, 2, 1, −1, −2, −3, −4, −5, or −6, depending on the charge states of both B and organic ligand A. Preferably, the charge of the metal complexes is between 3 and −3.

In some embodiments, in the disclosed metal complexes, one or more $R^{11}$, $R^{12}$, $R^{13}$, and $R^{14}$ groups independently a substituted or unsubstituted pyridinyl, pyrazinyl, pyrimidinyl, pyridazinyl, 1,2,3-triazinyl, 1,2,4-trazinyl, 1,3,5-triazinyl, quinolyl, phenolyl group, or an isomer thereof and at least one of $R^{11}$, $R^{12}$, $R^{13}$, and $R^{14}$ is a substituted or unsubstituted quinolyl group.

In some embodiments, in the disclosed metal complexes, one or more $R^{11}$, $R^{12}$, $R^{13}$, and $R^{14}$ groups are independently connected to the respective methylene groups in the ligand through a carbon atom. In some other embodiments, one or more $R^{11}$, $R^{12}$, $R^{13}$, and $R^{14}$ groups are independently connected to the respective methylene groups in the ligand through a heteroatom.

A complex in the current invention has a stability constant K, defined as the concentration of the complex divided by the concentrations of each coordinating ligands in an equilibrium solution of the complex. K is usually represented by its log K value (log K=$\log_{10}$ K). The stability constant of a complex can be determined by any method known to one skilled in the art, whether through determining concentrations of both complex and its ligands or competitive or comparison to other compound with a known stability constant.

A complex in the current invention also has one or more ionization states upon losing one or more protons or gaining one or more protons depending on the pH value of the solution. The ability to gain or lose a proton is usually measured by a $pK_a$ or $pK_b$ value, for the ability to lose a proton or gain a proton, respectively, as one skilled in the art would know.

A complex in the current invention also has an ability to be oxidized by another compound or process. A compound's ability to be oxidized or reduced is measured by its redox potential E. This redox potential is usually expressed as a relative potential against a normal hydrogen electrode (NHE).

A metal complex in the current invention may be a neutral compound without any charge or an ion with either position or negative charge, depending on the charge states of M, ligand A, ligand B, or a combination thereof. When the metal complex is a charge species, its charge is balanced by one or more ions with opposite charge(s) as understood by one skilled in the art.

A metal complex in the current invention has a general geometry. A metal ion center may be heptacoordinate, with six donor atoms from the ligand A described below and one from the ligand B. The ligand B may be a small, charge, uncharged, protonated, or deprotonated organic molecule solvent. The ligand B may also be a small charge, uncharged, protonated, deprotonated, monodentate, inorganic molecule, or ion thereof. Alternatively, the metal complex may be hexadentate, with all six donor atoms from the ligand A described below and ligand B being completely absent. Alternatively, the metal complex may be hexadentate, with five donor atoms from the ligand A and two donor atoms from either one or two equivalents of ligand B. In the former case, ligand B would be a bidentate ligand.

A complex of the current invention has a $T_1$-weighted relaxivity value. The relaxivity of a compound reflects how the relaxation rates of a solution change as a function of the metal complex concentration [C]. Since a metal complex may affect the two relaxation rates ($1/T_1$ and $1/T_2$, lattice-spin and spin-spin, respectively) individually, there are two corresponding relaxivities, denoted $r_1$ and $r_2$. By definition $$1/\Delta T_1 = r_1 \cdot [C] \text{ and } 1/\Delta T_2 = r_2 \cdot [C]$$

Since $\Delta T_1$ and $\Delta T_2$ are given in seconds and [C] is measured in millimoles per liter (mM), $r_1$ and $r_2$ have units of $mM^{-1}s^{-1}$.

The relaxation rates of a contrast agent in solution are obtained by graphing changes in relaxation rates ($1/\Delta T_1$) and ($1/\Delta T_2$) at different concentrations. The slopes of the lines represent $r_1$ and $r_2$. Relaxivity depends on the temperature, field strength, and substance in which the contrast agent is dissolved. For contrast agents in clinical use, it is typical to cite $r_1$ and $r_2$ values at 1.5 T in plasma at body temperature (37° C.). The relevant relaxivity value in this disclosure is $T_1$-weighted relaxivity value of a complex.

A reactive oxygen species (ROS) as used here refers to a highly reactive, oxygen-containing molecule, including a free radical. A ROS may be a hydroxyl radical, hydrogen peroxide, superoxide ($O_2^-$), the superoxide anion radical, nitric oxide radical, singlet oxygen, hypochlorite radical, and a lipid peroxide. These ROSs can react with membrane lipids, nucleic acids, proteins and enzymes, and other small molecules.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

The metal complexes disclosed herein can be considered as sensors for a ROS. In this context, a metal complex as a small molecule displays a predictable and significant spectroscopic change in response to an analyte. The spectroscopic change results from a reversible or irreversible reaction between the pre-activated small molecule and the analyte. In the current case, the sensor would be a metal complex with a redox-active ligand. The analyte would be $H_2O_2$, superoxide ($O_2^-$), or other ROS. The spectroscopic response would be the change in $T_1$-weighted relaxivity, which is monitored using a MRI scanner. The reaction that leads to the response would be the oxidation of the ligand to the para-quinone form(s) by the $H_2O_2$, superoxide ($O_2^-$), or other ROS. In other words, metal complexes disclosed herein are ROS sensors for a subject.

In some embodiments, the ligand of the complex in the composition has a following formula

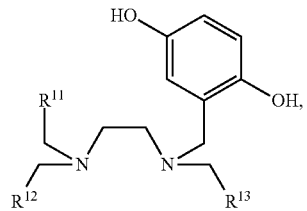

i.e, $R^{14}$ is unsubstituted quinolyl group. In some other embodiments, the $R^{11}$ and $R^{14}$ of the complex are independently a substituted or unsubstituted quinolyl group. In some other embodiments, the $R^{13}$ and $R^{14}$ of the complex are independently a substituted or unsubstituted quinolyl group. In some other embodiments, the ligand of the complex has a following formula

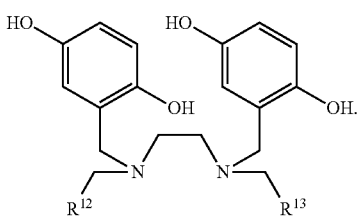

In other embodiments, the ligand has a following formula

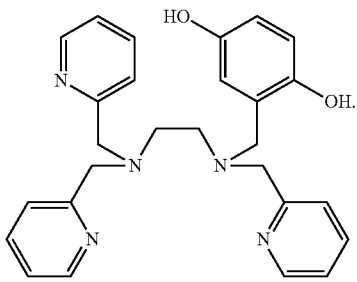 [SMILES: Oc1ccc(O)c(CN(CCN(Cc2ccccn2)Cc2ccccn2)Cc2ccccn2)c1]

In yet other embodiments, the ligand has a following formula

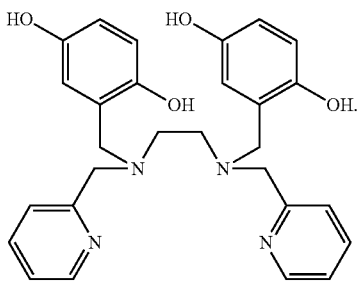 [SMILES: Oc1ccc(O)c(CN(CCN(Cc2ccccn2)Cc2cc(O)ccc2O)Cc2ccccn2)c1]

In some other embodiments, the metal ion of the complex is $Mn^{2+}$.

In some embodiments, the ligand of the complex disclosed in the current invention or composition can be oxidized by a reactive oxygen species. In some embodiments, the reactive oxygen species superoxide ($O_2^-$), $H_2O_2$, or both. In some other embodiments, the reactive oxygen species is superoxide ($O_2^-$). In some other embodiments, the reactive oxygen species is $H_2O_2$.

In some embodiments, the complex in the current invention or composition reacts with reactive oxygen species without a co-analyte and does not display a response to molecular oxygen.

In some embodiments, the complex in the current invention or composition has a log K value from about 8-15, about 9-12, about 9-14, about 10-13, about 11-12, about 8-14, about 8-12, about 8-11, about 8-10, about 8-13, about 9, about 10, about 11, about 12, about 8, about 12, about 13, about 14, about 15, about 14.5, about 13.5, about 12.5, about 11.5, about 10.5, about 9.5, or about 8.5. In some other embodiments, the complex has a log K of about 8-15.

In some embodiments, the complex in the current invention or composition has one or more $pK_a$ values of about 7, about 8, about 9, about 10, about 11, about 12, about 13, about 14, about 15, about 7-15, about 8-14, about 9-13, about 10-12, about 7-11, about 8-10, about 7-10, about 7-9, or about 7-9.

In some embodiments, the complex in the current invention or composition, before its oxidation by a ROS, has a $T_1$-weighted relaxivity of about 3-8 $mM^{-1}s^{-1}$, about 4-7 $mM^{-1}s^{-1}$, about 4-6 $mM^{-1}s^{-1}$, about 3-7 $mM^{-1}s^{-1}$, about 2-8 $mM^{-1}s^{-1}$, about 2-3 $mM^{-1}s^{-1}$, about 3-4 $mM^{-1}s^{-1}$, about 4-5 $mM^{-1}s^{-1}$, about 5-6 $mM^{-1}s^{-1}$, about 6-7 $mM^{-1}s^{-1}$, about 7-8 $mM^{-1}s^{-1}$, about 3 $mM^{-1}s^{-1}$, about 4 $mM^{-1}s^{-1}$, about 5 $mM^{-1}s^{-1}$, about 6 $mM^{-1}s^{-1}$, about 7 $mM^{-1}s^{-1}$, about 8 $mM^{-1}s^{-1}$, about 3.5 $mM^{-1}s^{-1}$, about 4.5 $mM^{-1}s^{-1}$, about 5.5 $mM^{-1}s^{-1}$, about 6.5 $mM^{-1}s^{-1}$, or about 7.5 $mM^{-1}s^{-1}$.

In some embodiments, the complex in the current invention or composition increases its $T_1$-weighted relaxivity upon reacting with the reactive oxygen species. In some embodiments, the complex increases its $T_1$-weighted relaxivity upon reacting with the reactive oxygen species by more than about 0.8 $mM^{-1}s^{-1}$, about 0.1 $mM^{-1}s^{-1}$, 0.2 $mM^{-1}s^{-1}$, 0.3 $mM^{-1}s^{-1}$, 0.4 $mM^{-1}s^{-1}$, 0.5 $mM^{-1}s^{-1}$, 0.6 $mM^{-1}s^{-1}$, 0.7 $mM^{-1}s^{-1}$, 0.9 $mM^{-1}s^{-1}$, 1.0 $mM^{-1}s^{-1}$, 1.5 $mM^{-1}s^{-1}$, or 2.0 $mM^{-1}s^{-1}$.

In some embodiments, the metal complex in the current invention or composition has a redox potential, relative to a NHE, of about 100-500 mV, about 150-450 mV, about 200-400 mV, about 250-350 mV, about 100-200 mV, about 200-300 mV, about 300-400 mV, about 400-500 mV, about 50-150 mV, about 50-100 mV, about 150-200 mV, about 200-250 mV, about 250-300 mV, about 300-350 mV, about 350-400 mV, about 400-450 mV, about 450-500 mV, about 300 mV, about 250 mV, about 200 mV, about 150 mV, about 150 mV, about 50 mV, or about 25 mV.

In some embodiments, the ligand of the complex in the composition is oxidized upon reacting with the reactive oxygen species. In some other embodiments, the complex does not change the metal ion's oxidation state upon reacting with the reactive oxygen species. In yet some other embodiments, the complex's reaction with the reactive oxygen species is reversible.

In another embodiments, the complex is [Mn(H$_2$qtp1)(MeCN)]$^{2+}$, wherein MeCN is acetonitrile and H$_2$qtp1 is

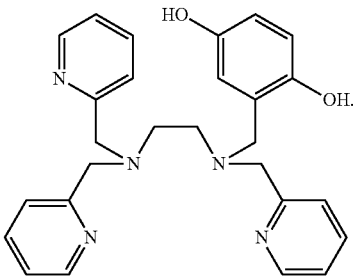 [SMILES: Oc1ccc(O)c(CN(CCN(Cc2ccccn2)Cc2ccccn2)Cc2ccccn2)c1]

In yet some other embodiments, wherein the complex is [Mn(H$_4$qtp2)Br$_2$], wherein H$_4$qtp2 is

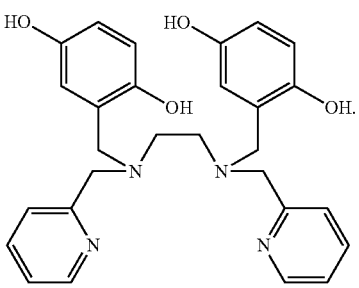 [SMILES: Oc1ccc(O)c(CN(CCN(Cc2ccccn2)Cc2cc(O)ccc2O)Cc2ccccn2)c1]

Magnetic Resonance Imaging Contrast Agent Composition Comprising a Metal Complex In yet another aspect, the present invention is a magnetic resonance imaging (MRI) contrast agent composition comprising such a complex and such a complex reacts with a reactive oxygen species within a subject.

As used herein, the term "MRI contrast agent" refers to a substance that increases the contrast of an MRI scan, usually by modulating how water-rich and water-poor regions of the tissue, organ, or body absorb radiofrequency radiation.

As used here, the term "oxidative stress" refers to the overproduction of one or more reactive oxygen species, such the concentrations of these reactive oxygen species are substantially elevated relative to healthy, baseline levels, or an unbalance between pro-oxidants and antioxidant mechanisms. Alternatively, the term "oxidative stress" refers to a build-up of reactive oxygen species resulting in alterations in membrane lipids, proteins and nucleic acids leading to lipid peroxidation, protein carbonylation and DNA strand breaks. Oxidative stress results in excessive oxidative metabolism. This stress can be due to several environmental factors such as exposure to pollutants, alcohol, medications, infections, poor diet, toxins, radiation etc. Oxidative damage to DNA, proteins, and other macromolecules may lead to a wide range of human diseases most notably heart disease and cancer.

A compound's antioxidant activity is usually measured by one or more assays. In one assay, superoxide was produced in situ from a reaction between xanthine and xanthine oxidase. The subsequent reaction of the $O_2^-$ with lucigenin provided a spectroscopic signal that can be used to provide a qualitative measure of an anti-oxidant's ability to degrade $O_2^-$. The copper/zinc superoxide dismutase isolated from bovine erythrocytes (0.001-100 U/ml, Calbiochem) was used as a positive control.

The DPPH (2,2-diphenyl-1-picryl-hydrazyl-hydrate) free radical method is an alternative antioxidant activity assay based on electron-transfer that produces a violet solution in ethanol or methanol. This free radical, stable at room temperature, is reduced in the presence of an antioxidant molecule, giving rise to colorless ethanol or methanol solution. The use of the DPPH assay provides an easy and rapid way to evaluate antioxidants by spectrophotometry, so it can be useful to assess various products at a time.

A compound's cytotoxicity as used here is evaluated using H9c2 cells. To determine the cytotoxic effects of compounds, the H9c2 cells were exposed to increasing concentrations of these compounds or their vehicle in Dulbecco's Modified Eagle Medium (DMEM) for either 4 or 24 h. The cell number was assessed using the CyQUANT Cell Proliferation Assay Kit (Life Technologies Corporation, Carlsbad, Calif.) per manufacturer's instructions. Cell number was expressed as a percentage of that measured for the vehicle-treated cells. Values are expressed as mean and standard error of the mean (SEM).

In some embodiments, a contrast agent composition for magnetic resonance imaging comprising a metal complex of a following generic formula, $[M(A)(B)]^x$, wherein, M is $Mn^{2+}$, $Ni^{2+}$, $Co^{2+}$, $Fe^{2+}$, or a combination thereof; B is absent, acetonitrile, methanol, $Cl^-$, $Br^-$, $I^-$, water, perchlorate, triflate, a small inorganic or organic molecule or ion, mondentate, bidentate, or a combination thereof, A is a ligand of formula II

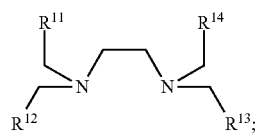

and
x is an integer between 6 and −6, wherein $R^{11}$, $R^{12}$, $R^{13}$, and $R^{14}$ are independently a substituted or unsubstituted 5-6-membered heteroaryl group and at least one of $R^{11}$, $R^{12}$, $R^{13}$, and $R^{14}$ is a substituted or unsubstituted quinolyl group, and the metal complex reacts with a reactive oxygen species within a subject.

In some other embodiments, for the metal complex in the contrast agent composition, $R^{11}$, $R^{12}$, $R^{13}$, and $R^{14}$ are independently a unsubstituted or substituted pyridinyl, pyrazinyl, pyrimidinyl, pyridazinyl, 1,2,3-triazinyl, 1,2,4-trazinyl, 1,3,5-triazinyl, quinolyl, phenolyl group, or an isomer thereof, at least one of $R^{11}$, $R^{12}$, $R^{13}$, and $R^{14}$ is a substituted or unsubstituted quinolyl group.

In some embodiments, in the disclosed metal complexes, B is absent. In some other embodiments, B is acetonitrile, methanol, $Cl^-$, $Br^-$, $I^-$, ethanol, water, perchlorate, triflate, a small inorganic or organic molecule or ion, monodentate, bidentate, or a combination thereof. A small inorganic or organic molecule or ion as used here means a molecule or ion that is similar to those specified above and contains a heteronuclear atom to provide a lone electron pair to the metal ion M.

In some embodiments, the metal complexes is neutral, i.e., x is 0. In some other embodiments, the metal complexes has a charge of 6, 5, 4, 3, 2, 1, −1, −2, −3, −4, −5, or −6, depending on the charge states of both B and organic ligand A. Preferably, the charge of the metal complexes is between 3 and −3.

In some embodiments, in the complex of the contrast agent composition, the ligand has a following formula

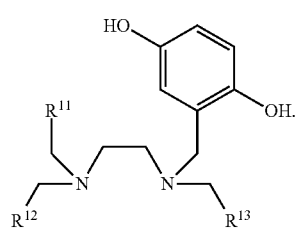

In some other embodiments, for the ligand of the complex in the contrast agent composition, the $R^{11}$ and $R^{14}$ are independently a substituted or unsubstituted quinolyl group. In some other embodiments, the ligand has a following formula

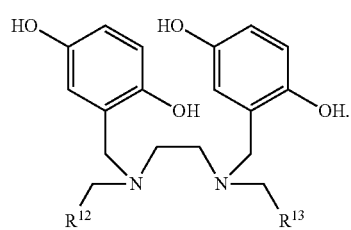

In yet some other embodiments, the ligand has a following formula

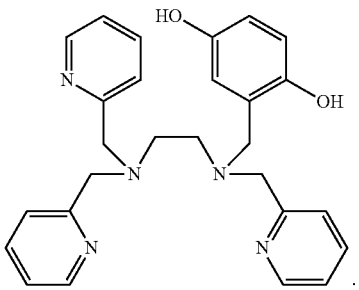 [SMILES: Oc1ccc(O)c(CN(CCN(Cc2ccccn2)Cc2ccccn2)Cc2ccccn2)c1]

In some embodiments, the ligand has a following formula

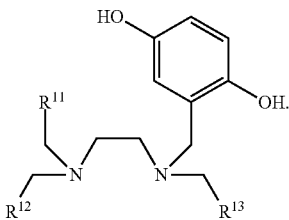

In some other embodiments, the ligand has a following formula

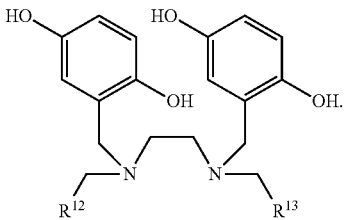

In some embodiments, in the complex of the contrast agent composition, the metal ion is $Mn^{2+}$. In some other embodiments, the reactive oxygen species that the complex of the contrast agent composition reacts with within a subject is superxoide ($O_2^-$), $H_2O_2$, or both. In some other embodiments, the reactive oxygen species that the complex of the contrast agent composition reacts with within a subject is $H_2O_2$. In some other embodiments, the reactive oxygen species that the complex of the contrast agent composition reacts with within a subject is superoxide ($O_2^-$).

In some embodiments, the subject within which the contrast agent composition is used is an animal or human.

In some embodiments, the complex in the contrast agent composition reacts with reactive oxygen species without a co-analyte and does not display a response to molecular oxygen.

In some embodiments, the complex in the contrast agent composition has a log K value from about 8-15, about 9-12, about 9-14, about 10-13, about 11-12, about 8-14, about 8-12, about 8-11, about 8-10, about 8-13, about 9, about 10, about 11, about 12, about 8, about 12, about 13, about 14, about 15, about 14.5, about 13.5, about 12.5, about 11.5, about 10.5, about 9.5, or about 8.5. In some other embodiments, the complex has a log K of about 8-15.

In some embodiments, the complex in the current invention or contrast agent composition, before its oxidation by a ROS, has a $T_1$-weighted relaxivity of about 3-8 $mM^{-1}s^{-1}$, about 4-7 $mM^{-1}s^{-1}$, about 4-6 $mM^{-1}s^{-1}$, about 3-7 $mM^{-1}s^{-1}$, about 2-8 $mM^{-1}s^{-1}$, about 2-3 $mM^{-1}s^{-1}$, about 3-4 $mM^{-1}s^{-1}$, about 4-5 $mM^{-1}s^{-1}$, about 5-6 $mM^{-1}s^{-1}$, about 6-7 $mM^{-1}s^{-1}$, about 7-8 $mM^{-1}s^{-1}$, about 3 $mM^{-1}s^{-1}$, about 4 $mM^{-1}s^{-1}$, about 5 $mM^{-1}s^{-1}$, about 6 $mM^{-1}s^{-1}$, about 7 $mM^{-1}s^{-1}$, about 8 $mM^{-1}s^{-1}$, about 3.5 $mM^{-1}s^{-1}$, about 4.5 $mM^{-1}s^{-1}$, about 5.5 $mM^{-1}s^{-1}$, about 6.5 $mM^{-1}s^{-1}$, or about 7.5 $mM^{-1}s^{-1}$.

In some embodiments, the complex in the contrast agent composition increases its $T_1$-weighted relaxivity upon reacting with the reactive oxygen species. In some embodiments, the complex increases its $T_1$-weighted relaxivity upon reacting with the reactive oxygen species by more than about 0.8 $mM^{-1}s^{-1}$, about 0.1 $mM^{-1}s^{-1}$, 0.2 $mM^{-1}s^{-1}$, 0.3 $mM^{-1}s^{-1}$, 0.4 $mM^{-1}s^{-1}$, 0.5 $mM^{-1}s^{-1}$, 0.6 $mM^{-1}s^{-1}$, 0.7 $mM^{-1}s^{-1}$, 0.9 $mM^{-1}s^{-1}$, 1.0 $mM^{-1}s^{-1}$, 1.5 $mM-1s^{-1}$, or 2.0 $mM^{-1}s^{-1}$.

In some embodiments, a complex in the current invention has one or more $pK_a$ values has one or more $pK_a$ values of about 7, about 8, about 9, about 10, about 11, about 12, about 13, about 14, about 15, about 7-15, about 8-14, about 9-13, about 10-12, about 7-11, about 8-10, about 7-10, about 7-9, or about 7-9.

In some embodiments, the ligand of the complex in the contrast agent is oxidized upon reacting with the reactive oxygen species. In some other embodiments, the complex does not change the metal ion's oxidation state upon reacting with the reactive oxygen species. In yet some other embodiments, the complex's reaction with the reactive oxygen species is reversible.

In some embodiments, the complex in the contrast agent is [Mn(H$_2$qtp1)(MeCN)]$^{2+}$, wherein MeCN is acetonitrile and H$_2$qtp1 is

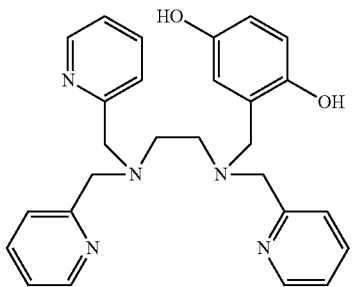

In some other embodiments, the complex is [Mn(H$_4$qtp2)Br$_2$], wherein H$_4$qtp2 is

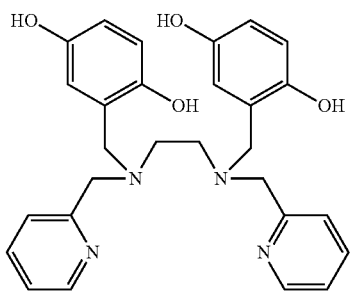

Method of Detecting a Reactive Oxygen Species Hotspot

In yet another aspect, the present invention is a method of detecting a reactive oxygen species hotspot in a subject using a MRI contrast agent composition. The MRI contrast agent used in this disclosed method may be one of those contrast agent compositions disclosed above.

As used herein, the term "a reactive oxygen species hotspot" refers to area in or within an organ or tissue with an abnormally high concentration of one or more reactive oxygen species. In the current state of art, what constitutes "abnormally high" remains to be investigated, since in vivo concentrations of reactive oxygen species have not been directly measured. The exact values will likely be highly dependent on the sort of tissue that is being investigated. The disclosed MRI imaging method and contrast agent compositions herein can help to fill this void by differentiating areas with relative a high concentrations of one or more reactive oxygen species from those areas with low concentrations, subsequently lead to estimations of reactive oxygen species concentration in different areas in or within an organ or tissue.

In some embodiments, a method of detecting a reactive oxygen species hotspot in a subject comprising providing a subject, applying a contrast agent to the subject, and performing magnetic resonance imaging on the subject after applying the contrast agent; wherein the contrast agent comprises a metal complex with an organic ligand, the metal complex reacts with a reactive oxygen species, the organic ligand is oxidized, the metal ion does not change oxidation state, the metal complex increases its $T_1$-weighted relaxivity, and the oxidation of the ligand is reversible.

In some other embodiments, the MRI contrast agent composition in the method is any of the MRI contrast agent compositions disclosed above.

In some other embodiments, the subject is a mammal or a human. In some other embodiments, the reactive oxygen species is $H_2O_2$.

Pharmaceutical Composition Comprising a Metal Complex

In another aspect, the present invention is a pharmaceutical composition comprising an effective amount of the metal complexes that are disclosed above, a stereoisomer thereof, a tautomer thereof, a tautomer of the stereoisomer, a pharmaceutically acceptable salt of any of the foregoing.

The term "pharmaceutically acceptable" is meant a composition suitable for use in treatment of humans and/or animals. Typically, the formulations are relatively non-toxic and do not cause additional side effects compared to the drug delivered. In the case of chemotherapeutics which are generally toxic, a "pharmaceutically acceptable" formulation is one which delivers an amount of drug sufficient to alleviate symptom or suffering, and yet sparing the patient although there maybe side effects inherent to the drug.

The term "pharmaceutically acceptable" also refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The term "a therapeutically effective amount" is meant an amount effective to achieve a desired and/or beneficial effect. An effective amount can be administered in one or more administrations. For purposes of this invention, a therapeutically effective amount is an amount appropriate to treat an indication such as oxidative stress. By treating an indication is meant achieving any desirable effect, such as the ability to palliate, ameliorate, stabilize, reverse, slow or delay disease progression, increase the quality of life, and/or to prolong life. Such achievement can be measured by any method known in the art, such as MRI scanning for reactive oxygen species, physical measurement of other indications, or measuring patient life.

The terms "pharmaceutically acceptable excipients", "pharmaceutically compatible excipients", and "excipients" are used interchangeably in this disclosure. They refer to non-API substances such as disintegrators, binders, fillers, and lubricants used in formulating pharmaceutical products. They are generally safe for administering to humans according to established governmental standards, including those promulgated by the United States Food and Drug Administration.

Disintegrators, as used herein, refer to one or more of agar-agar, algins, calcium carbonate, carboxmethylcellulose, cellulose, clays, colloid silicon dioxide, croscarmellose sodium, crospovidone, gums, magnesium aluminium silicate, methylcellulose, polacrilin potassium, sodium alginate, low substituted hydroxypropylcellulose, and cross-linked polyvinylpyrrolidone hydroxypropylcellulose, sodium starch glycolate, and starch. Examples of disintegrators include agar-agar, algins, calcium carbonate, carboxmethylcellulose, cellulose, clay, colloid silicon dioxide, croscarmellose sodium, crospovidone, gums, magnesium aluminium silicate, methylcellulose, polacrilin potassium, sodium alginate, low substituted hydroxypropylcellulose, and cross-linked polyvinylpyrrolidone hydroxypropylcellulose, sodium starch glycolate, and starch.

Binders, as used herein, refer to one or more of microcrystalline cellulose, hydroxymethyl cellulose, hydroxypropylcellulose, and polyvinylpyrrolidone.

Fillers, as used herein, refer to one or more of calcium carbonate, calcium phosphate, dibasic calcium phosphate, tribasic calcium sulfate, calcium carboxymethylcellulose, cellulose, dextrin derivatives, dextrin, dextrose, fructose, lactitol, lactose, magnesium carbonate, magnesium oxide, maltitol, maltodextrins, maltose, sorbitol, starch, sucrose, sugar, and xylitol. Examples of fillers include calcium carbonate, calcium phosphate, dibasic calcium phosphate, tribasic calcium sulfate, calcium carboxymethylcellulose, cellulose, dextrin derivatives, dextrin, dextrose, fructose, lactitol, lactose, magnesium carbonate, magnesium oxide, maltitol, maltodextrins, maltose, sorbitol, starch, sucrose, sugar, and xylitol.

Lubricants, as used herein, refer to one or more of agar, calcium stearate, ethyl oleate, ethyl laureate, glycerin, glyceryl palmitostearate, hydrogenated vegetable oil, magnesium oxide, magnesium stearate, mannitol, poloxamer, glycols, sodium benzoate, sodium lauryl sulfate, sodium stearyl, sorbitol, stearic acid, talc, and zinc stearate. Examples of lubricants include agar, calcium stearate, ethyl oleate, ethyl laureate, glycerin, glyceryl palmitostearate, hydrogenated vegetable oil, magnesium oxide, magnesium stearate, mannitol, poloxamer, glycols, sodium benzoate, sodium lauryl sulfate, sodium stearyl, sorbitol, stearic acid, talc, and zinc stearate.

Suitable pharmaceutically acceptable excipients also include the following types of excipients: diluents, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (Mack Publishing Company). Accordingly, another embodiment of this invention is a method of preparing a pharmaceutical composition comprising the step of admixing crystalline metal complexes disclosed herein with one or more pharmaceutically acceptable excipients.

In some embodiments, a pharmaceutical composition of the current invention is one comprising any one of the complexes disclosed above, a stereoisomer thereof, a tautomer thereof, a tautomer of the stereoisomer, a pharmaceutically acceptable salt of any of the foregoing, as the active ingredient, and one or more pharmaceutically acceptable excipients.

Those skilled in the art will appreciate that the metal complexes of the present technology may exhibit the phenomena of tautomerism, conformational isomerism, geometric isomerism, isotopic isomerism, and/or stereoisomerism. As the formula drawings within the specification and claims can represent only one of the possible tautomeric, conformational isomeric, isotopic isomeric, stereochemical or geometric isomeric forms, it should be understood that the present technology encompasses any tautomeric, isotopic isomeric, conformational isomeric, stereochemical and/or geometric isomeric forms of the metal complexes having one or more of the utilities described herein, as well as mixtures of these various different forms. As used herein, an "isomer" includes any one of above mentioned isomeric forms for any group or disclosed complexes.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution.

As readily understood by one skilled in the art, a wide variety of functional groups and other structures may exhibit tautomerism, and all tautomers of compounds as described herein are within the scope of the present invention.

Stereoisomers of compounds (also known as optical isomers) include all chiral, diasteromeric, and racemic forms of a structure, unless the specific stereochemistry is expressly indicated. Thus, compounds disclosed herein include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

Method of Treatment or Method of MRI Imaging and Treatment

In yet another aspect, the present invention is a method of treatment comprising administering to a subject having oxidative stress such a pharmaceutical composition that is described above and comprises the metal complexes disclosed above.

In another aspect, the present invention is method of detecting a reactive oxygen species hotspot in a subject and alleviating the oxidative stress thereof at the same time comprising administering to a subject a therapeutically and magnetic resonance imaging effective amount of such a composition that is described above and comprises the metal complexes disclosed above.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Materials

Except where stated otherwise, all chemicals were purchased from Sigma-Aldrich and used as received. 2,2-Diphenyl-1-picryl-hydrazyl hydrate (DPPH) was bought from EMD Millipore. Deuterated acetonitrile (MeCN-$d_3$) was bought from Cambridge Isotopes. Diethyl ether (ether) and methanol (MeOH) were purchased from Fisher. Methylene chloride ($CH_2Cl_2$) was bought from Mallinckrodt Baker.

Instrumentation

All $^1H$ and $^{13}C$ NMR spectra were recorded on a 400 MHz AV Bruker NMR spectrometer; all reported resonances were referenced to internal standards. Electron paramagnetic resonance (EPR) spectra were collected using a Bruker EMX-6/1 X-band EPR spectrometer operated in the perpendicular mode. The acquired data were analyzed with the program EasySpin. Each sample was run as a frozen solution in a quartz tube. High-resolution mass spectrometry (HR-MS) data were obtained at the Mass Spectrometer Center at Auburn University on a Bruker microflex LT MALDI-TOF mass spectrometer via direct probe analysis operated in the positive ion mode. IR data were collected using a Shimadzu IR Prestige-21 FT-IR spectrophotometer. A Johnson Matthey magnetic susceptibility balance (model MK I#7967) was used to measure the magnetic properties of the Mn(II) complex with $H_2qtp1$; the reported eff value was the average of those measured for two independently prepared solid samples. Atlantic Microlabs (Norcross, Ga.) performed the elemental analyses (C, H, N). All samples submitted for elemental analysis were crystallized and dried under vacuum prior to their shipment. All cyclic voltammetry was performed under $N_2$ at 294 K using an Epsilon electrochemistry workstation (Bioanalytical System, Inc.), a gold working electrode, a platinum wire auxiliary electrode, and a Ag/AgCl reference electrode.

X-Ray Crystallography

The structural data were obtained at the University of Alabama, Birmingham. After the data were corrected for Lorentz and polarization effects, the structures were solved using direct methods and expanded using Fourier techniques. All non-hydrogen atoms were refined anisotropically. Hydrogen atoms were included at idealized positions 0.95 Å from their parent atoms prior to the final refinement. Further details regarding the data acquisition and analysis are included on Table S1.

Measurement of Binding Affinity for Mn(II) for a Ligand

The log(K) was measured via a competitive binding assay between N,N,N',N'-tetrakis(2-pyridylmethyl)ethylenediamine (TPEN) and the ligand (L). Various amounts of TPEN were added to a solutions of the ligand in MeCN-$d_3$ and $D_2O$.

Magnetic Resonance Imaging (MRI)

All MRI data were collected at the Auburn University MRI Research Center (Auburn, Ala.) on a Siemens Verio open-bore 3-T MRI clinical scanner. A 15-channel knee coil was used to simultaneously image 12-26 samples. An inversion recovery (IR) sequence was used that featured a non-selective adiabatic inversion pulse followed by a slice-selective gradient recalled echo (GRE) readout after a delay period corresponding to the inversion time (TI).[1-2] The GRE was a saturation readout, such that only one line of k-space was acquired per repetition time (TR). This method was selected to maximize both the signal strength and the accuracy of the $T_1$ estimates. Specific imaging parameters were as follows: TR was set to 4 s, TI was varied from 4.8 to 2500 ms over 37 steps, the echo time (TE) was set to 3.6 ms, the flip angle equaled 90°, averages=1, slice thickness=5 mm, field of view=140×140 mm, matrix=128×128, resulting in a pixel size of 1.1×1.1×5.0 mm. All samples were run in 50 mM solutions of HEPES in water, buffered to pH 7.0 and kept at 22° C. The manganese content was systematically varied from 0.10 to 1.00 mM. The inverses of the $T_1$ values were plotted versus the concentration of Mn(II) to obtain $r_1$ values. All reported $r_1$ values are averages from the results of two separate series of experiments. Each series of experiments used a different batch of 1.

MRI Data Analysis

Image analysis was performed using custom Matlab programs (Mathworks, Natick, Mass.). The initial TI=4.8 ms image served as a baseline to determine circular region of interest (ROI) boundaries for each sample; from these, the mean pixel magnitudes for each ROI were calculated. For each of the 36 subsequent TI images, the same ROI boundaries were applied and the mean pixel magnitude calculations were repeated. This gave consistent ROI spatial definitions and a corresponding time course of magnitudes for each of the samples over all the TI time points. Each sample's complex phase was used to correct the magnitude polarity to produce a complete exponential $T_1$ inversion recovery curve. The Nelder-Mead simplex algorithm[3] was applied to each sample's exponential curve to estimate its corresponding $T_1$ value.

Analysis of Anti-Oxidant Properties of Mn(II) Complexes

Superoxide was produced in situ from a reaction between xanthine and xanthine oxidase. The subsequent reaction of the $O_2^-$ with lucigenin provided a spectroscopic signal that can be used to provide a qualitative measure of an anti-oxidant's ability to degrade $O_2^-$. The copper/zinc superoxide dismutase isolated from bovine erythrocytes (0.001-100 U/ml, Calbiochem) was used as a positive control. The assay was carried out in a total volume of 1 mL containing 50 mM tris (pH 8.0), hypoxanthine (50 μM), xanthine oxidase (0.005 U/ml, Calbiochem) and dark adapted lucigenin (5 μM) in the presence of a complex (0.1 nM-10 μM) or their vehicle. Reactions were carried out at room temperature and were initiated by the addition of xanthine oxidase to the hypoxanthine-containing solution. Luminescence was measured using a TD-20/20 (Turner Designs) luminometer and expressed as relative light units (RLU). Luminescence was measure for four 10 s integrations after an initial delay of 3 s. The four RLU values were averaged, and each concentration was expressed as a percent of that produced in the presence of vehicle. Each assay data point was performed in duplicate and assays were repeated three times.

An alternative assessment of the Mn(II) complexes' anti-oxidant properties relied upon the DPPH assay. Aqueous solutions of either 1, 2, or ascorbic acid were added to a solution of 0.10 mM DPPH in MeOH, such that the final reaction volume was 0.2 mL. Samples were incubated in the dark for 30 min at room temperature. Spectrophotometric measurements were subsequently performed at 517 nm using a Molecular Devices Spectramax Plus. This wavelength corresponds to the $\lambda_{max}$ of the reduced product. Experiments were performed in triplicate and repeated twice.

Cytotoxicity Studies

H9c2 cells were obtained from the American Tissue Type Collection (Manassas, Va., USA) and grown at 37° C. with 95% humidity and 5% $CO_2$. Cells were grown in Dulbecco's modified eagles medium (DMEM) supplemented with 10% fetal bovine serum. Experiments were performed at 70-80% confluence. All experiments were performed in DMEM in the absence of fetal bovine serum. To determine the cytotoxic effects of 1 and 2, the H9c2 cells were exposed to increasing concentrations of these reagents or their vehicle in DMEM for either 4 or 24 h. The cell number was assessed using the CyQUANT Cell Proliferation Assay Kit (Life Technologies Corporation, Carlsbad, Calif.) per manufacturer's instructions. Cell number was expressed as a percentage of that measured for the vehicle-treated cells. Values are expressed as mean and SEM and represent three experiments performed in triplicate.

Example 1

Syntheses and Characterization of N,N,N'-tris(2-pyridinylmethyl)-1,2-ethanediamine The procedure to synthesize and characterize N,N,N'-tris(2-pyridinyl-methyl)-1,2-ethanediamine is described in a paper by Mialane, et al. (Mialane, P.; Nivorojkine, A.; Pratviel, G.; Azêma, L.; Slany, M.; Godde, F.; Simaan, A.; Banse, F.; Kargar-Grisel, T.; Bouchoux, G.; Sainton, J.; Homer, O.; Guilhem, J.; Tchertanova, L.; Meunier, B.; Girerd, J.-J. *Inorg. Chem.* 1999, 38 (6), 1085-1092.) This Mialane paper is herein incorporated by reference in its entirety.

Syntheses and Characterization of a Mononuclear Mn(II) Complex with the Redox-Active Ligand N-(2,5-dihydroxybenzyl)-N,N',N'-tris(2-pyridinylmethyl)-1,2-ethanediamine ($H_2$qtp1)

For the organic component of the sensor, the hexadentate ligand N-(2,5-dihydroxybenzyl)-N,N',N'-tris(2-pyridinylmethyl)-1,2-ethanediamine ($H_2$qtp1, Scheme 1) is synthesized. The $H_2$qtp1 ligand is prepared in one step from a reaction between the synthesized N,N,N'-tris(2-pyridinylmethyl)-1,2-ethanediamine and commercially available 2,5- dihydroxybenzaldehyde. Pure H₂qtp1 can be obtained through precipitation of the crude from methanol/ether (40% yield).

Scheme 1

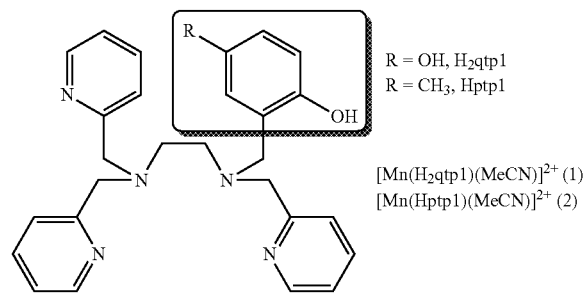

N-(2,5-Dihydroxybenzyl)-N,N',N'-tris(2-pyridinylmethyl)-1,2-ethanediamine (H₂qtp1)

N,N,N'-Tris(2-pyridinylmethyl)-1,2-ethanediamine (2.31 g, 6.93 mmol) and 2,5-dihydroxybenzaldehyde (1.05 g, 7.63 mmol) were dissolved in 40 mL of 1,2-dichloroethane. Subsequently, NaBH(OAc)₃ (4.43 g, 20.8 mmol) was added as a solid over 1 h. The resultant mixture was stirred for 24 h, at which point 80 mL of saturated NaHCO₃ solution were added to quench the reaction. The crude product was extracted with three 40 mL portions of CH₂Cl₂. The combined extracts were washed with one 40 mL portion of H₂O then dried over anhydrous Na₂SO₄. Evaporation of the solvent yielded the crude product, which was further purified via precipitation from a MeOH/ether mixture to yield a pale yellow powder (1.25 g, 40% yield). $^1$H NMR (400 MHz, CDCl₃, 293 K): δ 8.53 (1H, d, J=4.8 Hz), 8.49 (2H, d, J=4.8 Hz), 7.59 (3H, m), 7.50 (2H, d, J=8.0 Hz), 7.23 (1H, d, J=8.0 Hz), 7.13 (3H, m), 6.68 (2H, m), 6.48 (1H, d, J=4.8 Hz), 3.73 (6H, s), 3.59 (2H, s), 2.74 (4H, s). $^{13}$C NMR (400 MHz, CDCl₃, 293 K): δ 159.11, 157.68, 148.91, 148.83, 136.82, 136.60, 123.51, 123.29, 123.01, 122.43, 122.08, 116.87, 116.34, 115.67, 60.24, 59.53, 56.94, 50.71, 50.66. IR (KBr, cm$^{-1}$): 3380 (m), 3148 (s), 3126 (s), 2929 (m), 2879 (w), 2718 (w), 2617 (w), 1655 (w), 1596 (m), 1569 (m), 1490 (s), 1435 (s), 1400 (s), 1368 (s), 1249 (m), 1204 (w), 1147 (w), 1009 (w), 936 (w), 860 (w), 826 (w), 817 (w), 760 (s), 713 (w). MS (ESI): Calcd for MH⁺ 456.2400. Found, 456.2341.

Acetonitrilo(N-(2,5-dihydroxy-benzyl)-N,N',N'-tris(2-pyridinylmethyl)-1,2-ethanediamine)manganese (II) triflate ([Mn(H₂qtp1)(MeCN)](OTf)₂, 1)

The H₂qpt1 ligand (500 mg, 1.10 mmol) and Mn(OTf)₂ (388 mg, 1.10 mmol) were dissolved in 2 mL of MeCN under N₂. The solution was allowed to stir at room temperature for 16 h. After this time, 2 mL of ether were added to the solution, and the mixture was transferred to a −40° C. freezer. The product deposited as a white powder over several hours (660 mg, 74% yield). Crystals suitable for single crystal X-ray diffraction were grown from the diffusion of ether into a saturated solution of the powder in MeCN. Solid-state magnetic susceptibility (295 K): $\mu_{eff}$=5.6$\mu_B$. UV/vis (H₂O, 294 K): 262 nm (9370 M$^{-1}$ cm$^{-1}$), 292 nm (2550 M$^{-1}$ cm$^{-1}$). MS (ESI): Calcd for [Mn(L-H)]⁺, 509.1624 and for [Mn(L)(OTf)]⁺, 659.1222. Found, 509.1630 and 659.1226. IR (KBr, cm$^{-1}$): 3384 (m), 2957 (w), 2858 (w), 2697 (w), 1695 (w), 1605 (s), 1573 (w), 1505 (m), 1483 (m), 1445 (m), 1368 (m), 1346 (m), 1606 (s), 1294 (s), 1249 (s), 1224 (s), 1203 (s), 1170 (s), 1154 (s), 1076 (m), 1030 (s), 1011 (m), 1259 (m), 976 (w), 963 (w), 940 (w), 882 (w), 854 (w), 827 (w), 771 (m), 638 (s), 917 (m), 574 (m), 516 (m), 412 (w). EPR (H₂O, 77 K): $g_{eff}$=1.98. Elemental Analysis: Calcd for C₂₉H₂₉N₅MnF₆O₈S₂·2H₂O: C, 41.24%; H, 3.94%; N, 8.29%. Found: C, 41.08%; H, 3.97%; N, 8.28%.

At first glance, H₂qtp1 strongly resembles the Hptp1 ligand, which has a methyl group installed para to the phenol hydroxyl group. The substitution of a hydroxyl group for the methyl, however, enables a fundamentally different chemical response to oxidants. The redox-active portion of H₂qtp1 is a quinol, which is anticipated to oxidize to a more weakly metal-coordinating para-quinone upon exposure to H₂O₂ (Scheme 2) instead of oxidatively coupling to other phenols like Hptp1. Although manganese was not previously known to catalyze quinol oxidation, other redox-active transition metal ions have been reported to do so.[5-6] The manganese therefore serves as both the paramagnetic reporter for the contrast agent and the catalyst for the oxidation of the ligand.

Scheme 2

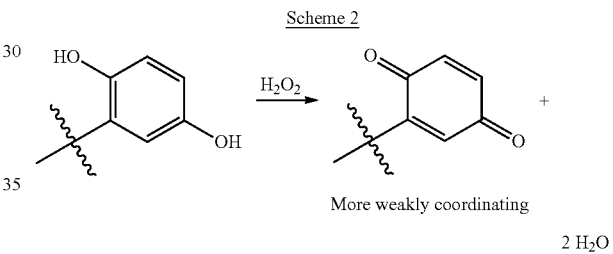

More weakly coordinating

2 H₂O

The reaction between H₂qtp1 and manganese(II) triflate in anaerobic acetonitrile yields [Mn(H₂qtp1)(MeCN)](OTf)₂ (Complex 1, MeCN=acetonitrile, OTf⁻=triflate). In a typical workup, the complex is crystallized from MeCN/Et₂O mixtures in 82% yield. The crystal structure of 1 reveals that the manganese center is heptacoordinate, with six donor atoms from the H₂qtp1 ligand and one from the coordinated MeCN (FIG. 1). The overall geometry is best described as a distorted face-capped octahedron, with the quinol O-donor and the three pyridine rings' N-donors defining a pseudo-plane. The heptacoordination and the metal-ligand bond distances are both consistent with a +2 oxidation state for the manganese. This assignment is supported by the lack of charge-transfer bands in the optical spectrum and the 5.6$\mu_B$ magnetic moment measured for the solid. The bound quinol remains fully protonated, as evidenced by the anion count and the Mn—O and C—O bond lengths. The C—O bond distances are both 1.38 Å, closely matching those found for quinols encapsulated in clathrates. Each hydroxyl group on the hydroquinone is in close proximity to an O atom from a OTf⁻ anion; the O—O distances (2.66 Å for O1, 2.71 Å for O2) are consistent with hydrogen bonding interactions. Selected crystallographic data and bond lengths for 1 are listed in Table 1S and S2.

TABLE S1

Selected crystallographic data for 1

| Parameter | [Mn(H$_2$qtp1)(MeCN)](OTf)$_2$ |
|---|---|
| Formula | C$_{31}$H$_{31}$F$_6$MnN$_6$O$_8$S$_2$ |
| MW | 848.70 |
| Crystal system | Monoclinic |
| Space group | P2$_1$/n(#14) |
| a (Å) | 13.08640(10) |
| b (Å) | 19.3897(2) |
| c (Å) | 14.42960(10) |
| α (deg) | 90 |
| β (deg) | 96.1260(10) |
| γ (deg) | 90 |
| V (Å$^3$) | 3640.48(5) |
| Z | 4 |
| Cryst color | Colorless |
| T | 100 |
| Reflns collected | 21924 |
| Unique reflns | 5605 |
| R1 (F, I > 2σ(I)) | 0.1098 |
| wR2 (F$^2$, all) | 0.3183 |

$R1 = \Sigma ||F_o| - |F_c|| / \Sigma |F_o|$; $wR2 = [\Sigma w(F_o^2 - F_c^2)^2 / \Sigma w(F_o^2)^2]^{1/2}$.

TABLE S2

Selected bond lengths for 1.

| Bond | Length (Å) |
|---|---|
| Mn—N(1) | 2.299(5) |
| Mn—N(2) | 2.401(5) |
| Mn—N(3) | 2.306(5) |
| Mn—N(4) | 2.325(5) |
| Mn—N(5) | 2.382(5) |
| Mn—N(6) | 2.284(5) |
| Mn—O(1) | 2.319(5) |
| C(27)—O(1) | 1.379(8) |
| C(24)—O(2) | 1.363(9) |

Complex 1 is sufficiently stable in aerobic water solutions to allow MRI measurements. The H$_2$qtp1 ligand does not dissociate from Mn(II) to a noticeable degree, as assessed by the lack of $^1$H NMR resonances in solutions of 1 in D$_2$O.

The log(K) for the complexation of H$_2$qtp1 to Mn(II) was estimated through a titration with the metal-scavenging agent TPEN (N,N,N',N'-tetrakis(2-pyridinylmethyl)ethylenediamine, log K=10.3). The ratios of free TPEN to free ligand were assessed by $^1$H NMR. From these data, equilibrium constants of 0.4 were assigned for the reactions in both water and MeCN:

[Mn(L)(MeCN)]$^{2+}$+TPEN→[Mn(TPEN)]$^{2+}$+L

Given the known log(K) of 10.3 for TPEN's binding to Mn(II), a log(K) of 10.7 was thereby assigned for the coordination of H$_2$qtp1 to Mn(II). Given the similarity of the values, we can assume that preferential protonation of either the TPEN or H$_2$qtp1 ligand does not occur to an extent large enough to impact the competitive binding of Mn(II). The log(K) of 10.7 is nearly identical to the 10.6 value estimated for a related ligand from our laboratory that contains a para-methylphenol group in place of the H$_2$qtp1's quinol.

Figure 2:
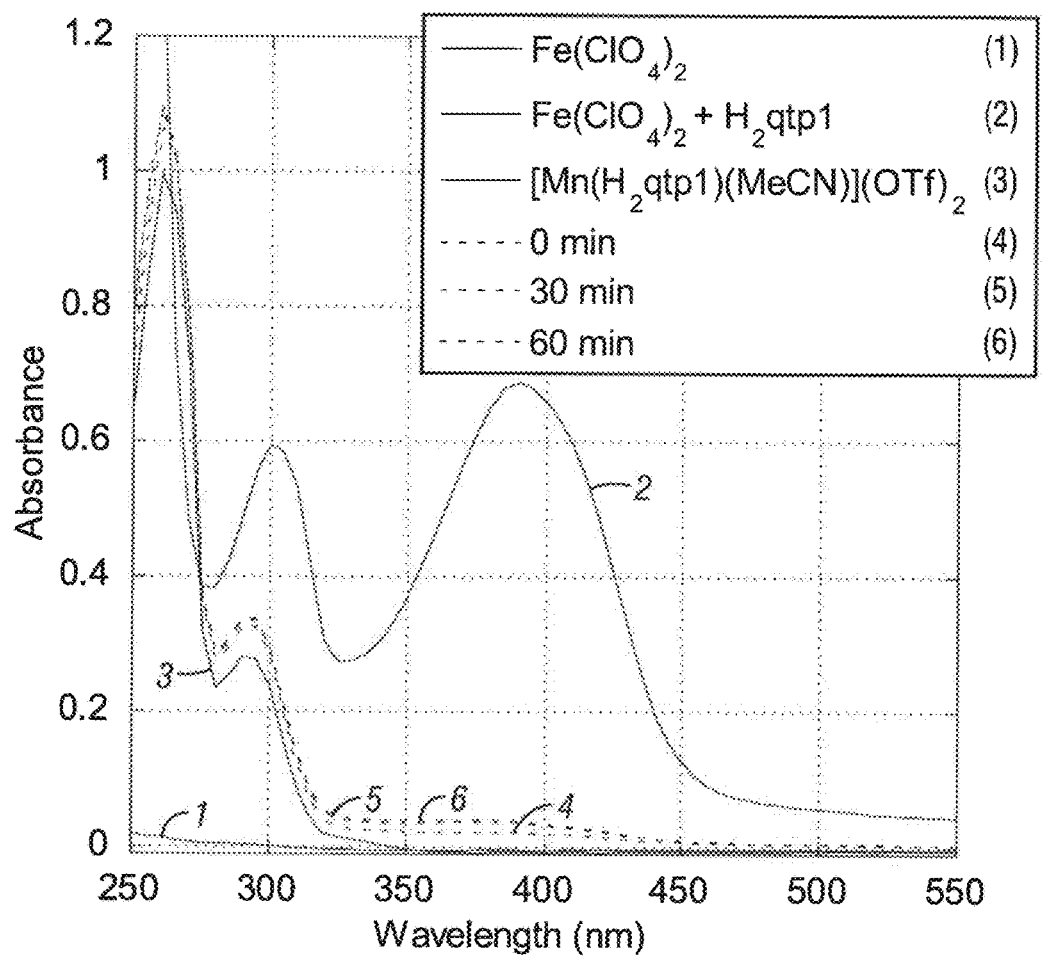
FIG. 2. The UV/vis spectra depicting the reaction between 0.10 mM $Fe(ClO_4)_2$ and 0.10 mM $[Mn(H_2qtp1)(MeCN)](OTf)_2$ (1) at 0, 30, and 60 min. The UV/vis spectra of 0.10 mM $Fe(ClO_4)_2$, the product of the reaction between 0.10 mM $Fe(ClO_4)_2$ and 0.10 mM $H_2qtp1$, and 0.1 mM $[Mn(H_2qtp1)(MeCN)](OTf)_2$ are provided for comparative purposes.
Figure 3:
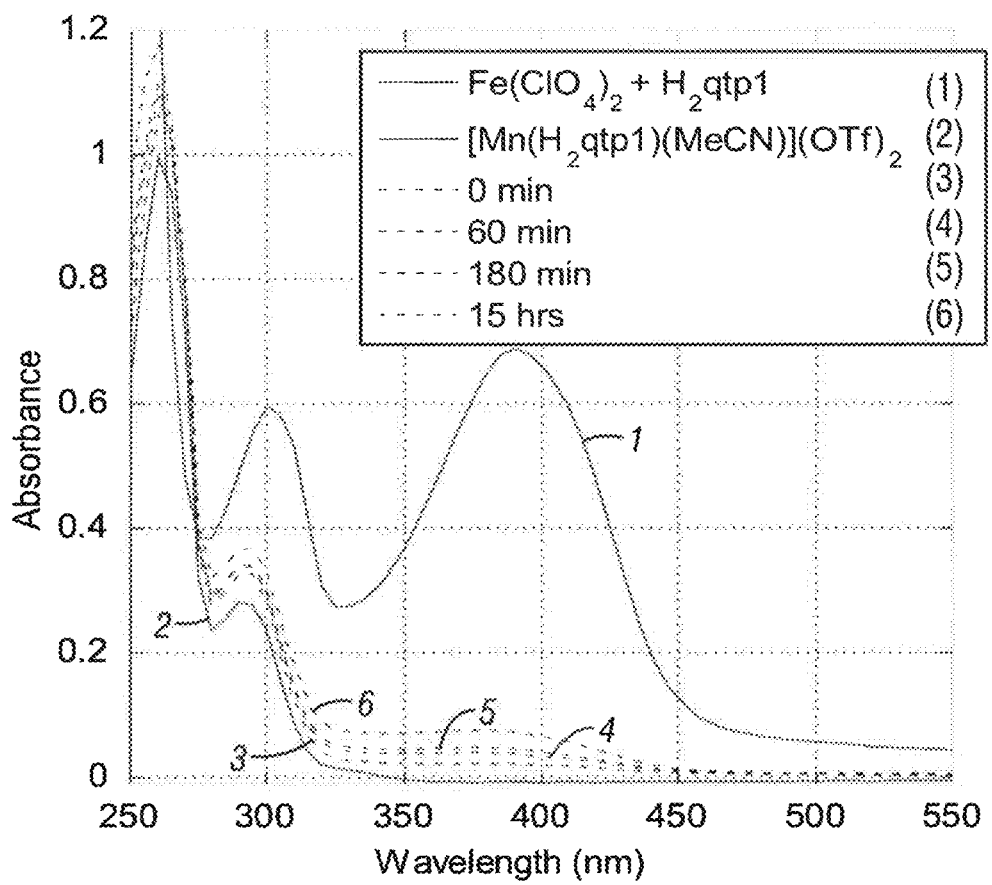
FIG. 3. The UV/vis spectra depicting the reaction between 0.10 mM $Fe(ClO_4)_2$ and 0.10 mM $[Mn(H_2qtp1)(MeCN)](OTf)_2$ at 0, 30, and 60 min, and 15 h. The UV/vis spectra measured for 0.10 mM $Fe(ClO_4)_2$, the product of the reaction between 0.10 mM $Fe(ClO_4)_2$ and 0.10 mM $H_2qtp1$, and 0.1 mM $[Mn(H_2qtp1)(MeCN)](OTf)_2$ are provided for comparative purposes.

Solutions of 1 in H$_2$O or MeCN are slightly sensitive towards oxygen, with the solutions slowly discoloring from light yellow to purple over 12 h. Over this time, collected UV/vis spectra (FIGS. 2 & 3) display changes in the region between 200 nm and 300 nm which are consistent with the oxidation of the quinol to a para-quinone. Past 24 h, the solution begins to turn brown, consistent with oxidation of the manganese to Mn(III) and/or Mn(IV). For the spectrophotometric analysis, the Fe(ClO$_4$)$_2$ solution was added to a MeCN solution containing 0.10 mM [Mn(Hptp1)(MeCN)]$^{2+}$; the mixture was scanned at 0 min (dashed red), 30 min (dashed pink), and 60 min (dashed blue). Over this time period, there was negligible displacement of the Mn(II) by Fe(II) as indicated by the data in FIG. 2. At 15 h, approximately 11% of the Mn(II) has been displaced by Fe(II) as indicated by data in FIG. 3.

Figure 4:
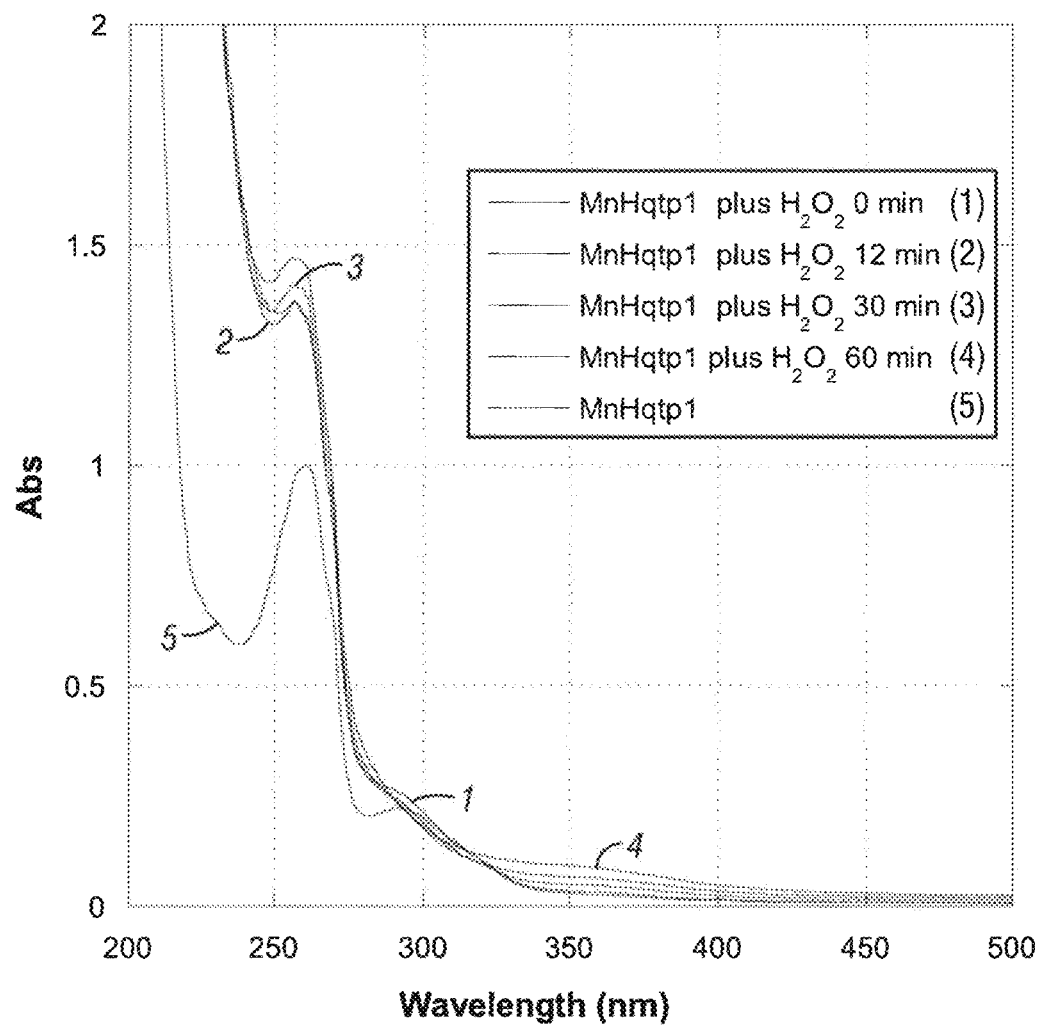
FIG. 4. UV/Vis spectra depicting the reaction between 0.10 mM 1 and 10 mM $H_2O_2$ in $H_2O$.

The reactivity between 1 and H$_2$O$_2$, conversely, is rapid. In MeCN, the reaction between 1 and excess H$_2$O$_2$ turns purple within a few minutes. FIG. 4 shows UV/Vis spectra spectra depicting the reaction between 0.10 mM 1 and 10 mM H$_2$O$_2$ in H$_2$O. The reaction was scanned immediately after the addition of H$_2$O$_2$, then 12, 30, and 60 min thereafter. The 292 nm feature in the non-oxidized material is typical of a quinol functional group.

Figure 5:
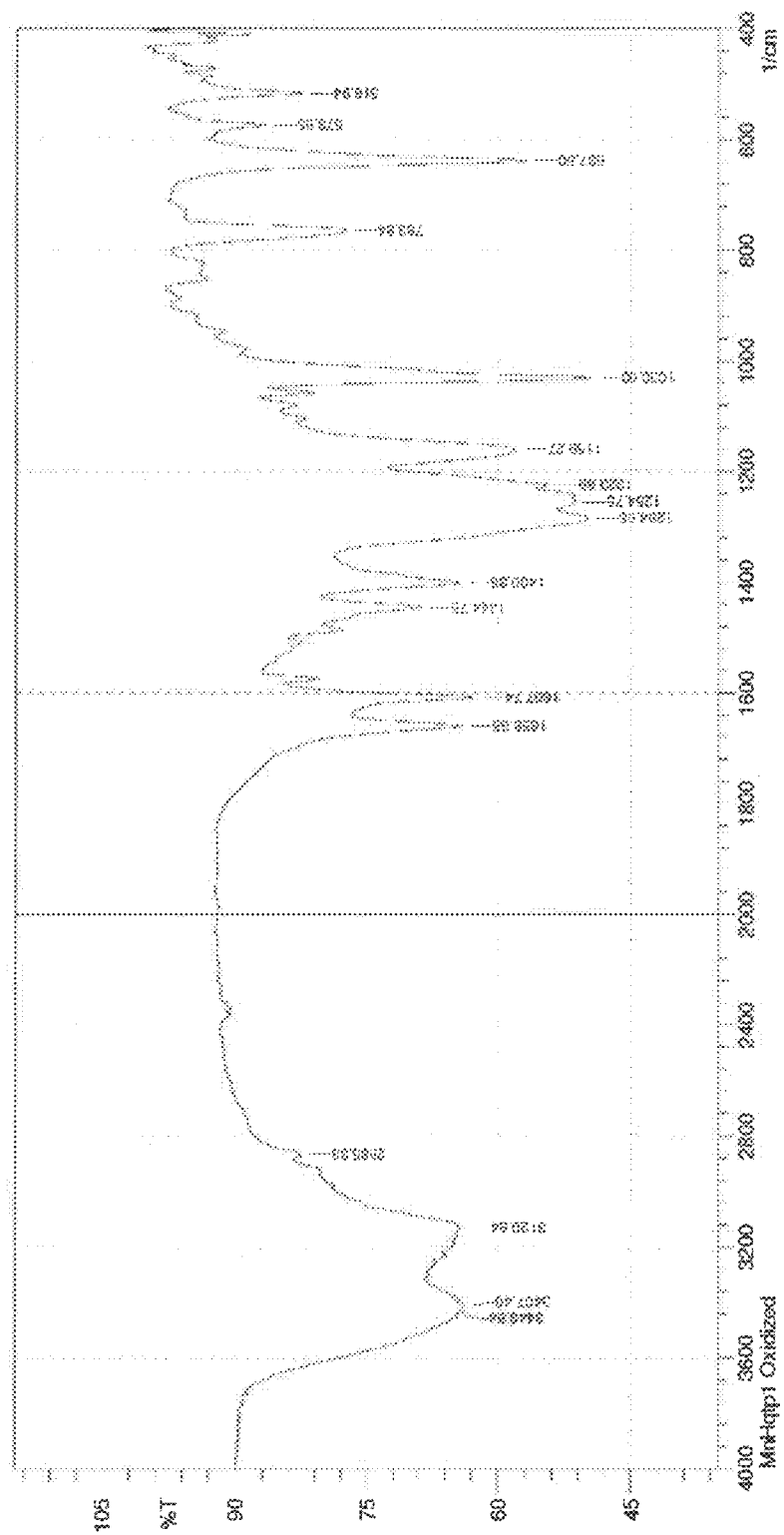
FIG. 5. IR spectrum of the crude product from the reaction between 1.0 mM 1 and 4.0 mM $H_2O_2$ in MeOH.
Figure 6:
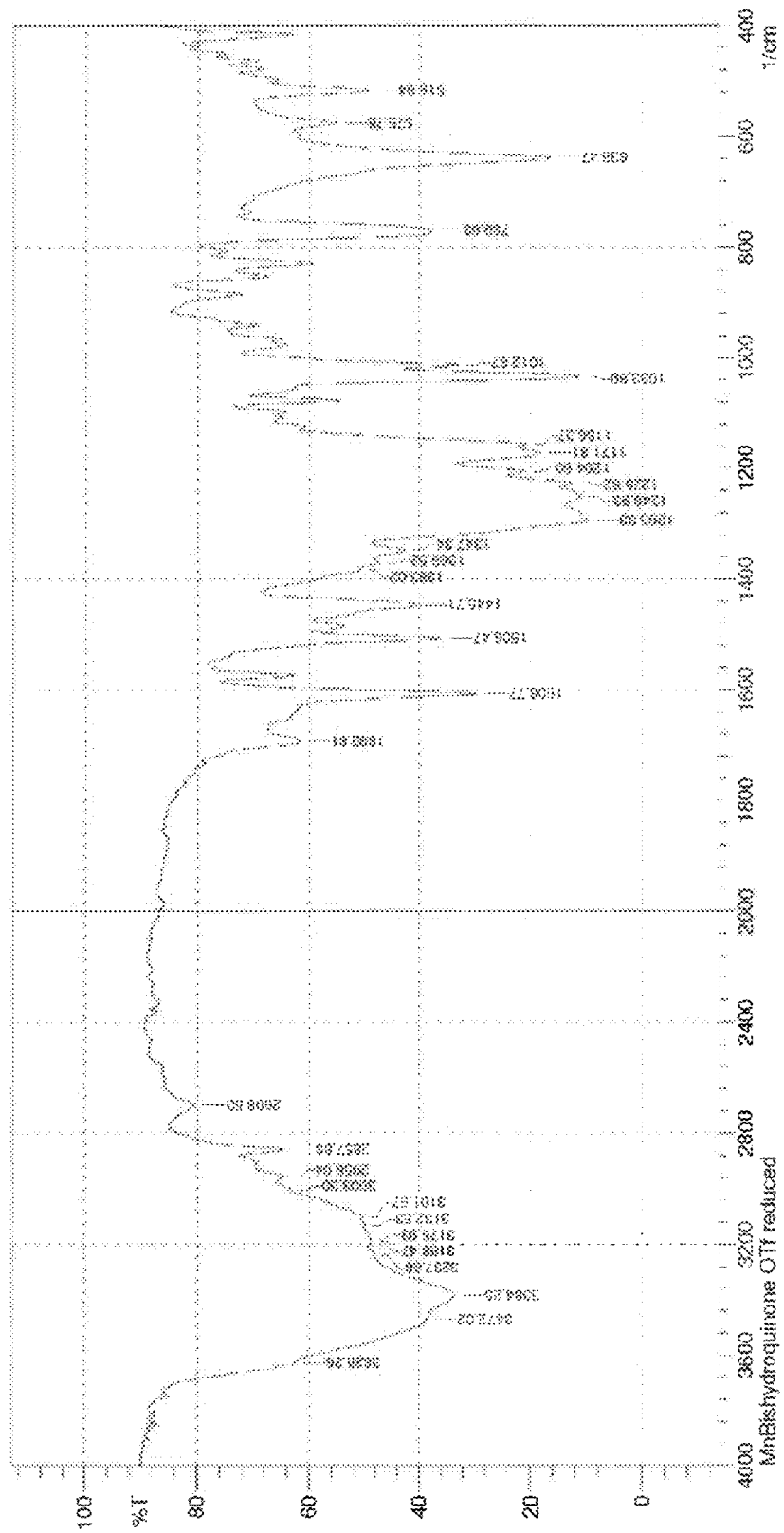
FIG. 6. IR spectrum of 1 (KBr).

The corresponding mass spectrum shows new m/z peaks at 454.22 and 657.10, which correspond to the oxidized form of the ligand (qtp1) and its manganese complex with a triflate anion respectively. The IR spectrum of the solid isolated from the reaction (FIG. 5) has an intense new absorption at 1658 cm$^{-1}$, the energy of which is consistent with a carbonyl stretch for a non-metal-coordinated p-quinone. The reactivity is faster in methanol and water, with the spectroscopic changes occurring in seconds, rather than minutes. For IR analysis, after allowing reaction between 1.0 mM 1 and 4.0 mM H$_2$O$_2$ in MeOH for one hour, the solvents were stripped, yielding the solid used to prepare the sample (KBr). The peak at 1659 cm$^{-1}$ is assigned to a C=O stretch for the quinone formed upon oxidation. For comparison, IR spectrum of 1 is shown in FIG. 6. The 3384 and 3472 cm$^{-1}$ features are assigned to the O—H stretches of the H$_2$qtp1 quinol. The 1607 cm$^{-1}$ feature is assigned to the C—N stretches for the coordinated pyridine rings.

Figure 7:
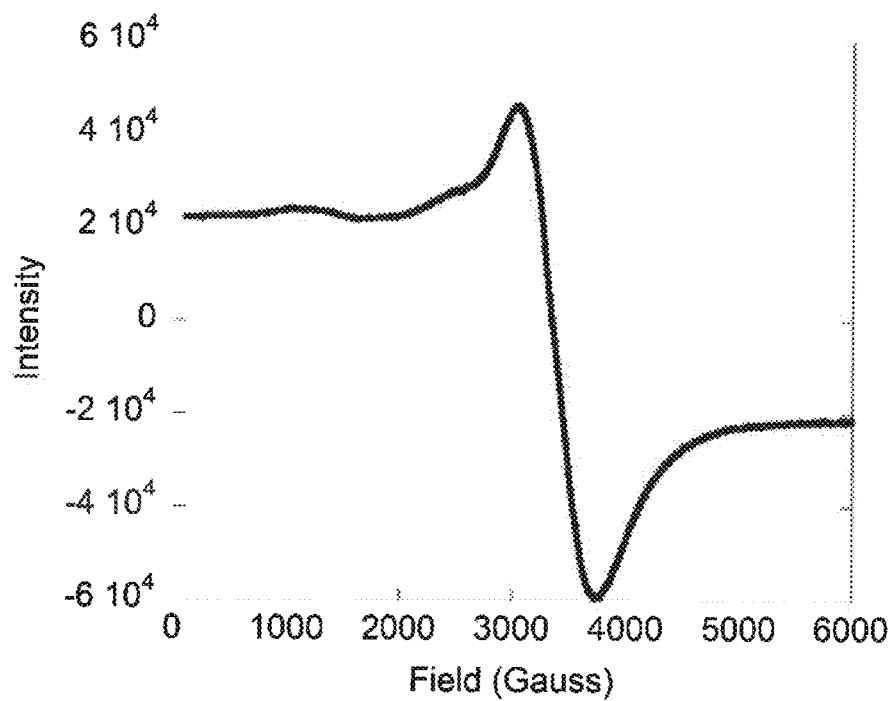
FIG. 7. X-band EPR spectrum of a water solution containing 1.0 mM of 1. The spectrum was acquired at 77 K. $g_{eff}$=1.98.

EPR and UV/vis spectroscopy demonstrate that the oxidation state of manganese does not change after adding H$_2$O$_2$. The EPR spectra of 1 (FIG. 7) and its oxidized product (FIG. 8) are highly similar, with features consistent with high-spin Mn(II). The EPR signal intensity of the Mn(II) in the oxidized product is actually slightly greater than that of an identical concentration of 1. Upon oxidation, no distinct features are observed in the 350-500 nm region where Mn(III)-related LMCT bands are normally observed. The lack of ligand resonance peaks in the NMR of the oxidized material in D$_2$O suggests that the oxidized ligand remains bound to the Mn(II) after the reaction.

Figure 8:
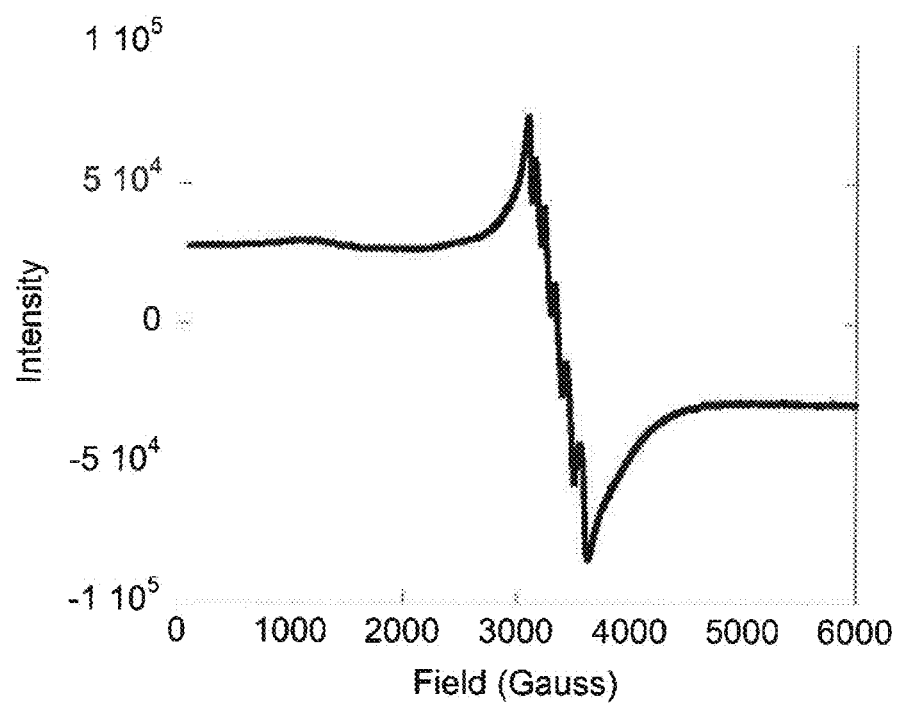
FIG. 8. X-band EPR spectrum of the reaction between 1.0 mM 1 and 10 mM $H_2O_2$ in water. The spectrum was acquired at 77 K. $g_{eff}$=2.00, A=93 Gauss.
Figure 9:
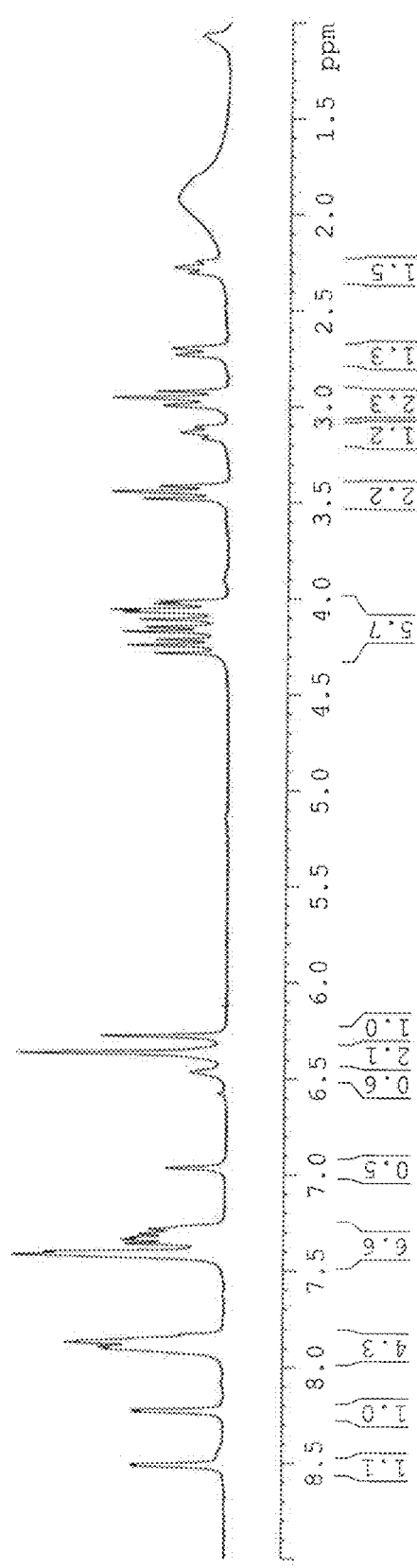
FIG. 9. $^1H$ NMR spectrum of reaction between 10 mM 1 and 4.0 equiv of $H_2O_2$ in $MeCN-d_3$.
Figure 10:
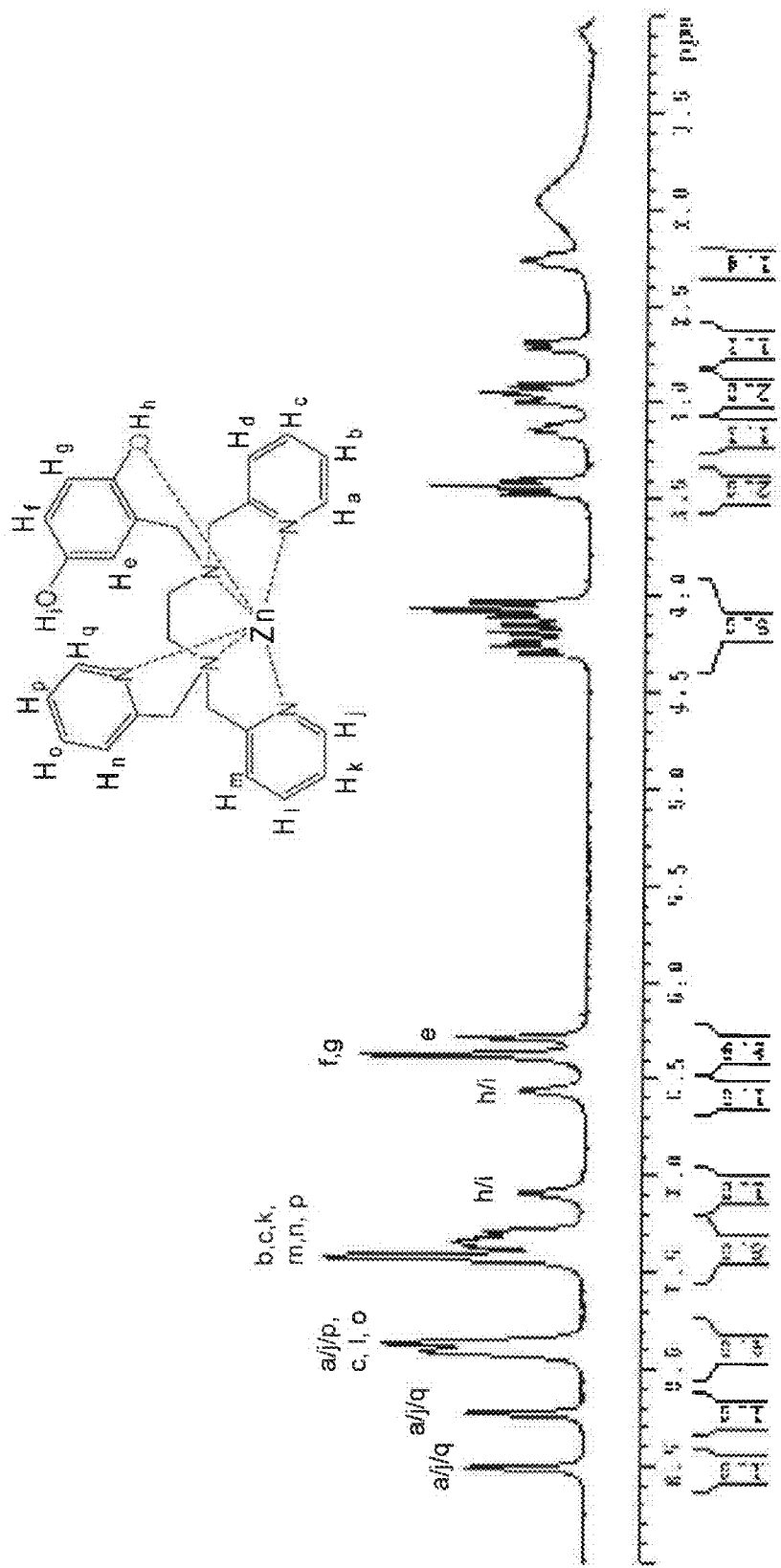
FIG. 10. $^1H$ NMR spectrum of the diamagnetic product from the reaction between 10 mM 1 and 2 equiv of $Zn(ClO_4)_2$ in $MeCN-d_3$.
Figure 11:
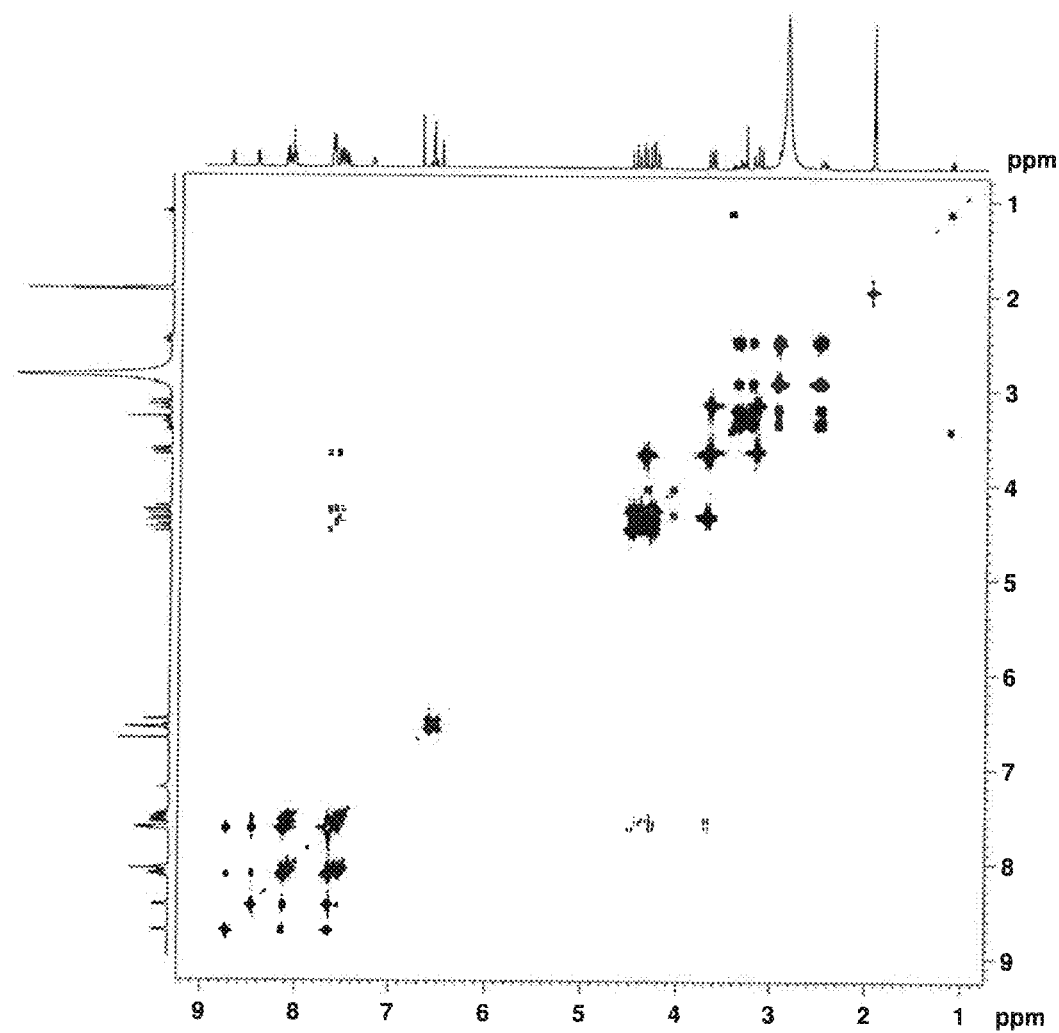
FIG. 11. HQ-COSY NMR of the Zn(II)-$H_2qtp1$ complex.

Analysis of the oxidized product by $^1$H NMR (FIG. 9) indicates that the ligand does not oxidize to completion, even with excess H$_2$O$_2$. The oxidized ligand remains bound to the manganese, as indicated by the absence of diamagnetic peaks. For NMR analysis, after 30 minutes reaction between 10 mM 1 and 4.0 equiv of H$_2$O$_2$ in MeCN-d$_3$, 20 mM of Zn(ClO$_4$)$_2$ was added and the reaction was given 2 hours to equilibrate before $^1$H NMR analysis. The addition of Zn(ClO$_4$)$_2$ to solutions of 1 and its oxidized product leads to rapid metal ion exchange, allowing the visualization of diamagnetic Zn(II)-H$_2$qpt1 (FIG. 10) and Zn(II)-qtp1 adducts. Using HQ-COSY spectroscopy (FIG. 11), we were able to assign two singlet peaks at 6.56 and 7.09 ppm to the hydroxyl protons of H$_2$qtp1 because of the absence of coupling between them. Upon oxidation, these peaks decrease in intensity by approximately 45% but do not vanish completely, as would be anticipated from the complete oxidation of the ligand in the sample. As shown in FIG. 8, the integrated intensities of the quinol peaks at 6.97 and 6.47 ppm are 0.54 and 0.57, suggesting ~55% oxidation of the H$_2$qtp1 ligand. The decrease in these features is invariant and seemingly not correlated to the amount of H$_2$O$_2$ added past a stoichiometric amount. Consequently, we currently believe that the oxidation is reversible and that the mixture of qtp1 and H$_2$qtp1 corresponds to an equilibrium position.

Figure 12:
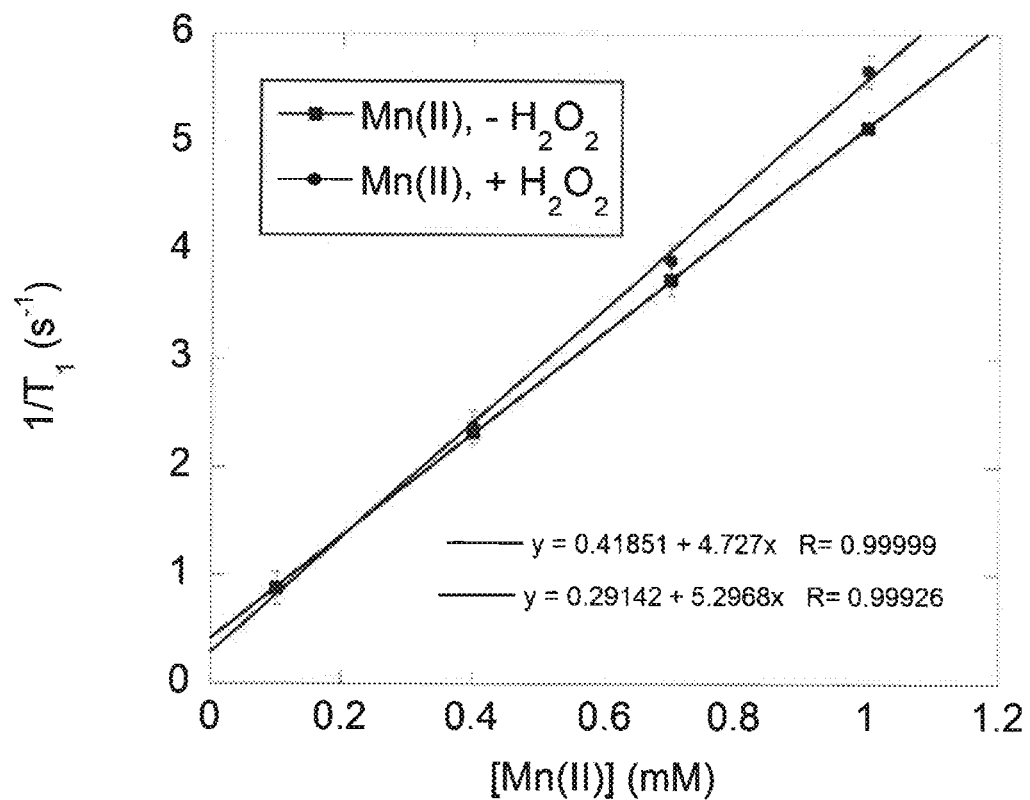
FIG. 12. Plots of $(1/T_1)$ versus Mn(II) concentration for 1 in the presence and absence of 10 mM $H_2O_2$.

For the relaxivity measurements, all samples were run in 298 K aqueous solutions containing 50 mM HEPES buffered to pH 7.00, using a 3 T field provided by a clinical MRI scanner. The data were fit to the indicated linear equations; the y-intercepts were within error of 1/T$_1$ measurements associated with two control samples that contained no Mn(II): (A) 10 mM H$_2$O$_2$ in 50 mM HEPES buffer and (B) pure 50 mM HEPES buffer (both 0.46 s$^{-1}$). A second series of experiments using a different batch of 1 provided r$_1$ values of 4.73 mM$^{-1}$ s$^{-1}$ and 5.30 mM$^{-1}$ s$^{-1}$ for the reduced and oxidized forms of the sensor; these are identical within error to those found for the above experiment. FIG. 12 shows the plots of (1/T$_1$) versus Mn(II) concentration for 1 in the presence and absence of 10 mM H$_2$O$_2$.

The relaxivity of complex 1 in an aqueous solution of 50 mM HEPES buffered to pH 7.00 was found to be 4.73 mM$^{-1}$ s$^{-1}$ (3 T field, 25° C.). This r$_1$ value is higher than both the 4.39 mM$^{-1}$ s$^{-1}$ value for the Mn(II) complex with the related Hptp1 ligand (Hptp1=N-(2-hydroxy-5-methylbenzyl)-N,N', N'-tris(2-pyridinylmethyl)-1,2-ethanediamine) and the 1.73 mM$^{-1}$ s$^{-1}$ value for [Mn(EDTA)(H$_2$O)]$^{2-}$ measured under identical conditions. The enhanced relaxivity of 1 relative to [Mn(Hptp1)(MeCN)](ClO$_4$)$_2$ (2) may be due to additional interactions with outer-sphere water molecules made possible by the presence of the second hydroxyl group on the quinol.

Upon the addition of 10 mM H$_2$O$_2$, the relaxivity per manganese increases from 4.73 mM$^{-1}$ s$^{-1}$ to 5.30 mM$^{-1}$ s$^{-1}$. Although the change is modest, this represents the first instance of a turn-on response by a mononuclear MRI contrast agent to H$_2$O$_2$. We attribute the increase of the relaxivity to the oxidation of the hydroquinone moiety to more weakly coordinating p-benzoquinone. In aqueous solution, water molecules should more readily displace the quinone portion of the ligand, resulting in a transiently greater aquation number, which in turn would increase the r$_1$.[7] This is difficult to ascertain experimentally, given that the sensor is only partially oxidized. The incomplete oxidation also explains the modest r$_1$ response.

That the same amount of ligand oxidation is observed, even with exceedingly high concentrations of H$_2$O$_2$, may suggest that the Mn(II)-qtp1 adduct formed upon oxidation may react with a second equiv. of ROS to return to the reduced state, analogous to a superoxide dismutase (SOD) or catalase enzyme. Evidence does suggest that 1 can catalytically degrade ROSs and behave as an anti-oxidant (vida infra). Complex 1 can be fully oxidized by 2,3-dichloro-5,6-dicyano-1,4-benzoquinone (DDQ). The addition of 1 equiv. of DDQ to a solution of 1 is sufficient to completely oxidize the quinol portion of H$_2$qtp1 to the quinone, as assessed by $^1$H NMR. In the absence of Zn(II), the product is NMR-silent, suggesting that the oxidized ligand remains bound to the Mn(II). The r$_1$ value for the fully oxidized sensor is 5.56 mM$^{-1}$ s$^{-1}$. The addition of 2 mM KO$_2$ to 1 likewise triggers a stronger response (r$_1$=5.52 mM$^{-1}$ s$^{-1}$). The chemical change responsible for the MRI response, however, is not identical to those in the H$_2$O$_2$ and DDQ experiments, as confirmed by UV/vis and MS analysis of the reaction. The addition of 10 mM NaClO to solutions of 1, conversely, does not trigger any changes in the spectroscopic features, and the r$_1$ value (4.82 mM$^{-1}$ s$^{-1}$) remains essentially equal to that of non-oxidized 1. The relaxivity results suggest that an excess of H$_2$O$_2$ oxidizes ~70% of the sensor.

Figure 13:
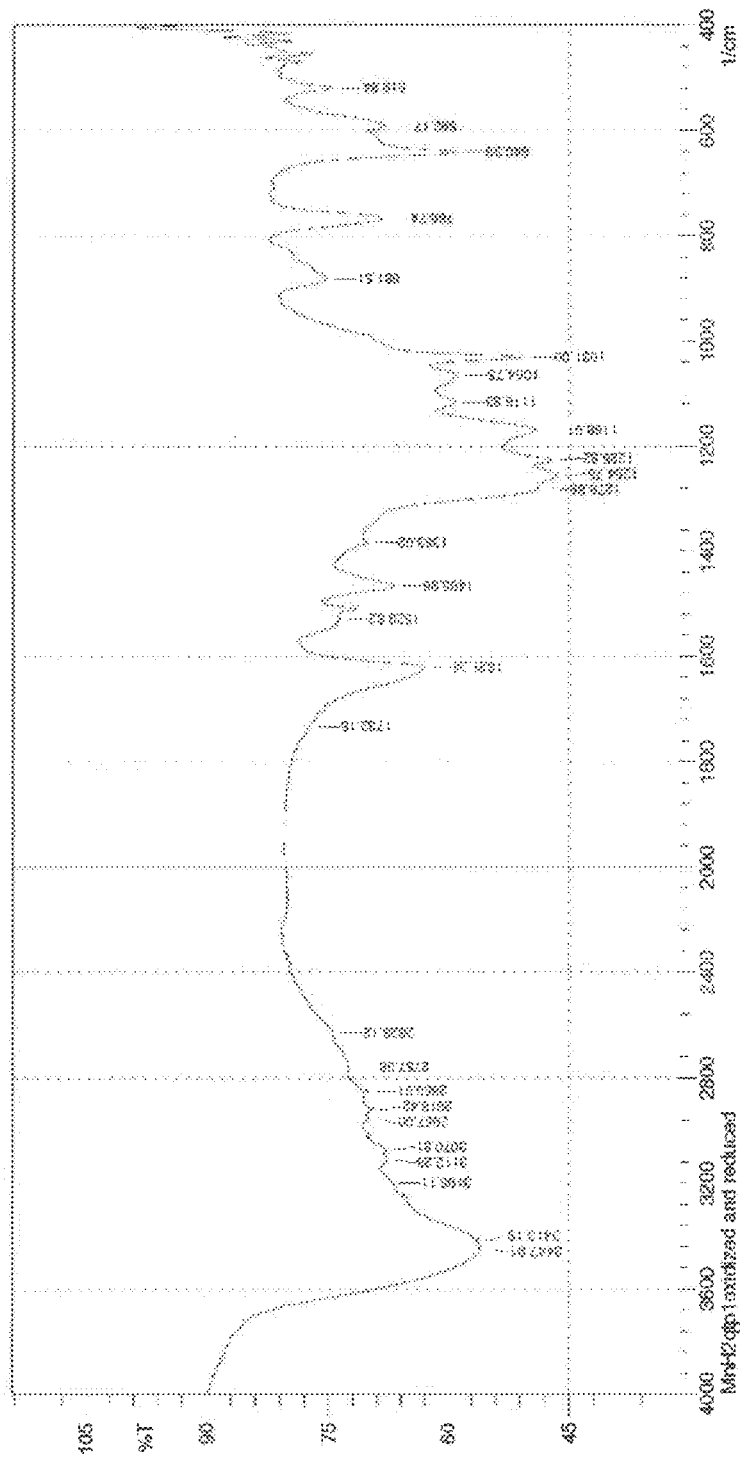
FIG. 13. IR spectrum of the product of the reaction between dithionite and the oxidized form of 1.
Figure 14:
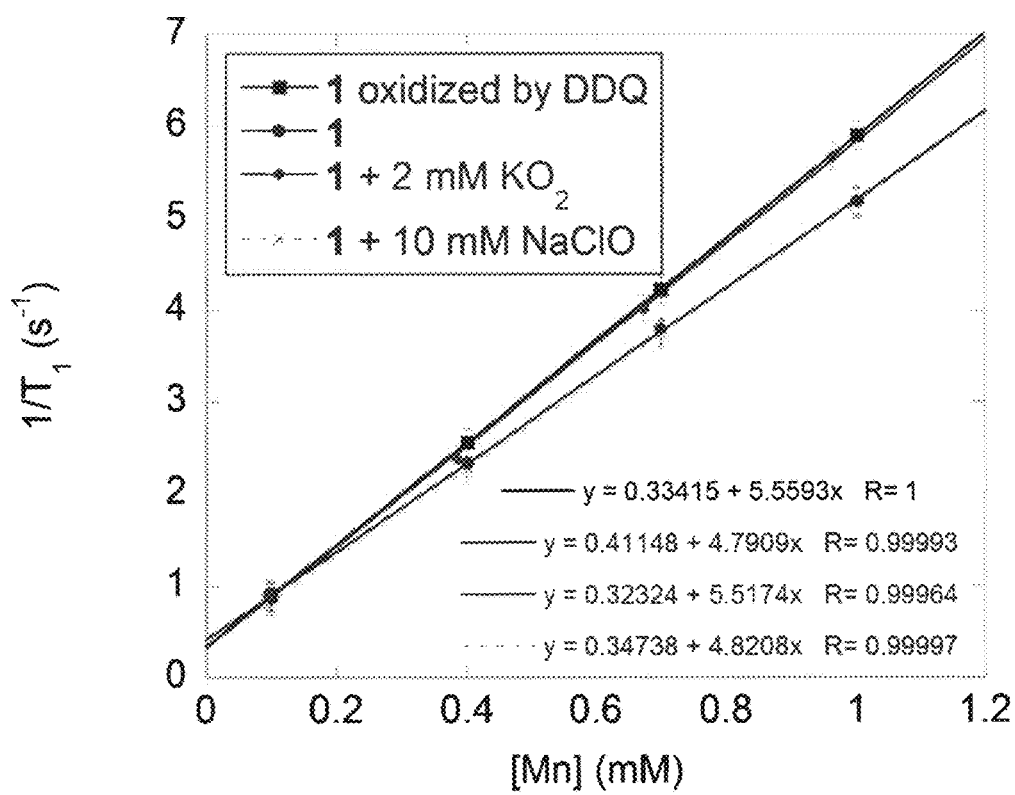
FIG. 14. Plots of $(1/T_1)$ versus Mn(II) concentration for 1 in the presence of various oxidants.

There is limited evidence that the oxidation of the sensor can be reversed by reductants. The addition of sodium dithionite to a H$_2$O$_2$-oxidized solution of 1 in MeOH changes the color from purple to light yellow; the UV/vis spectrum, however, has a much more intense band around 300 nm, which suggests the formation of a different coordination compound. Further analysis suggests that the ligand's oxidation has been reversed. The IR spectrum of the product (FIG. 13) lacks the 1658 cm$^{-1}$ feature indicative of the quinone, and the organic isolated from the reaction mixture appears to be entirely H$_2$qtp1 on the basis of its $^1$H NMR spectrum. For this IR analysis, the sample was prepared by first reacting 10 mM 1 with 40 mM H$_2$O$_2$ for 1 h in MeOH then 40 mM of sodium dithionite for 30 min in MeOH. The solvent was stripped to yield the solid product for the KBr pellet FIG. 14 shows plots of (1/T$_1$) versus Mn(II) concentration for 1 in the presence of various oxidants. All samples were run in 298 K aqueous solutions containing 50 mM HEPES buffered to pH 7.00, using a 3 T field provided by a clinical MRI scanner. The data were fit to the indicated linear equations; the y-intercepts were within error of 1/T$_1$ measurements associated with two control samples that contained no Mn(II): (A) 10 mM H$_2$O$_2$ in 50 mM HEPES buffer and (B) pure 50 mM HEPES buffer (both 0.46 s$^{-1}$). The oxidation of 1 by 2,3-dichloro-5,6-dicyano-1,4-benzoquinone (DDQ) occurred in CH$_2$Cl$_2$. After the reaction occurred, the 2,3-dichloro-5,6-dicyanoquinol product was removed via filtration, the CH$_2$Cl$_2$ was removed, and the sample was dissolve in HEPES buffer for MRI analysis. The other oxidation reactions occurred entirely in HEPES buffer. The addition of KO$_2$ and DDQ resulted in enhanced relaxivity; the addition of NaClO, conversely, did not trigger a MRI response.

Figure 15:
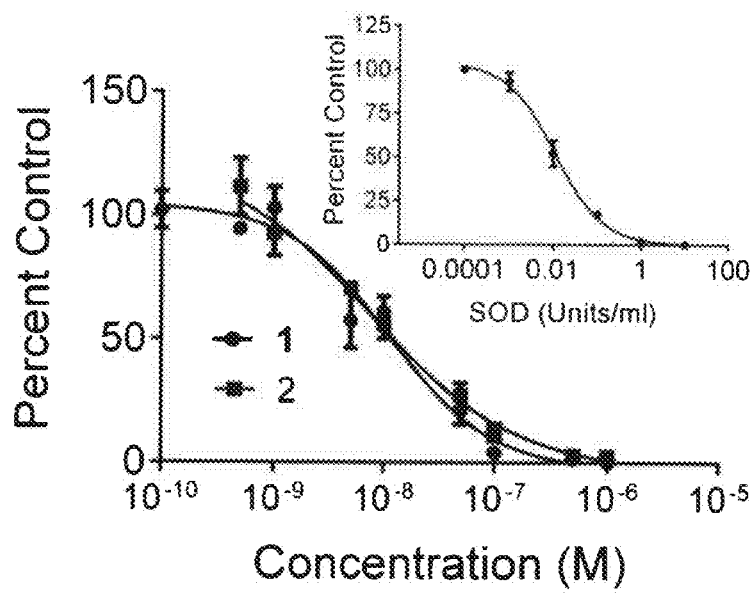
FIG. 15. Superoxide scavenging effects of 1 and $[Mn(Hptp1)(MeCN)](ClO_4)_2$ (2).

The superoxide scavenging effects of 1 and 2 are shown in FIG. 15. Superoxide was generated using a hypoxanthine-xanthine oxidase reaction and detected using the chemiluminescent probe lucigenin. Reactions were carried out in 50 mM Tris-HCl (pH 8.0) containing either 1, 2, or Cu/Zn SOD from bovine erythrocytes (insert). Data for the various concentrations of 1, 2, and SOD are expressed as a percentage of luminescence in the presence of vehicle.

Figure 16:
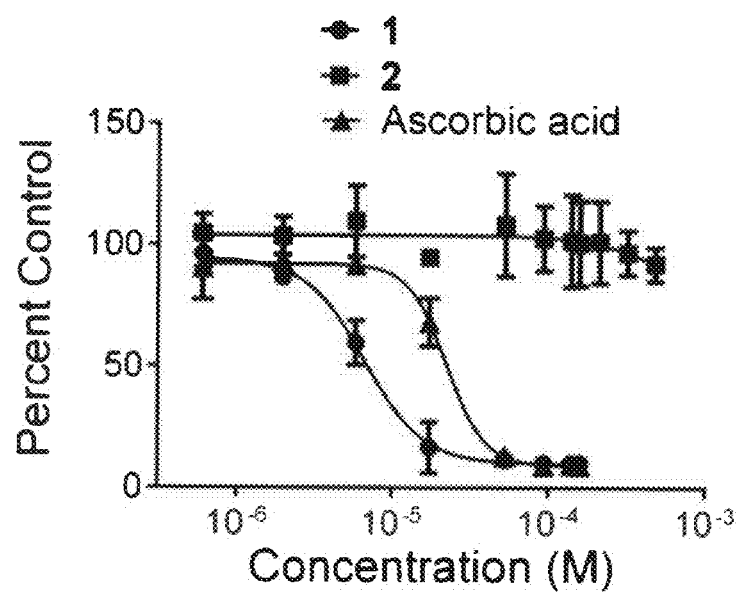
FIG. 16. DPPH free radical scavenging assay of 1, 2, and ascorbic acid.

The anti-oxidant properties of 1 and 2 were also assessed using the DPPH assay (DPPH=2,2-diphenyl-1-picrylhydrazyl radical hydrate), which evaluates the ability of a compound to donate hydrogen atoms to DPPH to yield the corresponding hydrazine. The anti-oxidants were added to DPPH and incubated in the dark for 30 min at room temperature. Spectroscopic measurements were performed at 517 nm. The data were normalized to the absorbance in the presence of vehicle. All experiments were performed in triplicate and repeated twice. Although 1 and 2 are similar with respect to their abilities to intercept O$_2^-$ prior to its reaction with lucigenin, the DPPH assay suggests that 1 is the superior anti-oxidant (FIG. 16). The IC$_{50}$ value for 1 was found to be 6.6 M; by this measure, it bests the well-known anti-oxidant ascorbic acid (IC$_{50}$=22.3 μM). The Hptp1 complex, conversely, fails to reduce DPPH to a noticeable degree.

One concern that has limited the application of redox-active metals in biological imaging is that they can elevate ROS concentrations. The results here demonstrate that the opposite can be true and that there exists the potential to simultaneously image and mitigate the oxidative stress caused by aberrantly high concentrations of ROSs. The cytotoxicities of 1 and 2 have been assessed with H9c2 cells. The cells can tolerate 10 M doses of both compounds for 4 h and a 1.0 M dose of 1 for 24 h. Higher dosages and/or longer incubation times do trigger noticeable cell death.

Example 2

The Synthesis and Characterization of a Mononuclear Mn(II) Complex with the Redox-Active Ligand N,N'-bis(2-pyridinylmethyl)-1,2-ethanediamine ($H_4qtp2$)

Scheme 3

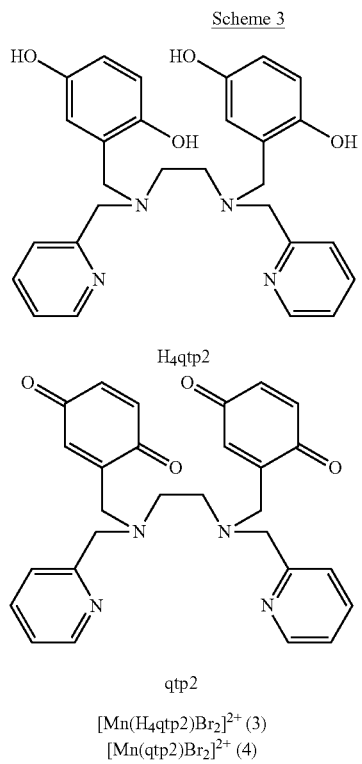

$H_4qtp2$ qtp2

[Mn($H_4qtp2$)Br$_2$]$^{2+}$ (3)
[Mn(qtp2)Br$_2$]$^{2+}$ (4)

The $H_4qtp2$ ligand as shown in Scheme 3 can be synthesized from the readily available N,N'-bis(2-pyridinylmethyl)-1,2-ethanediamine (bispicen) in three steps. The synthesis of $H_4qtp2$ is more challenging than that of the closely related $H_2qtp1$ in that the installation of the second quinol requires the addition of the reagents in two portions and a 40 h reaction time. The product is also hygroscopic and degrades under basic conditions (pH >10). An alternate route in which the two quinol groups were added to 1,2-ethanediamine before the picolyl arms was explored, but it presented drawbacks similar to those for the route proceeding through bispicen in that adding the fourth arm of the ligand required forcing conditions. Further, the quinols needed to be protected before the installation of the picolyl subunits; this and the subsequent deprotection add two synthetic steps. Although $H_4qtp2$ was successfully prepared through this route, the alternative synthesis requires much more time and effort while yielding less of the product.

N-(2,5-Dihydroxybenzyl)-N,N'-bis(2-pyridinylmethyl)-1,2-ethanediamine 2,5-Dihydroxybenzaldehyde (552 mg, 4.00 mmol) and bispicen (1.03 g, 4.25 mmol) were dissolved in 20 mL of ether. The resultant mixture was stirred for 4 h, during which time a solid deposited. The precipitate was collected and washed with a mixture of MeOH/ether (1:9). The isolated and washed aminal (900 mg, 2.48 mmol) was dried and redissolved in 30 mL of MeOH. Trifluoroacetic acid (750 mg, 6.58 mmol) was added to the MeOH solution at 0° C., followed by sodium cyanoborohydride (220 mg, 3.50 mmol). The mixture was stirred at RT for 24 h, at which point the solvent was removed to yield the crude product. The crude was purified by repeated precipitation from MeOH/ether to yield the product as a white solid (568 mg, 63% yield). Typical yields range from 60-70%. $^1$H NMR (400 MHz, CD$_3$OD, 293 K): δ 8.54 (d, J=4.5 Hz, 1H), 8.44 (d, J=4.5 Hz, 1H), 7.80 (m, 2H), 7.38 (m, 4H), 6.58 (m, 3H), 4.25 (s, 2H), 3.92 (s, 2H), 3.71 (s, 2H), 3.31 (m, 4H). $^{13}$C NMR (100 MHz, CD$_3$OD, 293 K): δ 158.42, 151.51, 149.87, 149.22, 148.70, 148.29, 137.48, 137.32, 124.04, 123.55, 122.48, 117.43, 115.94, 115.09, 57.76, 54.23, 49.58, 49.27, 44.64. MS (ESI): Calcd for MH$^+$, 365.1978. Found, 365.2156.

N,N'-Bis(2,5-dihydroxybenzyl)-N,N'-bis(2-pyridinylmethyl)-1,2-ethanediamine ($H_4qtp2$)

N-(2,5-Dihydroxybenzyl)-N, N'-bis(2-pyridinylmethyl)-1,2-ethanediamine (939 mg, 2.57 mmol) and 2,5-dihydroxybenzaldehyde (354 mg, 2.57 mmol) were combined in 60 mL of MeOH. The mixture was cooled to 0° C. with an ice bath. Subsequently, acetic acid (308 mg, 5.14 mmol) was added to the solution, which then stirred for 30 min. After this period, sodium cyanoborohydride (161 mg, 2.57 mmol) was added, and the resultant solution was stirred for an additional 24 h. Second portions of 2,5-dihydroxybenzaldehyde (354 mg, 2.57 mmol), acetic acid (308 mg, 5.14 mmol), and sodium cyanoborohydride (161 mg, 2.57 mmol) were added and allowed react for another 16 h. The solvent was removed under reduced pressure, and the residue was purified by silica gel chromatography (15:1 EtOAc/MeOH eluent, product $R_f$=0.3) to yield the ligand as a white powder (800 mg, 64% yield). Typical yields range from 45-65%. $^1$H NMR (400 MHz, CD$_3$OD, 293 K): δ 8.46 (qd, J=5.2 Hz, 1.6 Hz, 0.8 Hz, 2H), 7.75 (dt, J=9.6 Hz, 2.0 Hz, 2H), 7.31 (m, 4H), 6.58 (d, J=1.6 Hz, 4H), 6.55 (m, 2H), 3.81 (s, 4H), 3.68 (s, 4H), 2.87 (s, 4H). $^{13}$C NMR (100 MHz, CD$_3$CN, 293 K): δ 150.08, 149.36, 148.97, 137.07, 123.56, 122.59, 117.14, 116.47, 115.47, 58.27, 56.15, 49.82. MS (ESI): Calcd for MH$^+$, 487.2346. Found, 487.2277.

cis-Dibromo(N,N'-bis(2,5-dihydroxybenzyl)-N,N'-bis(2-pyridinylmethyl)-1,2-ethanediamine)manganese(II) ([Mn($H_4qtp2$)Br$_2$], 3)

The $H_4qtp2$ ligand (500 mg, 1.03 mmol) and MnBr$_2$ (221 mg, 1.03 mmol) were dissolved in 5 mL of MeCN in a dry and anaerobic glovebox. The solution was allowed to stir at 60° C. for 16 h; over this time, a white precipitate deposited. The solution was filtered, and the filtrate was washed with MeCN to yield the product as a white powder (550 mg, 71% yield). Typical yields range from 70-85%. Crystals suitable for single crystal X-ray diffraction were grown by slow evaporation from a saturated solution of the crude in MeOH. MS (ESI): Calcd for [Mn(L-H)]$^+$, 540.1569. Found, 540.1564. Solid-state magnetic susceptibility (294 K): $\mu_{eff}$=5.6$\mu_B$. Optical spectroscopy (MeOH): 302 nm (5420 M$^{-1}$ cm$^{-1}$). IR (KBr, cm$^{-1}$): 3405 (s), 1604 (m), 1511 (s), 1446 (s), 1358 (w), 1341 (w), 1310 (w), 1210 (m), 1191 (s), 1156 (w), 1066 (w), 1049 (w), 1016 (w), 948 (w), 934 (w), 810 (m), 754 (m). Elemental Analysis (powder): Calcd for $C_{29}H_{34}N_4MnO_4Br_2$*$CH_3CN$: C, 48.54%; H, 4.48%; N, 9.43%. Found: C, 48.43%; H, 4.58%; N, 9.72%.

cis-Dibromo(N,N'-bis(2,5-benzoquinone)-N,N'-bis (2-pyridinylmethyl)-1,2-ethanediamine)manganese (II) ([Mn(qtp2)Br$_2$], 4)

Complex 3 (60 mg, 0.080 mmol) was dissolved in 1 mL of $CH_2Cl_2$ under $N_2$. 2,3-Dichloro-5,6-dicyano-p-benzoquinone (DDQ, 37 mg, 0.16 mmol) was dissolved in 5 mL of $CH_2Cl_2$. The resultant solution was added to 3 dropwise. The mixture was allowed to stir overnight, at which point it was filtered through celite. Slow evaporation of the solvent from the filtrate deposited red crystals that were suitable for X-ray diffraction. These were collected and washed with cold $CH_2Cl_2$ to yield 9.8 mg of product (16%). Typical yields range from 10-15%. Optical spectroscopy (MeOH): 249 nm (4140 $M^{-1}$ $cm^{-1}$). IR (KBr, $cm^{-1}$): 3434 (s), 3234 (w), 2963 (m), 2925 (w), 2855 (w), 1657 (C=O, s), 1602 (m), 1443 (m), 1262 (m), 1102 (m), 1050 (m), 1015 (m), 810 (m). Elemental Analysis: Calcd for $C_{28}H_{26}N_4MnO_4Br_2 \cdot 0.5H_2O$: C, 47.62%; H, 3.85%; N, 7.93%. Found: C, 47.70%; H, 3.97%; N, 7.84%.

The H$_4$qtp2 ligand appears to bind to Mn(II) readily, but we were unable to obtain a crystalline product from reactions between H$_4$qtp2 and either Mn(OTf)$_2$ or Mn(ClO$_4$)$_2$. Consequently, MnBr$_2$ was selected as the salt for the H$_4$qtp2 complex for two reasons. First, the solubility of this salt in MeCN facilitated the product's isolation and purification. Second, bromide does not bind avidly to Mn(II),[8] and we anticipated that this anion would be readily displaced by O-donors, such as quinols, quinolates, and water molecules, upon solvation. The complex [Mn(H$_4$qtp2)Br$_2$] (3) was prepared in moderately high yield by mixing the ligand with MnBr$_2$ in 60° C. MeCN. Upon standing, complex 3 precipitates from the reaction mixture.

The Mn(II) complex with the fully oxidized ligand (qtp2) was prepared by oxidizing 3 with 2,3-dichloro-5,6-dicyano-p-benzoquinone (DDQ) in $CH_2Cl_2$. DDQ was previously noted for its ability to cleanly and fully oxidize the quinol subunit in the related 1. Crystals of [Mn(qtp2)Br$_2$] (4) can be obtained after approximately 20 h, albeit in relatively low yield. Regrettably, the solubility of crystalline 4 is poor in pure H$_2$O; this and the poor yield (~15%) limit our ability to both characterize the complex and use it as a standard for reactions involving 4 and H$_2$O$_2$.

Structural Characterization

Figure 17:
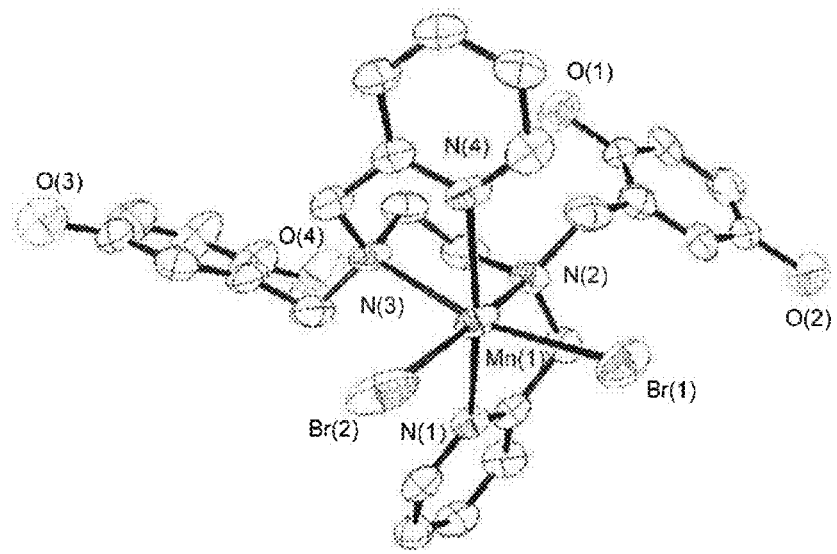
FIG. 17. Structure of $[Mn(H_4qtp2)Br_2]$ (3).

Needle-shaped crystals of 3 were grown from saturated solutions of the complex in MeOH via slow evaporation of the solvent (Table 3). The Mn(II) center is six-coordinate, with the two bromides bound in a cis fashion and the four nitrogen donors provided by the H$_4$qtp2 ligand binding in a cis-α conformation which places the two pyridine groups trans to each other (FIG. 17). In FIG. 17, all hydrogen atoms and solvent molecules are omitted for clarity. All thermal ellipsoids are drawn at 50% probability. Neither quinol binds directly to the Mn(II) in the crystal. The Mn—N and Mn—Br bond distances measured for 3 are typical for a hexacoordinate high-spin Mn(II) complex (Table 4). The oxidation number and spin-state assignments derived from the metrical parameters are corroborated by solid-state magnetic susceptibility measurements ($\mu_{eff}$=5.6$\mu_B$). The Mn—N bonds to the pyridine rings are shorter than those to the tertiary amines; both pairs of bond distances are similar to those measured for other MnN$_4$X$_2$ cores with amine and pyridine N-donors. The C—O bond distances average 1.37 Å, indicating that the quinols remain both fully reduced and fully protonated.

TABLE 3

Selected crystallographic data for 3 and 4

| Parameter | [Mn(H$_4$qtp2)Br$_2$] | [Mn(qtp2)Br$_2$] (4) |
|---|---|---|
| Formula | C$_{30}$H$_{33}$Br$_2$MnN$_5$O$_5$ | C$_{28}$H$_{26}$Br$_2$MnN$_4$O$_8$ |
| MW | 758.35 | 761.27 |
| Crystal system | Monoclinic | Cubic |
| Space group | P$_{21/n}$ | Ia3d |
| a (Å) | 9.6411(2) | 34.991(2) |
| b (Å) | 21.9027(6) | 34.991(2) |
| c (Å) | 15.3507(4) | 34.991(2) |
| α (deg) | 90 | 90 |
| β (deg) | 99.881(1) | 90 |
| γ (deg) | 90 | 90 |
| V (Å$^3$) | 3193.46(14) | 42842(9) |
| Z | 4 | 48 |
| Cryst color | Light orange | Light red |
| T | 180 | 180 |
| Reflns collected | 31999 | 38465 |
| Unique reflns | 3031 | 1350 |
| R1 (F, I > 2σ(I)) | 0.0566 | 0.0578 |
| wR2 (F$^2$, all) | 0.1104 | 0.2042 |

R1 = Σ | |F$_o$| − |F$_c$| |/Σ |F$_o$|; wR2 = [Σw(F$_o^2$ − F$_c^2$)$^2$/Σw(F$_o^2$)$^2$]$^{1/2}$.

TABLE 4

Selected bond lengths (Å) for complexes 3 and 4

| Complex | 2 | 3 |
|---|---|---|
| Mn—N(1) | 2.241(5) | 2.252(8) |
| Mn—N(2) | 2.338(6) | 2.395(8) |
| Mn—N(3) | 2.346(6) | 2.395(8) |
| Mn—N(4) | 2.272(5) | 2.252(8) |
| Mn—Br(1) | 2.6244(14) | 2.5971(19) |
| Mn—Br(2) | 2.6134(15) | 2.5971(19) |
| O(1)—C(13) | 1.363(8) | 1.226(15) |
| O(2)—C(10) | 1.383(10) | 1.242(16) |
| O(3)—C(22) | 1.395(11) | 1.242(16) |
| O(4)—C(19) | 1.334(10) | 1.226(15) |

N(1) and N(4) correspond to pyridine nitrogens; N(2) and N(3) correspond to amine nitrogens. The atoms in 4 have been relabeled in order to facilitate comparison to those in the structure of 3.

Figure 18:
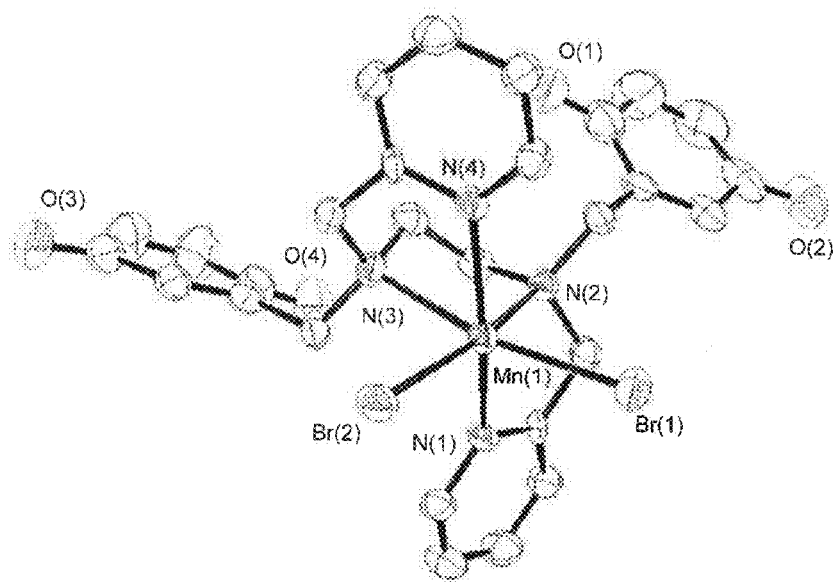
FIG. 18. Structure of $[Mn(qtp2)Br_2]$ (4).

The product of DDQ oxidation, 4, was also crystallized and structurally characterized (FIG. 18). In FIG. 18, all hydrogen atoms and solvent molecules are omitted for clarity and all thermal ellipsoids are drawn at 50% probability. The atoms have been relabeled from those in the CIF file in order to facilitate comparison to the structure of 3. The metal center remains hexacoordinate and retains the same N$_4$Br$_2$ coordination sphere upon oxidation. The C—O bonds shorten to 1.23 Å (Table 4), confirming the oxidation of both quinols to para-quinones. Upon oxidation, the bonds between the Mn(II) and the amine N atoms lengthen slightly while those between the Mn(II) and the Br atoms slightly contract. Although the crystals are colored, the oxidation state of the manganese remains +2, as best structurally evidenced by the Mn—N and Mn—Br bond distances. None of the bonds are significantly elongated or shortened relative to their counterparts in 3. The absence of Jahn-Teller distortions further supports the assignment of the +2 oxidation state for the manganese atom.

Spectroscopic and Solution Characterization

Figure 19:
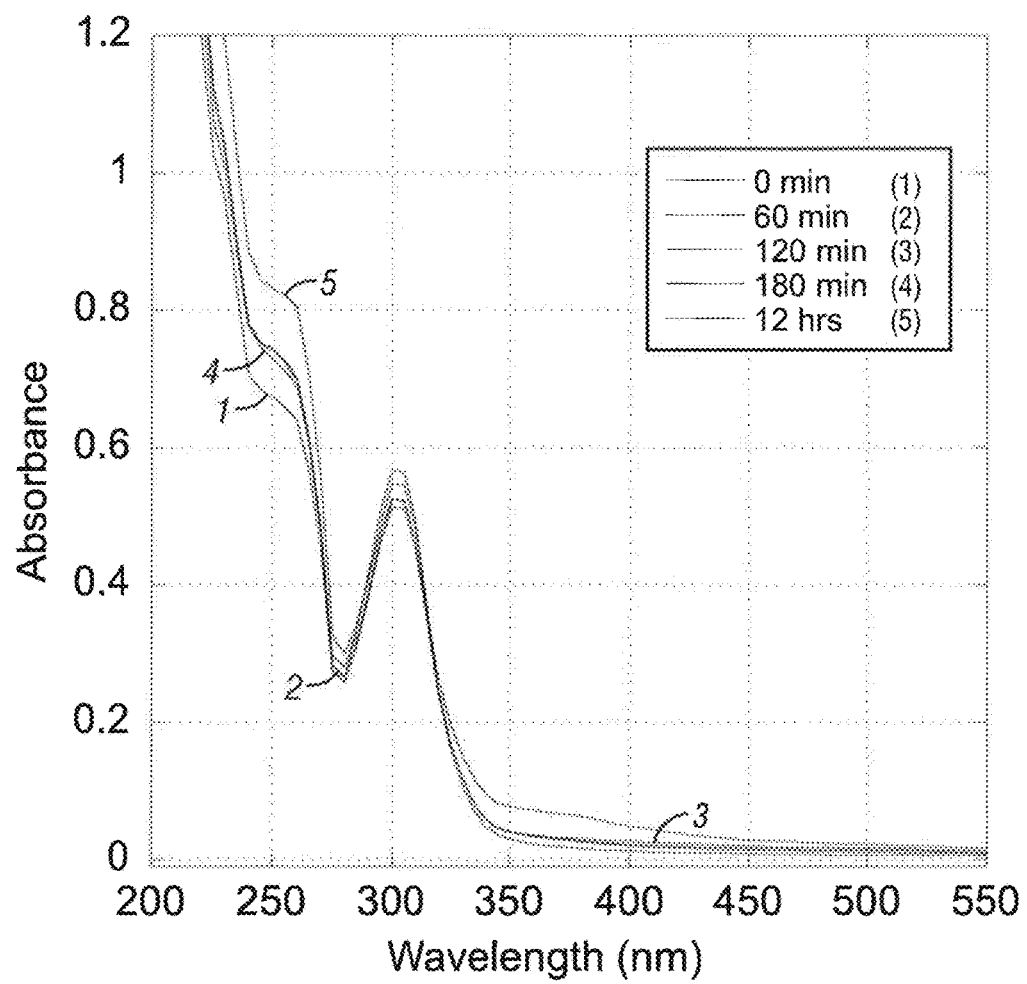
FIG. 19. UV/Vis spectra depicting the stability of a 0.10 mM solution of $[Mn(H_4qtp2)Br_2]$(3) in MeOH to air.
Figure 20:
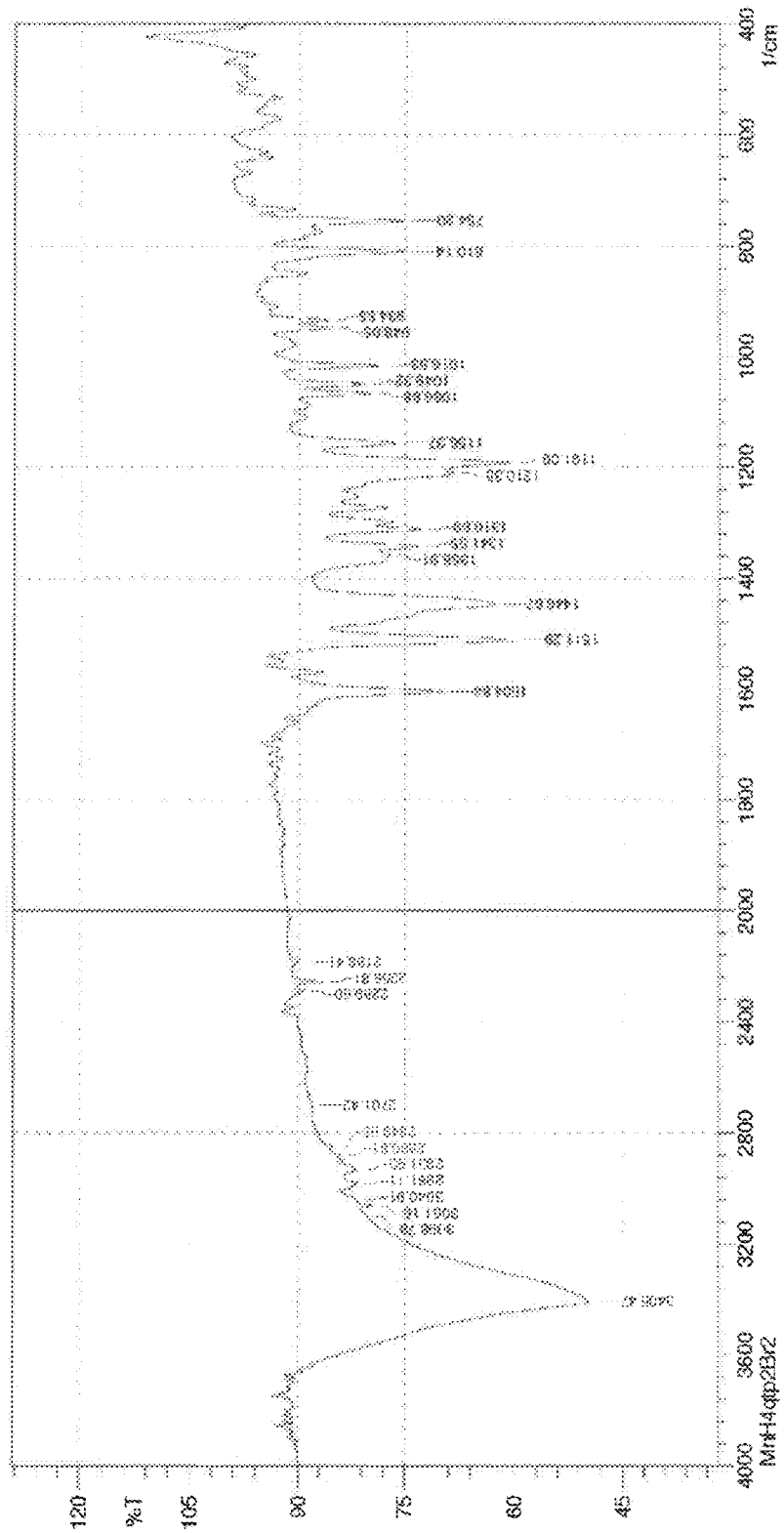
FIG. 20. IR spectrum of 3 (KBr).
Figure 21:
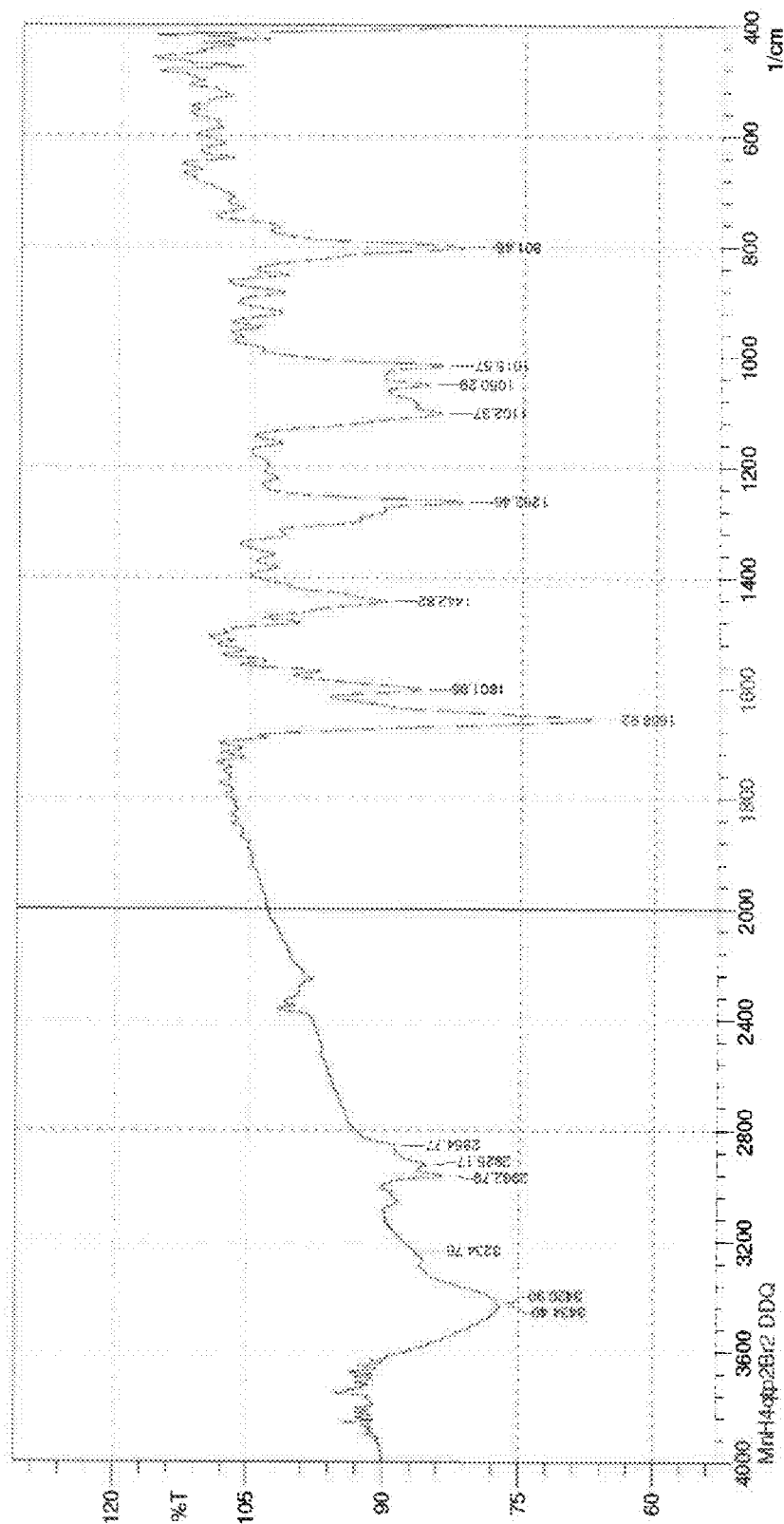
FIG. 21. IR spectrum of 4 (KBr).

The oxidation state of H$_4$qtp2 can be readily monitored by UV/vis and infrared (IR) spectroscopy. The reaction was scanned at 0, 1, 2, 3, and 12 h. The band at 302 nm is characteristic of quinol functional groups. In MeOH, complex 3 displays a moderately intense UV/vis absorbance band at 302 nm under air (FIG. 19). This feature can be assigned to an electronic excitation within the quinols. As expected, the oxidized product 4 lacks this UV/vis band. The C=O stretches associated with the para-quinones are anticipated to appear between 1600 and 1800 cm$^{-1}$. The IR spectrum of 3 has a band at 1605 cm$^{-1}$, which has a frequency and intensity typical of a C—N stretch for a pyridine bound to a divalent metal, but otherwise lacks features in this range (FIG. 20). The 3405 cm$^{-1}$ feature is assigned to the O—H stretches associated with the quinol groups of the H$_4$qtp2 ligand. The 1605 cm$^{-1}$ feature is assigned to the C—N stretches associated with the metal-coordinated pyridine rings. The IR spectrum of 4, conversely, has a strong band at 1657 cm$^{-1}$, consistent with the presence of quinone C=O bonds (FIG. 21).

Figure 22:
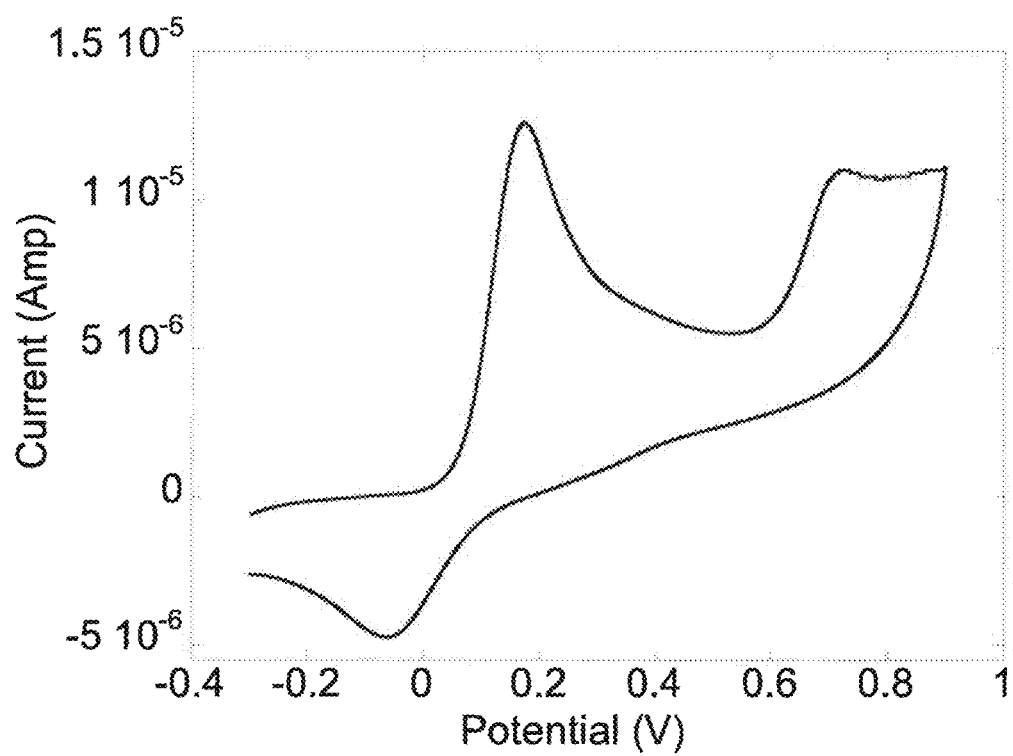
FIG. 22. Cyclic voltammetry of 1.0 mM 3 in 0.10 M phosphate buffer ($NaH_2PO_4/Na_2HPO_4$, pH=7.2).

Complex 3 was studied by cyclic voltammetry (CV) in water containing 50 mM phosphate to buffer the solution to pH 7.2. A redox feature with $E_{1/2}$ of 60 mV vs. Ag/AgCl (295 mV vs. NHE) is observed (FIG. 22).

Similar redox processes were found for both 1 and a Zn(II)-H$_2$qtp1 complex, leading us to assign the 60 mV redox event to the oxidation of the ligand, rather than the manganese. The separation between the anodic and cathodic peaks (ΔE) for this feature is 230 mV; this is much less reversible than its analog in the CV of 1 (75 mV). A second and entirely irreversible redox event at 725 mV (960 mV vs NHE) is tentatively assigned to the oxidation of Mn(II) to Mn(III). For this analysis, the scan rate was 100 mV/s. For the quasi-reversible feature: $E_{1/2}$=57 mV vs. Ag/AgCl, ΔE=232 mV. An irreversible feature with Epc=725 mV is also observed.

Potentiometric pH Titrations

Small molecule sensors are notoriously sensitive to changes in their molecular structure; seemingly minor changes can either disrupt the desired response or introduce side reactivity that precludes their use. When complex 3 is dissolved in D$_2$O, $^1$H NMR spectroscopy detects no resonances aside from that corresponding to the solvent. The $^1$H NMR data are therefore inconsistent with the presence of either the free H$_4$qtp2 ligand or potential decomposition products. The speciation in water was more rigorously probed with potentiometric pH titrations. Analysis of the H$_4$qtp2 ligand in 100 mM KCl solution found two distinct ionization events between pH 2.5 and 9.0. The instability of the ligand under more basic conditions precluded us from obtaining reliable data above pH 9.0, but we were able to find the same two ionization events by titrating basic solutions of H$_4$qtp2 with HCl. Analysis of the equivalence points suggested p$K_a$ values of 4.47 and 7.18 which were subsequently confirmed with a Hyperquad model. The 4.47 and 7.18 values likely correspond to the protonation/deprotonation of a pyridine ring and one of the tertiary amines, respectively (Scheme 4); similar values have been found for analogous protonation events for pyridylamine ligands. The quinolic protons likely deprotonate at higher pH values (p$K_a$~10), but we were unable to obtain the high pH data necessary to confirm this.

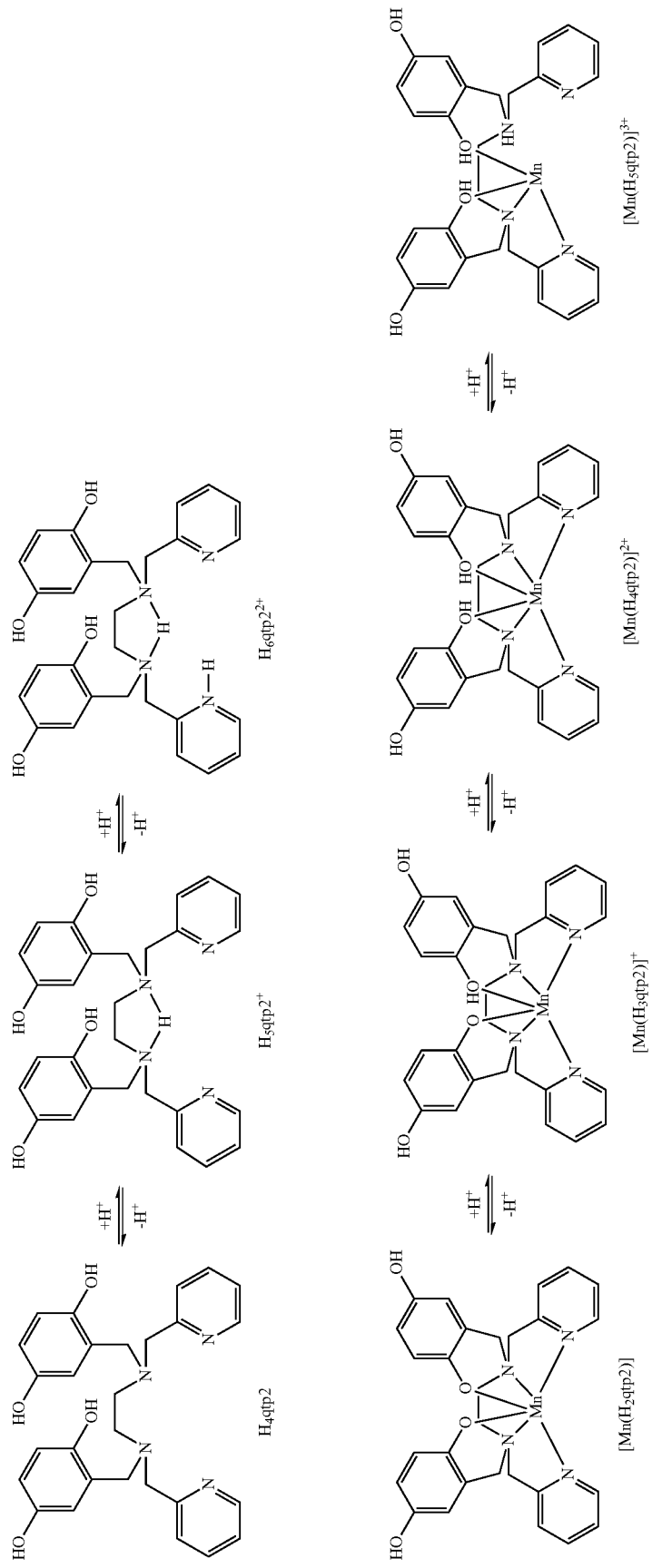
Scheme 4. Proposed protonation states of the reduced ligands and Mn(II) complexes.

Complex 3 displays a pH response that is distinct from that of H₄qtp2. Upon titration of an acidic solution of 3 with KOH, we observed that the solution began to become cloudy at approximately pH 8.0, which again limited our ability to obtain reliable high pH data. This also prevented us from titrating basic solutions of 3 with HCl, but we were able to reproduce the events observed in the KOH titration three times. The data were fit to a model containing the protonated forms of the free ligand and four Mn(II) complexes with the ligand in various protonation states: [Mn(H₂qtp2)], [Mn(H₃qtp2)]⁺, [Mn(H₄qtp2)]²⁺, and [Mn(H₄qtp2)]³⁺ (Scheme 4). The Mn(II) ions in these species could potentially be coordinated to water molecules, but we were unable to obtain complementary data to either support or refute this. Based on the heptacoordination observed for the related 1 and 2, we speculate that q=1 at pH 7.0. Table 5 lists the calculated log(3) values for each species in the model; Table 6 provides the $pK_a$ values that can be derived thereof. The $pK_a$ values at 7.14 and 5.82 have been assigned to the protonation of metal-bound quinolates. Although the free ligand displays an ionization event with $pK_a$ of 7.18, the data for 3 are inconsistent with a single ionization event. Since the 7.14 and 5.82 values are substantially below the $pK_a$ values associated with free quinols, we propose that the relevant Mn(II) species around pH 7 are bound to O-donors from the quinol/quinolate ligands. Water molecules bound to divalent metals typically have $pK_a$ values close to 10. Phenols coordinated to divalent metals, conversely, have $pK_a$ values in the 6-8 range unless they have been derivatized with an electron-withdrawing substituent.

Figure 23A:
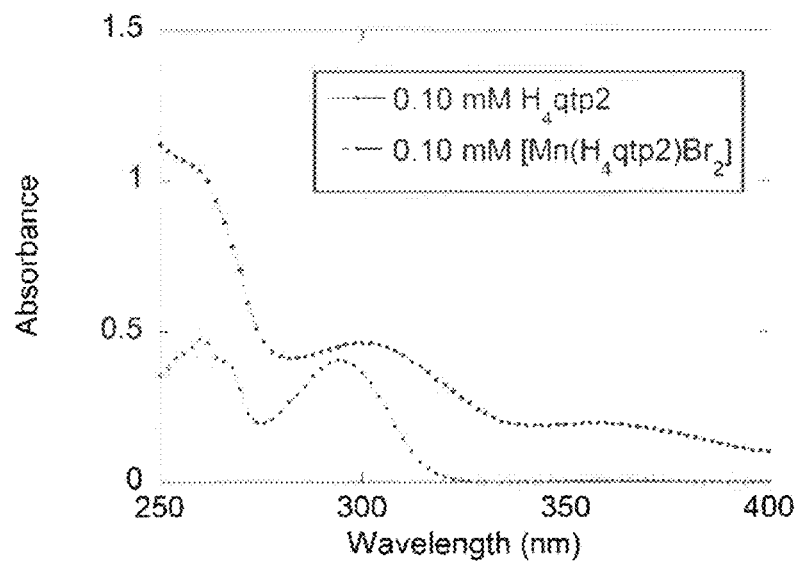
FIG. 23A. UV/vis data for $H_4qtp2$ and 3 in aqueous solutions at pH 7.
Figure 23B:
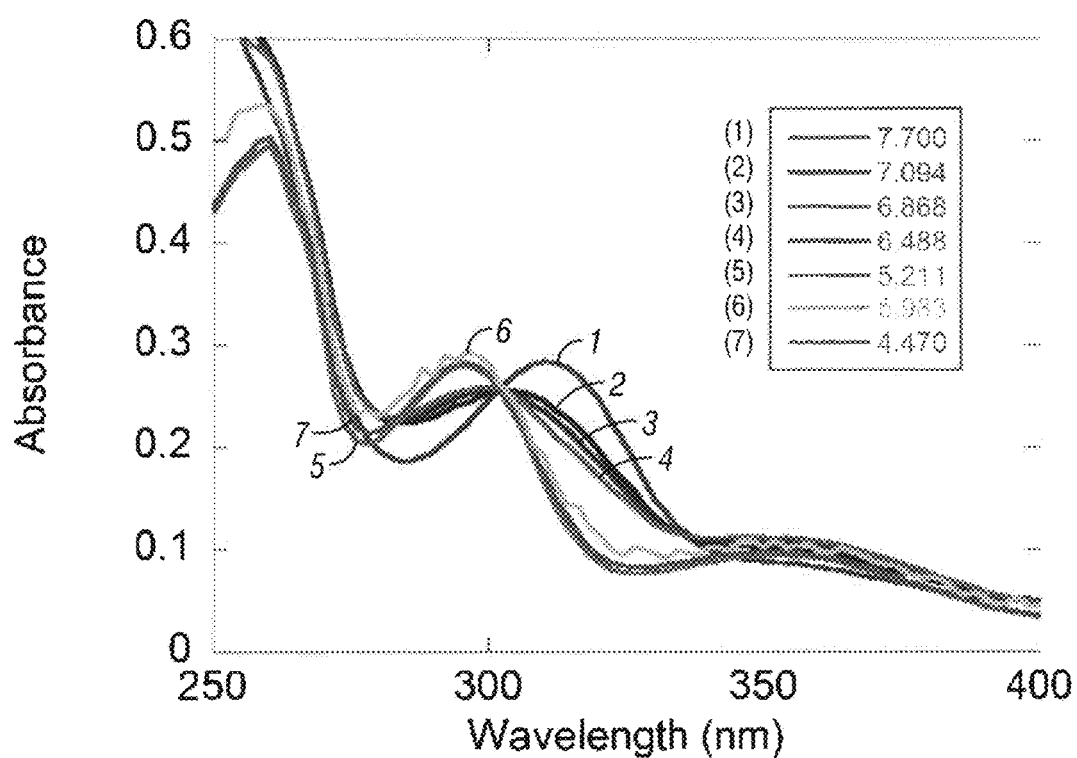
FIG. 23B. UV/vis data for 3 at various pH values.

The protonation state assignments for the quinols are supported by UV/vis data collected for free H₄qtp2 and 3 in aqueous solutions. All spectra were obtained at 298 K under air using a 1.0 cm pathlength cuvette. A) UV/vis spectra of 0.10 mM solutions of H₄qtp2 and 3 in aqueous solutions containing 50 mM HEPES buffered to pH 7.00. B) UV/vis spectra of a 0.05 mM solution of 3 in water adjusted to various pH values between 7.700 and 4.470 through the addition of either KOH or HCl. In 50 mM HEPES solutions buffered to pH 7.00, H₄qtp2 displays absorbance peaks at 260 nm and 294 nm; conversely, complex 3 has maxima at 300 nm and 362 nm (FIG. 23A). The free ligand, but not 3, is anticipated to contain fully protonated quinols at this pH. At pH 7.700, complex 3 has a sharp band at 311 nm (FIG. 23B). Upon titrating this solution with HCl, this band gradually shifts to 295 nm, the energy of which is consistent with the presence of quinols rather than quinolates. No substantial changes to the 295 nm feature occur below pH 5.983; at this point the metal-bound quinols are anticipated to be approximately 75% protonated. Similar pH-dependent spectrophotometric changes were recently found for a Mn(II) complex with a phenol-containing ligand.

The [Mn(H₅qtp2)]³⁺ species observed under acidic conditions likely contains a proton localized on one of the amines; the 5.53 $pK_a$ value is high for a pyridine. The protonation of one of the secondary amines would be anticipated to greatly destabilize the Mn(II) complex. We had hoped to obtain a $K_{eq}$ for the [Mn(H₂qtp2)] complex, but the instability of the ligand under basic conditions precluded us from measuring the log(3) for H₂qtp2²⁻ that is required for this calculation.

Figure 24:
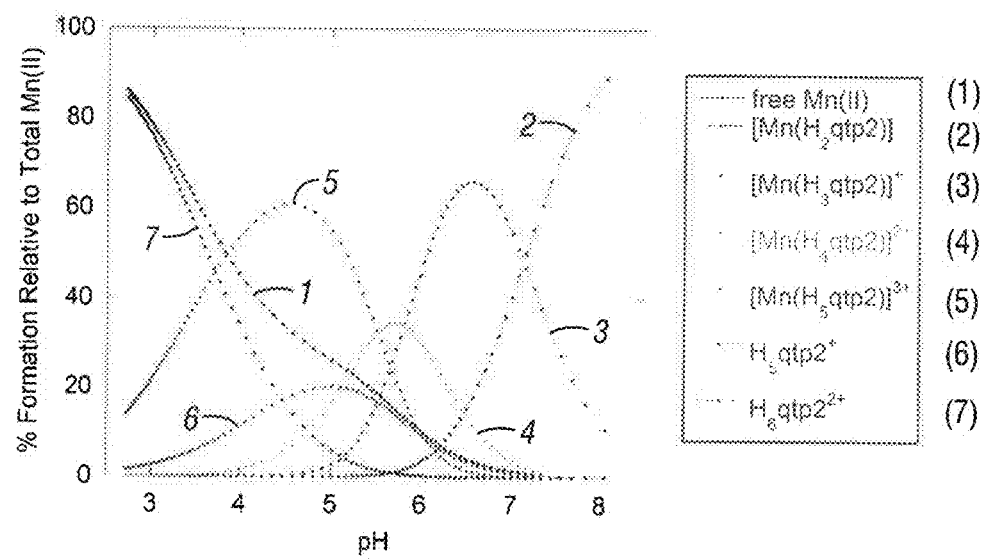
FIG. 24. Species distribution for solutions of 3 in water containing 100 mM KCl as a function of pH at 25° C. and [3]=1 mM.

FIG. 24 shows the percent formation of each Mn(II) species as a function of pH.

Analysis of the modeled data yields a pMn of 5.36 at pH 7.4. A nearly identical pMn value was recently found for our Hptp1 system, which features a ligand with a para-methylphenol, rather than a quinol, moiety. At pH 7.4, the most prevalent species are [Mn(H₂qtp2)] (66.2%) and [Mn(H₃qtp2)]⁺ (32.5%), which feature one and two quinolate O-donors respectively. Over 99% of the manganese is bound by some form of the H₄qtp2 ligand. At pH 7.0, [Mn(H₃qtp2)]⁺ becomes the major species (54.6%), although there is still a substantial amount of [Mn(H₂qtp2)] (40.3%). The percentage of free Mn(II) increases to 1.4%. As the pH drops below 7.0, the N-donors on the ligand become protonated with concomitant release of Mn(II).

TABLE 5

Parameters for the Hyperquad model.

| Species | Mn²⁺ | H₄qtp2 | H⁺ | log(β) | Derived Values |
|---|---|---|---|---|---|
| H₄qtp2 | 0 | 1 | 0 | 0.00 | |
| H₅qtp2⁺ | 0 | 1 | 1 | 7.18 (±0.03) | $pK_{L2}$ = 7.18 (±0.03)[a] |
| H₆qtp2²⁺ | 0 | 1 | 2 | 11.65 (±0.05) | $pK_{L1}$ = 4.47 (±0.08)[a] |
| [Mn(H₂qtp2)] | 1 | 1 | −2 | −7.19 (±0.01) | |
| [Mn(H₃qtp2)]⁺ | 1 | 1 | −1 | −0.05 (±0.01) | $pK_a$(Mn(H₃qtp2)⁺) = 7.14 (±0.02)[b] |
| [Mn(H₄qtp2)]²⁺ | 1 | 1 | 0 | 5.77 (±0.01) | $pK_a$(Mn(H₄qtp2)²⁺) = 5.82 (±0.02)[c] |
| [Mn(H₅qtp2)]³⁺ | 1 | 1 | 1 | 11.30 (±0.01) | $pK_a$(Mn(H₅qtp2)³⁺) = 5.53 (±0.02)[d] |

Refer to Scheme 4 for the proposed molecular structures for each ligand and Mn(II) complex. Due to the instability of the ligand at high pH values, we were unable to obtain log(β) values for the H₃qtp2⁻ and H₂qtp2²⁻ species.
[a]Ligand $pK_a$ values corresponding to the (de)protonation of the free ligand amine and pyridine groups. $K_{L1}$ = [H₅qtp2⁺][H⁺]/[H₆qtp2²⁺], $pK_{L1}$ = logβ₀₁₁ − logβ₀₁₀. $K_{L2}$ = [H₄qtp2][H⁺]/[H₅qtp2⁺], $pK_{L2}$ = logβ₀₁₂ − logβ₀₁₁.
[b]$K_a$(Mn(H₃qtp2)⁺) = [Mn(H₂qtp2)][H⁺]/[Mn(H₃qtp2)⁺], corresponds to the (de)protonation of the second quinol. $pK_a$(Mn(H₃qtp2)⁺) = logβ₁₁₋₁ − logβ₁₁₋₂.
[c]$K_a$(Mn(H₄qtp2)²⁺) = [Mn(H₃qtp2)⁺][H⁺]/[Mn(H₄qtp2)²⁺], corresponds to the (de)protonation of a quinol group. $pK_a$(Mn(H₄qtp2)²⁺) = logβ₁₁₀ − logβ₁₁₋₁.
[d]$K_a$(Mn(H₅qtp2)³⁺) = [Mn(H₄qtp2)²⁺][H⁺]/[Mn(H₅qtp2)³⁺], corresponds to the (de)protonation of a pyridine group. $pK_a$(Mn(H₅qtp2)³⁺) = logβ₁₁₁ − logβ₁₁₀.

TABLE 6 pMn value and $pK_a$ Values for the Ligands and Mn(II) Complex Determined by Potentiometric Titration at 25° C.

| | |
|---|---|
| $pK_{L1}$[a] | 4.47 (±0.08) |
| $pK_{L2}$[a] | 7.18 (±0.03) |
| $pK_a$(Mn(H₅qtp2)³⁺)[b] | 5.53 (±0.02) |
| $pK_a$(Mn(H₄qtp2)²⁺)[c] | 5.82 (±0.02) |
| $pK_a$(Mn(H₃qtp2)⁺)[d] | 7.14 (±0.02) |
| pMn(pH 7.4)[e] | 5.36 (±0.02) |

Refer to Scheme 3 for proposed molecular structures.
[a]Ligand $pK_a$ values corresponding to the (de)protonation of the free ligand amine and pyridine groups. $K_{L1}$ = [H₅qtp2⁺][H⁺]/[H₆qtp2²⁺], $K_{L2}$ = [H₄qtp2][H⁺]/[H₅qtp2⁺].
[b]$K_a$(Mn(H₅qtp2)³⁺) = [Mn(H₄qtp2)²⁺][H⁺]/[Mn(H₅qtp2)³⁺], corresponds to the (de)protonation of a pyridine group.
[c]$K_a$(Mn(H₄qtp2)²⁺) = [Mn(H₃qtp2)⁺][H⁺]/[Mn(H₄qtp2)²⁺], corresponds to the (de)protonation of a quinol group.
[d]$K_a$(Mn(H₃qtp2)⁺) = [Mn(H₂qtp2)][H⁺]/[Mn(H₃qtp2)⁺], corresponds to the (de)protonation of the second quinol.
[e]pMn = −log[Mn(II)]$_{free}$ calculated for [3] = 1.0 mM, 298K, pH 7.4.

Stability of [Mn(H$_4$qtp2)Br$_2$] to Air and Adventitious Metal Ions

The stability of 3 to air and adventitious metal ions was assessed primarily by UV/vis spectroscopy. Upon solvation in aerated MeOH, the 302 nm feature corresponding to the quinol groups decreases in intensity by about 10% over 12 h, demonstrating that 3 is sufficiently air stable for most MRI studies (Figure S1), with less than a 5% error introduced over 4 h. Complex 3, however, is susceptible to metal exchange. When equimolar amounts of 3 and Fe(ClO$_4$)$_2$ are mixed in MeCN, 80% of the Mn(II) is replaced by Fe(II) by 3 h. Experiments monitored by NMR suggest that Zn(II) can also readily displace the Mn(II) from 3 (vide infra).

Reactivity with H$_2$O$_2$

Although complex 3 is reasonably stable to air and moisture, it reacts with H$_2$O$_2$ in a variety of solvents to yield a mixture of Mn(II) species in which either zero, one, or two of the quinol groups have been oxidized to para-quinones.

Figure 25:
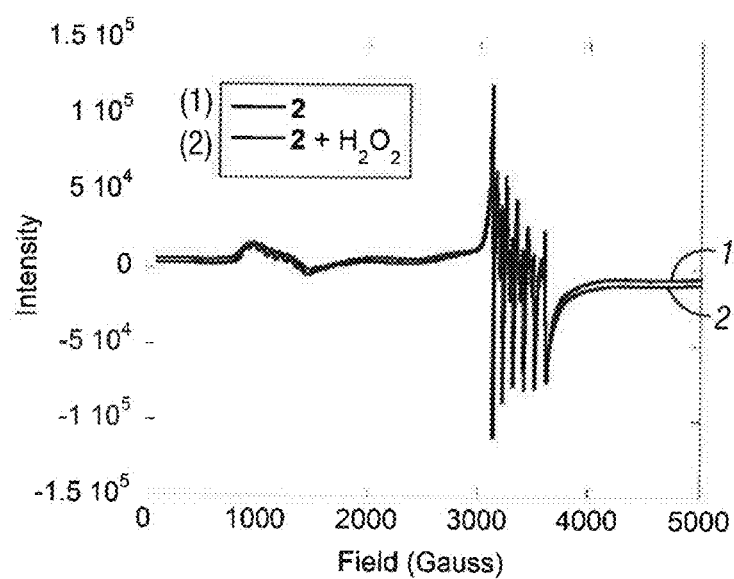
FIG. 25. X-band EPR spectra of 1.0 mM solutions of 3 in MeOH in the absence and presence of 10 mM $H_2O_2$.

EPR spectroscopy confirms that the manganese remains in the +2 oxidation state. The reaction between 3 and H$_2$O$_2$ proceeded for 30 min before the sample was frozen and analyzed. The data were acquired at 77 K. For both spectra: $g_{eff}$=2.00, A=103 Gauss. The EPR spectrum of a 1.0 mM solution of 3 in MeOH is highly similar to that corresponding to a 1.0 mM sample of 3 that was allowed to react with 10 mM of H$_2$O$_2$ for 30 min (FIG. 25). Both EPR spectra show a major feature at g=2.00 that is split six-fold by the I=5/2 manganese nucleus. A minor feature at 1000 gauss is present in both samples as well. For the non-oxidized sample, this feature likewise exhibits hyperfine splitting; the oxidized sample, conversely, lacks this detail. The two spectra overlap almost perfectly, suggesting that they have nearly equal concentrations of Mn(II).

Figure 26A:
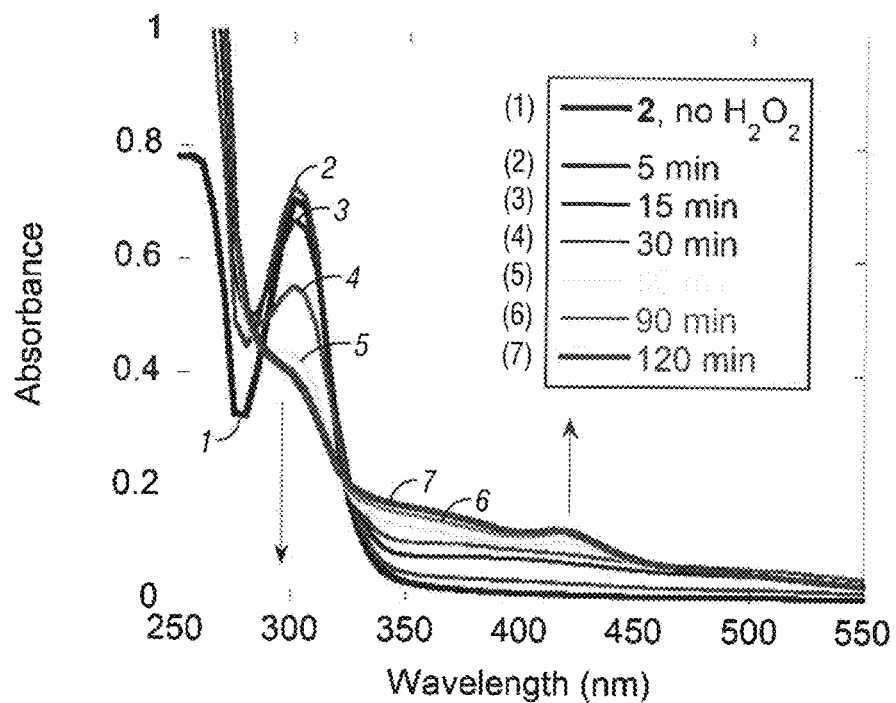
FIG. 26A. UV/vis spectra corresponding to the 298 K reaction between a 0.10 mM 3 and 10 mM $H_2O_2$ in MeOH.
Figure 26B:
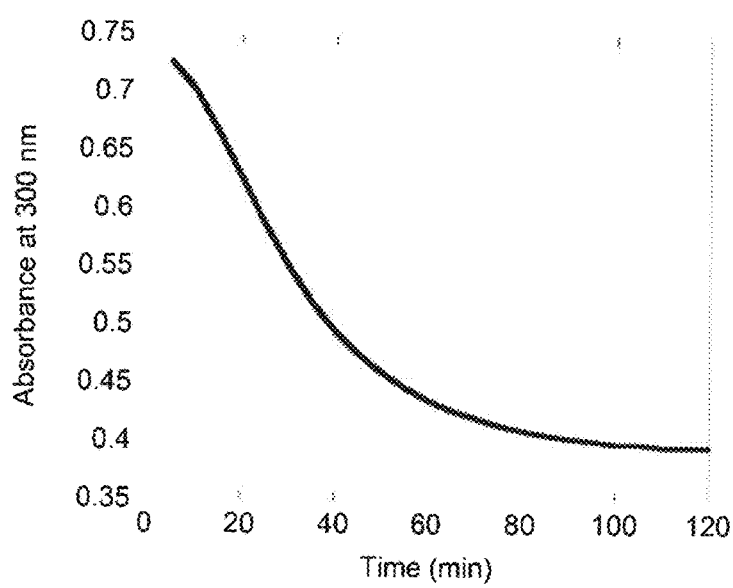
FIG. 26B shows the change in the absorbance at 300 nm over time upon mixing a 0.1 mM 3 and 10 mM $H_2O_2$ in MeOH.

UV/vis spectroscopy verifies that the reaction between 3 and H$_2$O$_2$ in MeOH oxidizes the quinols, as evidenced by the loss of the 302 nm band over 1 h (FIG. 26A). The reaction was tracked for 2 h. FIG. 26B shows the change in the absorbance at 300 nm over this time. The absorbance initially increases slightly due to the unreacted H$_2$O$_2$. The changes in the spectra are consistent with an induction period, in that little change occurs until approximately 10 min after the reagents are mixed. The loss of the 302 nm band can also be triggered by the addition of DDQ. Excesses of O$_2^-$ or ClO$^-$ result in the decomposition of the ligand and do not appear to cleanly generate species with either one or two para-quinones.

Figure 27:
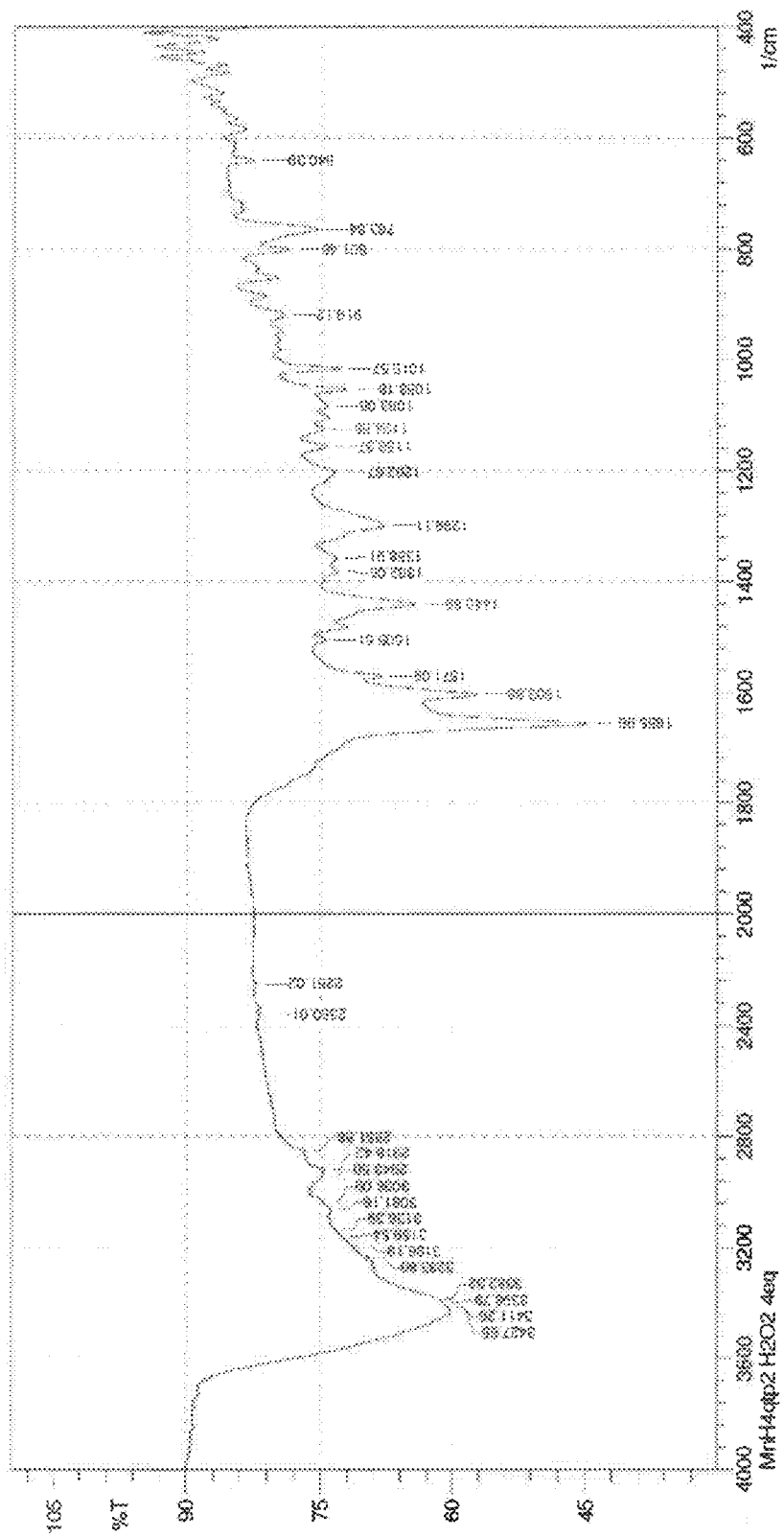
FIG. 27. IR spectrum of the crude product from the reaction between 1.0 mM 3 and 4.0 mM $H_2O_2$ in MeOH.

The IR of the solid isolated from reactions between 3 and 4 equiv. H$_2$O$_2$ in MeOH after 1 h reveals an intense band at 1659 cm$^{-1}$, which is typical of the carbonyl stretch associated with a non-metal-coordinated para-quinone (FIG. 27). For this analysis, after allowing 30 min to react, the solvents were stripped, yielding the solid used to prepare the sample (KBr). The peak at 1659 cm$^{-1}$ is assigned to a C=O stretch for the quinone groups formed upon the partial oxidation of the H$_4$qtp2 ligand. This compares well to the 1657 cm$^{-1}$ feature observed for 4. The intensity of the 3405 cm$^{-1}$ band, which can be at least partly attributed to O—H stretches from the quinol, decreases upon oxidation by H$_2$O$_2$, providing further evidence for the conversion of the quinols to para-quinones.

Mass spectrometry (MS) of reactions between 3 and H$_2$O$_2$ in either H$_2$O or MeOH detects m/z peaks at 485.20 and 483.19, corresponding to inorganic products with one and two para-quinones. As the amount of H$_2$O$_2$ is increased from 4 to 16 equiv., the reaction appears to proceed more quickly and forms more 4. Despite this, none of the reactions go to completion; the m/z peaks for 3 never fully disappear. Additional m/z peaks are found when the reaction is allowed to proceed for 12 h. These peaks have not been assigned to discrete species and likely result from subsequent oxidation of the ligand and manganese. Treating the H$_2$O$_2$-oxidized 3 with an equimolar amount of dithionite reduces the ligand back to the H$_4$qtp2 state, as assessed by MS. Similar reversibility in the ligand oxidation was observed for 1.

Figure 28:
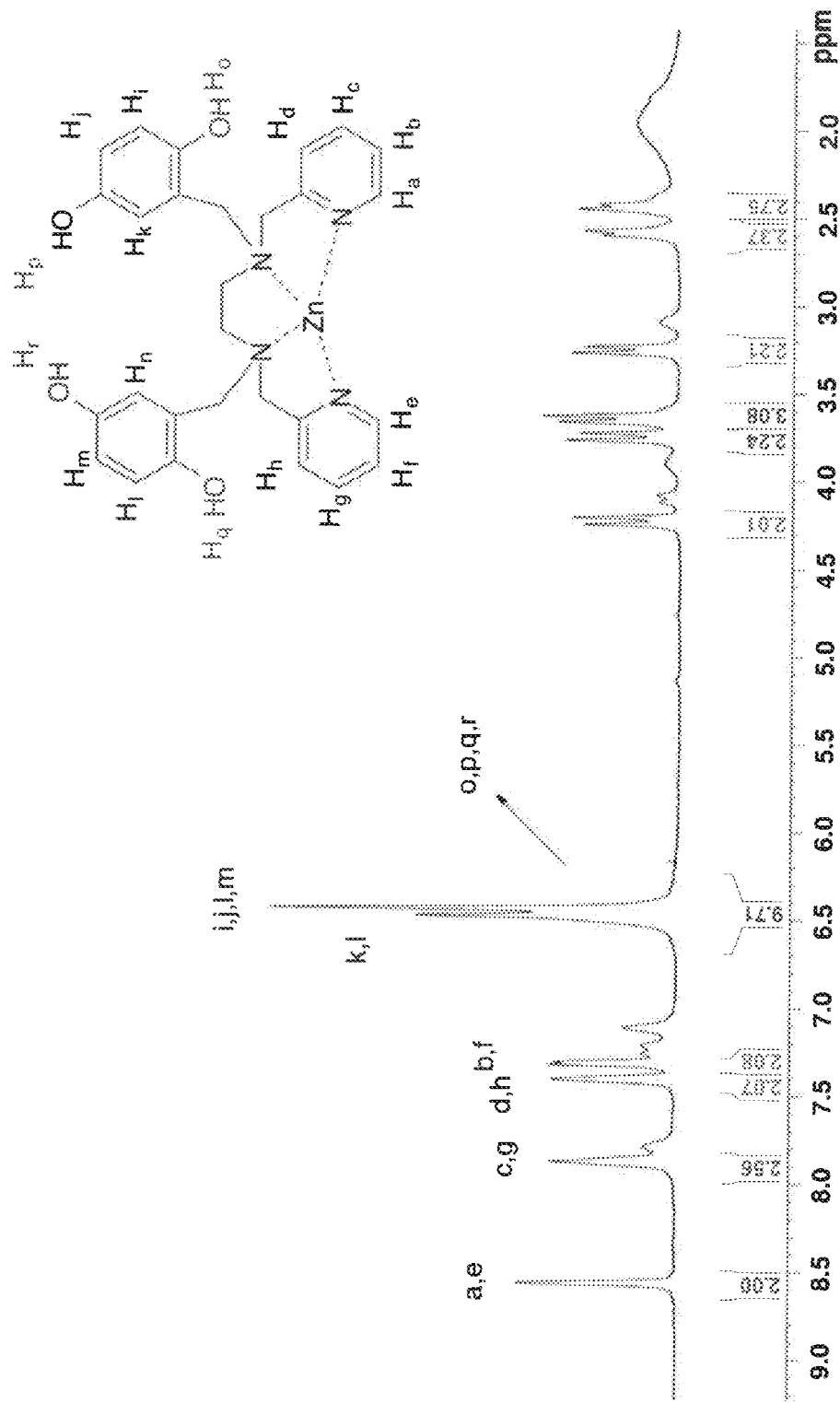
FIG. 28. $^1$H NMR spectrum of the diamagnetic product from the reaction between 10 mM 3 and 20 mM $Zn(ClO_4)_2$ in $CD_3CN$.
Figure 29:
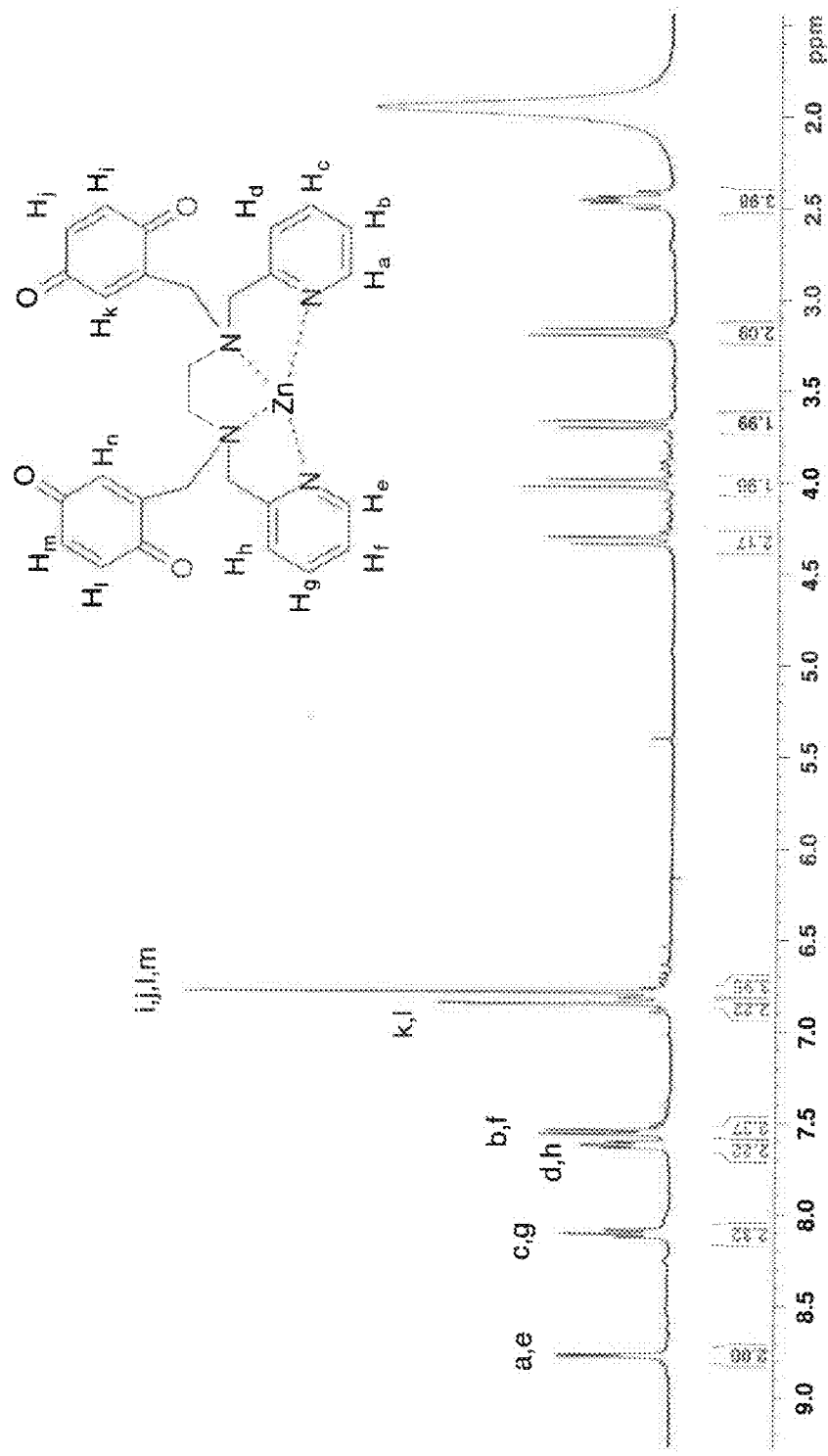
FIG. 29. $^1$H NMR spectrum of the diamagnetic product from the reaction between 10 mM 4 and 20 mM $Zn(ClO_4)_2$ in $CD_3CN$.

The changes to the H$_4$qtp2 ligand in 3 can be monitored and analyzed indirectly by $^1$H NMR. The addition of Zn(ClO$_4$)$_2$ to mixtures of 3 and its oxidized products in CD$_3$CN yields diamagnetic species that can be observed and quantitated by $^1$H NMR spectroscopy after the reaction was given 2 h to equilibrate. Mixing the Zn(II) salt and the 3 led to a 3:10 mixture of complexes (FIG. 28). The peaks observed between 7.0 and 8.8 ppm can be assigned to the protons on the pyridine subunits. The peaks around 6.5 ppm can be attributed to the O—H and C—H protons on the quinol subunits. These may either be conformers, solvent isomers, ionization isomers, or a combination thereof. The $^1$H NMR resonances corresponding to the quinolic C—H groups in the free ligand and Zn(II) complex are offset, but these changes aren't large enough to unambiguously confirm the coordination of the quinols to the Zn(II) in MeCN. The resonances corresponding to the quinolic C—H and O—H bonds overlap at 6.5 ppm in CD$_3$CN. The integration of this peak decreases by ~4 upon oxidation of 3 by DDQ; this is consistent with the oxidation of the two quinols to para-quinones that occurs upon the formation of 3 (FIG. 29). The decreased intensities of the peaks at ~6.8, relative to those in FIG. 28, correspond to a loss of 4H nuclei upon oxidation.

When 4 equiv. of H$_2$O$_2$ are added to a CD$_3$CN solution of 3 prior to treatment with Zn(II), only 50% of the quinols oxidize by 1 h, as assessed by the intensity of the feature at 6.5 ppm. Increasing the loading of oxidant to 8 equiv. maximizes the conversion to 70; raising the H$_2$O$_2$ loading to 16 equiv. does not further oxidize the quinols. Without the Zn(II), no ligand-derived resonances are observed, suggesting that the Mn(II) remains bound to the oxidized components in MeCN.

Measurement of Aliquot Group T$_1$ Relaxivity

The capability of 3 to serve as a MRI contrast agent was assessed with a 3 T clinical MRI scanner. All samples were run in 298 K aqueous solutions containing 50 mM HEPES buffered to pH 7.00, using a 3 T field provided by a clinical MRI scanner. All samples were prepared under air. The oxidized samples were prepared by directly adding H$_2$O$_2$ to solutions of 3 in aqueous solutions buffered to pH 7.0. The oxidation reactions were allowed to proceed for 30 min at 298 K before the T$_1$ measurements were taken. The data were fit to the indicated linear equations; the y-intercepts were within error of 1/T$_1$ measurements associated with two control samples that contained no Mn(II): pure water (0.39 s$^{-1}$) and 50 mM HEPES buffer (0.38 s$^{-1}$). A second series of measurements yielded r$_1$ values of 5.64 mM$^{-1}$ s$^{-1}$ and 7.32 mM$^{-1}$ s$^{-1}$ for 3 before and after reaction with H$_2$O$_2$.

Figure 30:
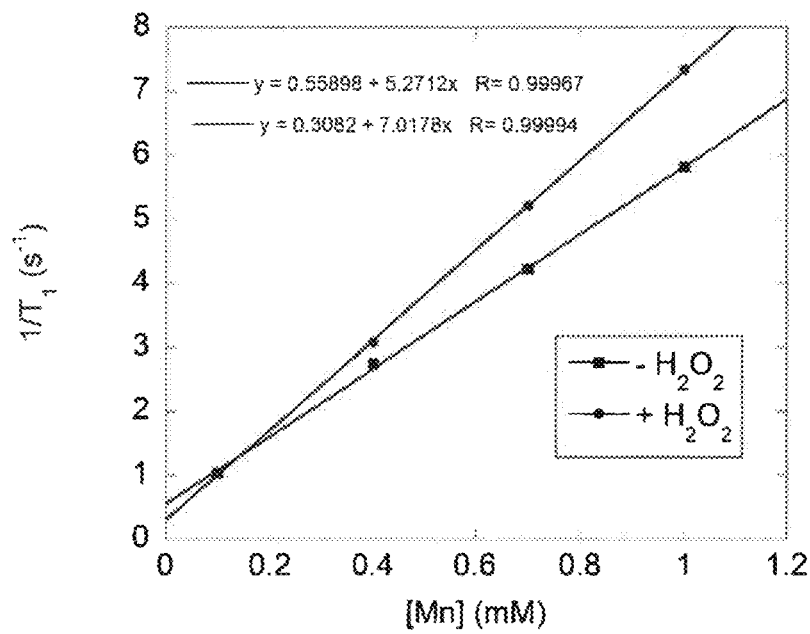
FIG. 30. Plots of $(1/T_1)$ versus Mn(II) concentration for 3 in the presence (blue) and absence (black) of 10 mM $H_2O_2$.

The relationship between the concentration of 3 in 50 mM HEPES buffer (pH 7.0, 25° C.) and T$_1$ was linear and consistent with the Mn(II) and H$_4$qtp2 remaining bound to each other in solution. The slopes of two separate series of experiments yield a r$_1$ of 5.46 (+0.19) mM$^{-1}$ s$^{-1}$. The r$_1$ of 3 increases to 7.17 (+0.15) mM$^{-1}$ s$^{-1}$ upon the addition of 10 mM of H$_2$O$_2$ to solutions of the Mn(II) complex in buffered water (FIG. 30). A large excess of H$_2$O$_2$ was added both to activate the sensor to as full an extent as possible and to enable direct comparisons to prior H$_2$O$_2$-sensitive MRI contrast agents reported by our lab. Despite the large excess of H$_2$O$_2$ present, the 1.71 mM$^{-1}$ s$^{-1}$ response corresponds to partial oxidation of 3 to species containing $H_2qtp2$ and qtp2. We attempted to measure $r_1$ for the isolated samples of the fully oxidized 4, but the poor solubility of this compound in water precluded these measurements.

Cytotoxicity

The toxicity of 3 was tested using H9c2 cells in order to facilitate comparison to that of 1. H9c2 cells were obtained from the American Tissue Type Collection (Manassas, Va., USA) and grown at 37° C. with 95% humidity and 5% $CO_2$. Cells were grown in Dulbecco's modified eagles medium (DMEM) supplemented with 10% fetal bovine serum. Experiments were performed at 70-80% confluence. To determine the cytotoxic effects of 3, H9c2 cells were exposed to increasing concentrations of 3 (0.1-1000 M) or its vehicle in DMEM for 4 or 24 hr. Cell number was assessed using the CyQUANT Cell Proliferation Assay Kit (Life Technologies Corporation, Carlsbad, Calif.) per manufacturer's instructions. Cell number was expressed as percentage of the vehicle-treated cells. Values are expressed as mean and standard deviation and represent 2-4 experiments performed in triplicate. The bars marked with an * display a significant difference from the vehicle-treated cell number for corresponding time period (p<0.05).

Figure 31:
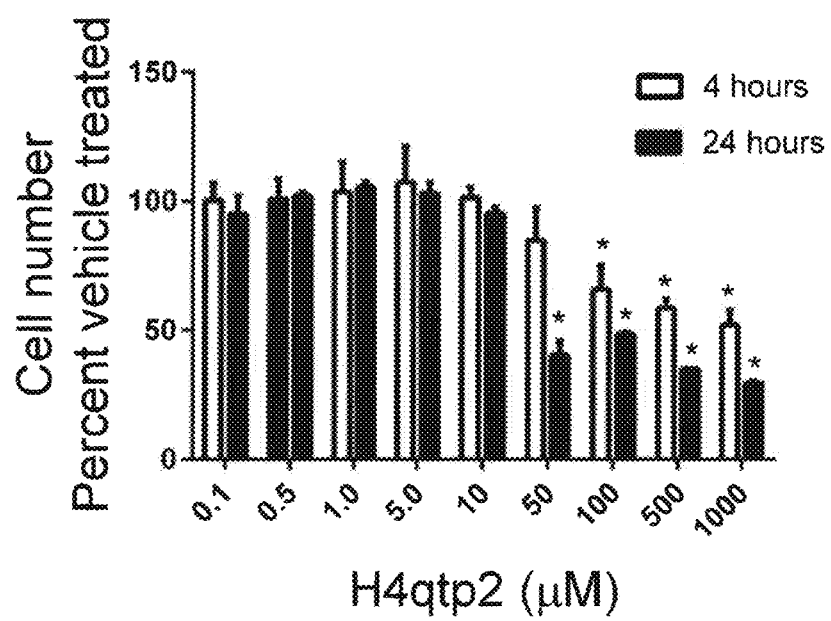
FIG. 31. Cytotoxicity of 3 towards H9c2 cells.

H9c2 cells could withstand 1.0 µM concentrations of 1 for at least 24 h. Upon increasing the dose to 10 µM, no cell death was observed at 4 h, but less than 50% survived by 24 h. Complex 3 is significantly less toxic. A 10 µM dose of 3 does not impact the viability of H9c2 cells over 24 h (FIG. 31). The viability of cells exposed to 50 µM of 3 is within error to that of the control at 4 h. Higher concentrations of 3 do trigger cell death, but markedly greater percentages of the cells survive for all analyzed dosages and exposure times than for 1. It should be noted that these cytotoxicities represent upper limits. A human or animal model would be expected to eliminate the probe, and the contact between individual cells and a freely diffusing sensor would not be anticipated to approach 4 h.

Anti-Oxidant Activity

Previously reported $H_2O_2$ sensors from our laboratory were found to behave as potent anti-oxidants. Complex 1 served as an excellent mimic of superoxide dismutase (SOD) and could donate hydrogen atoms more readily than ascorbic acid, as assessed by the 2,2-diphenyl-1-picryl-hydrazyl hydrate (DPPH) assay.

Figure 32:
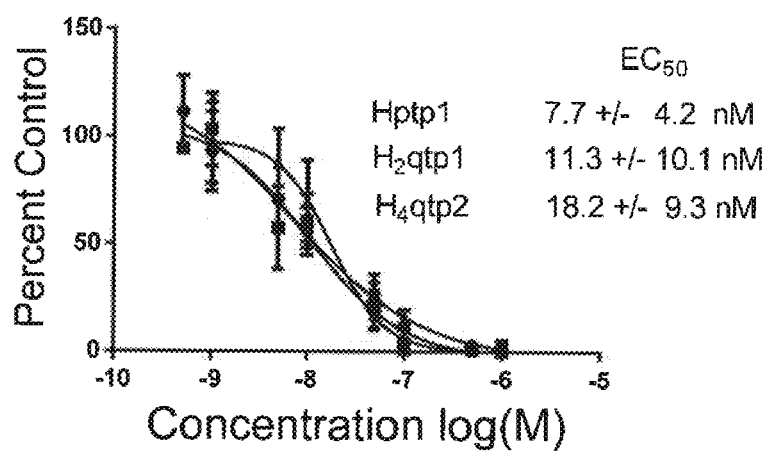
FIG. 32. Superoxide scavenging effects of 1, 3, and $[Mn(Hptp1)(MeCN)](ClO_4)_2$.

The ability of 3 to degrade superoxide was tested using a standard technique that uses the reaction between xanthine oxidase and xanthine to generate $O_2^-$ and a subsequent reaction with the chemiluminescent probe lucigenin to detect it. Reactions were carried out in 50 mM Tris-HCl (pH 8.0). Data for the various concentrations of Mn(II) complex are expressed as a percentage of luminescence in the presence of vehicle. As was found for 1 and 2, complex 3 successfully intercepts $O_2^-$ before its reaction with lucigenin (FIG. 32). The $EC_{50}$ value for 3 was found to be 18.2 nM, which is equal within error to that measured for 1.

Figure 33:
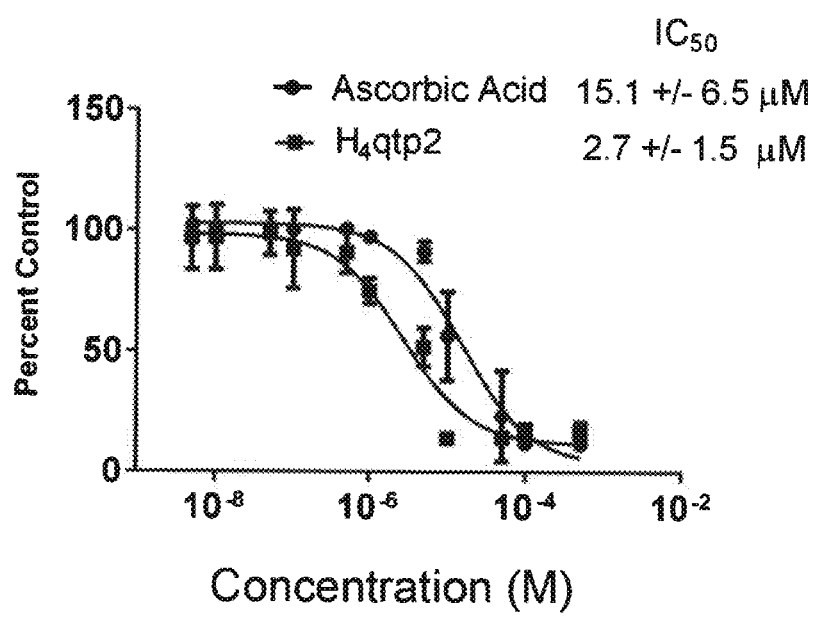
FIG. 33. DPPH free radical scavenging assay of 3 and ascorbic acid.

Complex 3 is also a competent oxidant as assessed by the DPPH assay (FIG. 33), which tests the abilities of compounds to donate hydrogen atoms to 2,2-diphenyl-1-picryl-hydrazyl radical hydrate. In this assay, the anti-oxidants were added to DPPH and incubated in the dark for 30 min at 298 K. Spectroscopic measurements were performed at 517 nm. The data were normalized to the absorbance in the presence of vehicle. All experiments were performed in triplicate and repeated twice. The hydrazine product is monitored by UV/vis. The $IC_{50}$ for 3 was found to be 2.7 µM; ascorbic acid was found to have an $IC_{50}$ value of 15 µM under the same conditions.

Much like $H_2qtp1$, the $H_4qtp2$ ligand binds Mn(II) readily in its neutral form. We were unable to obtain crystalline adducts with either $Mn(OTf)_2$ or $Mn(ClO_4)_2$, the former of which was used to prepare $[Mn(H_2qtp1)MeCN)](OTf)_2$ (1). The ligand was instead complexed to $MnBr_2$. The resultant $[Mn(H_4qtp2)Br_2]$ (3) features two Mn—Br bonds but no Mn—O bonds to the quinol subunits. The structure of 1, conversely, contains a Mn—O bond to the quinol group of the ligand. The difference in the structures can be rationalized by the much stronger metal-binding affinity of bromide ions relative to triflates. We do not believe that the structure in FIG. 17 is strictly maintained in aqueous solution since the complex between $H_4qtp2$ and Mn(II) appears to be stable at pH 7.0. The potentiometric pH titration data are consistent with the deprotonation and coordination of the quinol groups above pH 7. The $pK_a$ constants for the deprotonation of $[Mn(H_3qtp2)]^+$ (7.14) and $[Mn(H_4qtp2)]^{2+}$ (5.82) and the changes to the UV/vis spectra that occur upon lowering the pH (FIG. 3B) are consistent with observations previously made for other M(II)-bound phenols.

Although replacing a pyridine with a quinol could severely destabilize the Mn(II)-ligand complex in water or render it overly sensitive to $O_2$, we were gratified to find that neither event occurred. Complex 3 is moderately stable in aerobic aqueous solutions above pH 7.0 (FIG. 4). The ligand remains attached to the metal, as assessed by the lack of $^1H$ NMR resonances for solutions of 3 in $D_2O$, the UV/vis data evidence for metal-bound quinols, and the pMn of 5.36 calculated at pH 7.4. The stability can be attributed to the deprotonation of the quinols; the resultant anionic forms of the ligand will have a stronger affinity for Mn(II) than neutral $H_4qtp2$. Noticeable dissociation of the Mn(II) does occur below pH 7.0, and the improved stabilization of Mn(II) complexes with redox-active ligands remains an important goal for this project. Only slight ligand oxidation is observed upon 12 h of exposure to air. Complex 3 is much more susceptible to metal substitution than 1, and a 3 h treatment of a 0.10 mM solution of the Mn(II) complex with 0.10 mM $Fe(ClO_4)_2$ is sufficient to remove approximately 80% of the manganese (Figure S8). Biological concentrations of peptide-free transition metal ions are not anticipated to approach this level, however,[9] and metal displacement is therefore unlikely to significantly impact the ability of the probe to function in most biological environments.

The reaction between 3 and $H_2O_2$ oxidizes the ligand, rather than the metal, as assessed by EPR, IR, UV/vis, and NMR spectroscopies. Most of the analyses were performed in organic solvents to facilitate the characterization, but MS data affirm that the reaction occurs in water to yield the same para-quinone-containing products (Figure S12). $^1H$ NMR analysis of the product mixture does not detect any free ligand, suggesting that the Mn(II) complexes with the oxidized ligands are also water-stable. The lack of precipitation suggests that complex 4, which has two inner-sphere bromide ions, is not a major product of $H_2O_2$ oxidation in water. Fuller interrogation of the stability of complex 4 is complicated by the inability to generate it cleanly in water; complexes with $H_4qtp2$ and the mono-para-quinone ligand, $H_2qtp2$, are also present. Upon prolonged oxidation (3 h) a 420 nm band begins to appear in the UV/vis spectrum; this may be consistent with Mn(III) or Mn(IV). A similar feature was not observed for the monoquinol complex, suggesting that the metal center in 3 is more sensitive to over-oxidation by $H_2O_2$ than 1.

As was observed with complex 1, excess $H_2O_2$ only oxidizes about ~70% of the quinols of 3 to para-quinones. We speculate that secondary reactions between the oxidized probes and $H_2O_2$ or another ROS may reduce the probe back to 3, thereby limiting the maximum oxidation. This may be connected to the SOD activity, which is comparable to that of 1. The oxidation of the ligand can also be reversed with dithionite. The ability to reverse the oxidation of the probe is valuable since it may enable a freely diffusing sensor to identify regions of high oxidative activity. Under these circumstances, the probe could be deactivated by naturally occurring anti-oxidants upon exiting a region with high concentrations of ROS.

Complex 3 is an excellent MRI contrast agent, and the 5.46 (±0.19) $mM^{-1}s^{-1}$ $r_1$ value is high relative to clinically approved mononuclear Gd(III)- or Mn(II)-containing contrast agents. Higher $r_1$ values have been measured for mononuclear Mn(II) complexes, albeit under different conditions. At pH 7.0, the Mn(II) complexes with the structurally similar and hexadentate Hptp1 and $H_2$qtp1 ligands have $r_1$ values of 4.39 and 4.73 $mM^{-1}s^{-1}$. The Hptp1 complex was recently firmly established to be a q=1 species at pH 7.4, and its relatively high $r_1$ has been attributed to rapid inner-sphere water exchange. We believe that the higher $r_1$ values for the $H_2$qtp1 and $H_4$qtp2 complexes result from more extensive second-sphere interactions with water molecules, which have been found to markedly increase the relaxivities of Gd(III)-containing MRI contrast agents. The $r_1$ values for [Mn(Hptp1)(MeCN)]$^{2+}$, 1, and 3 scale with the number of hydroxyl groups on the ligand; each installed OH group increases $r_1$ by 0.36 $mM^{-1}$ $s^{-1}$. We currently speculate that the enhancement in $r_1$ is accomplished through proton exchange with bulk water and/or second-sphere interactions with water molecules. Hydrogen bonding between a phenolic O-donor and a second-sphere water molecule was observed in the crystal structure of [Mn(Hptp1)(MeCN)]$^{2+}$.

Upon exposure to $H_2O_2$, the relaxivity increases by 31%. To the best of our knowledge, 3 is the third MRI contrast agent with a direct turn-on $r_1$ response to $H_2O_2$. Other redox-responsive contrast agents either display a turn-off response or require a co-analyte. In 2013, Almutairi and co-workers reported coated $Gd_2O_3$ nanoparticles that exhibited a 10-fold increase in $r_1$ upon exposure to excess $H_2O_2$. Although the response is stronger, its irreversibility would prevent the sensors from tracking fluctuations in the concentration of $H_2O_2$.

Even though the oxidation of the ligand should render it a weaker chelate and likely triggers the release of free Mn(II), we do not believe that the entirety of the $r_1$ response can be attributed to release of the metal ion. We previously found that [Mn(H$_2$O)$_6$]$^{2+}$ has a $r_1$ value of about 5.3 $mM^{-1}s^{-1}$ under conditions that are identical to those used to characterize the relaxivity of 3 in the presence and absence of $H_2O_2$.[10] If the ligand oxidation were to merely release Mn(II), the relaxivity would remain approximately the same. The para-quinones in $H_2$qtp2 and qtp2 may coordinate to the metal to an extent; a prior study from our lab found that carbonyl groups from esters could bind to Mn(II) as parts of a polydentate ligand. Further, the remaining quinol in the partially oxidized $H_2$qtp2 would be anticipated to deprotonate and bind to the metal above pH 7.0.

One concern about introducing redox-active metals into a biological system is that they have the capacity to increase the concentrations of ROS through reactions with $O_2$. The $H_2$qtp1 complex 1 was instead found to be a strong anti-oxidant in that it can catalytically degrade superoxide and transfer hydrogen atoms to radical species. Despite the significant structural differences, compound 3 behaves similarly. The superoxide dismutase (SOD) activity is approximately equal to that for 1, and its $EC_{50}$ value, although an imperfect gauge, ranks 3 amongst the best small molecule SOD mimics. Much like 1, complex 3 has an electrochemical feature at about 300 mV vs. NHE, but this feature is much less reversible. A large concentration of $O_2$ will degrade 3, similar to what we found for 1. Although biological concentrations of $H_2O_2$ likely dwarf those of $O_2^-$, degradation of the probes by other ROS could become problematic in longer-term MRI studies.

The hydrogen atom donating ability of 3 was measured with the 2,2-diphenyl-1-picryl-hydrazyl hydrate (DPPH) assay. By this measure, the complex was found to be a superior anti-oxidant to ascorbic acid. Due to the sensitivity of the assay, direct comparison of 1 and 3 is difficult. Their reactivities relative to a common ascorbic acid standard suggest that their abilities to donate H atoms are approximately equivalent.

The addition of a second redox-active quinol to a previously reported MRI contrast agent sensor for $H_2O_2$ markedly increases its relaxivity response, albeit at the cost of some of the pre-activated complex's stability to adventitious transition metal ions and $O_2$. The fundamental reactivity with $H_2O_2$ appears to be the same for the Mn(II) complexes with the $H_2$qtp1 and $H_4$qtp2 ligands, in that the enhancement in $r_1$ is associated with the oxidation of the quinols to para-quinone groups. The second quinol increases the $r_1$ values of both the reduced and oxidized forms of the sensor, and the incorporation of these highly hydrogen-bonding groups appears to be a viable strategy for the production of higher-relaxivity mononuclear contrast agents. The ability to isolate an oxidized product [Mn(qtp2)Br$_2$] allows us to confirm some of the molecular changes associated with the activation of the sensor. The replacement of one of the pyridine rings with a second quinol provides the added benefit of reducing the cytotoxicity. The complex with the diquinol ligand displays anti-oxidant activity that strongly resembles that of the monoquinol complex.

In summary, MRI contrast agents that use a redox-active ligand to signal the presence of $H_2O_2$ are synthesized. Unlike a prior sensor, the ligands in the contrast agents are oxidized and the ligand oxidation is reversible, which may allow related sensors to distinguish highly oxidizing regions within biological samples. The ligand oxidation results in a more weakly coordinating ligand, and causes an increase in $r_1$ as a result from greater aquation of the metal ion. The results disclosed here demonstrate the feasibility of this strategy for $H_2O_2$ detection. Additionally, the disclosed complexes are potent anti-oxidants, as assessed by two common assays for such activity. These complexes may therefore be able to serve as theranostic agents, i.e., both MRI contrast and therapeutic agents, for oxidative stress.

The inventions being thus described, it will be obvious that the same may be varied in many ways. Such variations are not to be regarded as a departure from the spirit and scope of the inventions and all such modifications are intended to be included within the scope of the following claims.

The above specification provides a description of the synthesis and use of the disclosed compositions and methods. Since many embodiments can be made without departing from the spirit and scope of the invention, the invention resides in the claims.

What is claimed is:

1. A composition comprising a complex of a metal ion M with a ligand A, or salt thereof, wherein the complex has a generic formula, $$[M(A)(B)]^x$$

wherein M is $Mn^{2+}$, $Ni^{2+}$, $Co^{2+}$, $Fe^{2+}$, or a combination thereof;

B is absent, acetonitrile, methanol, $Cl^-$, $Br^-$, $I^-$, ethanol, water, perchlorate, triflate, a small inorganic or organic molecule or ion, mondentate, bidentate, or a combination thereof;

A is a ligand of formula II

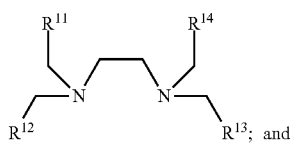

x is an integer between 6 and −6,

Wherein $R^{11}$, $R^{12}$, $R^{13}$, and $R^{14}$ are independently a substituted or unsubstituted pyridinyl, pyrazinyl, pyrimidinyl, pyridazinyl, 1,2,3-triazinyl, 1,2,4-trazinyl, 1,3,5-triazinyl, quinolyl, phenolyl group, or an isomer thereof, and at least one of $R^{11}$, $R^{12}$, $R^{13}$, and $R^{14}$ is a substituted or unsubstituted quinolyl group.

2. The composition of claim 1, wherein the $R^{11}$ and $R^{14}$ are independently a substituted or unsubstituted quinolyl group.

3. The composition of claim 1, wherein the ligand has a following formula

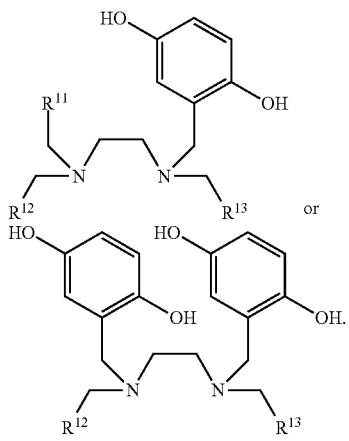

4. The composition of claim 1, wherein the ligand has a following formula

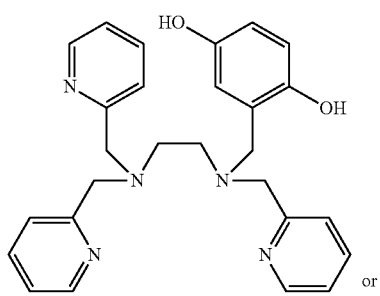

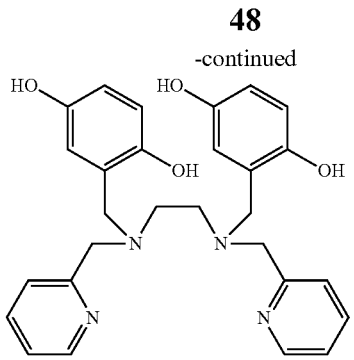

5. The composition of claim 1, wherein the metal ion is $Mn^{2+}$.

6. The composition of claim 1, wherein the ligand of the complex can be oxidized by a reactive oxygen species.

7. The composition of claim 6, wherein the reactive oxygen species is superoxide or $H_2O_2$.

8. The composition of claim 6, wherein the complex reacts with the reactive oxygen species without a co-analyte and does not display a response to molecular oxygen.

9. The composition of claim 1, wherein the complex has a log K of about 8-15.

10. The composition of claim 1, wherein the complex has a $T_1$-weighted relaxivity of about 3-8 $mM^{-1}s^{-1}$ before oxidation.

11. The composition of claim 6, wherein the complex increases its $T_1$-weighted relaxivity upon reacting with the reactive oxygen species.

12. The composition of claim 6, wherein the complex increases its $T_1$-weighted relaxivity upon reacting with the reactive oxygen species by more than 0.5 $mM^{-1}s^{-1}$.

13. The composition of claim 6, wherein the ligand is oxidized when the complex reacting with the reactive oxygen species.

14. The composition of claim 6, the complex does not change the metal ion's oxidation state upon reacting with the reactive oxygen species.

15. The composition of claim 6, wherein the complex's reaction with the reactive oxygen species is reversible.

16. The composition of claim 1, wherein the complex is $[Mn(H_2qtp1)(MeCN)]^{2+}$, wherein MeCN is acetonitrile and $H_2qtp1$ is

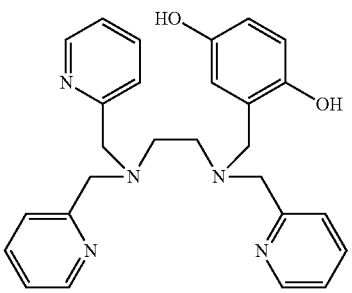 [SMILES: Oc1ccc(O)c(CN(CCN(Cc2ccccn2)Cc2ccccn2)Cc2ccccn2)c1]

or [Mn(H$_4$qtp2)Br$_2$], wherein H4qtp2 is

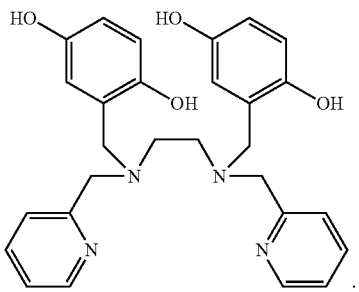 [SMILES: Oc1ccc(O)c(CN(CCN(Cc2ccccn2)Cc2cc(O)ccc2O)Cc2ccccn2)c1]

17. A contrast agent composition for magnetic resonance imaging comprising a metal complex of a following generic formula

[M(A)(B)]$^x$

M is Mn$^{2+}$, Ni$^{2+}$, Co$^{2+}$, Fe$^{2+}$, or a combination thereof;
B is absent, acetonitrile, methanol, Cl$^-$, Br$^-$, I$^-$, water, perchlorate, triflate, a small inorganic or organic molecule or ion, mondentate, didentate, or a combination thereof;
A is a ligand of formula II

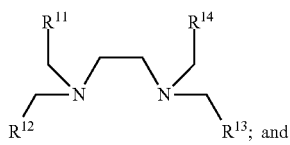

x is an integer between 6 and −6,
wherein R$^{11}$, R$^{12}$, R$^{13}$, and R$^{14}$ are independently a unsubstituted or substituted pyridinyl, pyrazinyl, pyrimidinyl, pyridazinyl, 1,2,3-triazinyl, 1,2,4-trazinyl, 1,3,5-triazinyl, quinolyl, phenolyl group, or an isomer thereof, at least one of R$^{11}$, R$^{12}$, R$^{13}$, and R$^{14}$ is a substituted or unsubstituted quinolyl group, and wherein the composition is a magnetic resonance imaging contrast agent for a reactive oxygen species within an subject, and the contrast agent reacts with a reactive oxygen species within an subject.

18. A method of detecting a reactive oxygen species hotspot in a subject comprising
providing a subject,
applying a contrast agent to the subject, and
performing magnetic resonance imaging on the subject after applying the contrast agent;
wherein the contrast agent comprises a metal complex with an organic ligand, the metal complex reacts with a reactive oxygen species, the organic ligand is oxidized, the metal ion does not change its oxidation state, the metal complex increases its T$_1$-weighted relaxivity, and the oxidation of the ligand is reversible wherein the metal complex has a generic formula [M(A)(B)]$^x$,
wherein M is Mn$^{2+}$, Ni$^{2+}$, Co$^{2+}$, Fe$^{2+}$, or a combination thereof;
B is absent, acetonitrile, methanol, Cl$^-$, Br$^-$, I$^-$, water, perchlorate, triflate, a small inorganic or organic molecule or ion, mondentate, bidentate, or a combination thereof;

A is a ligand of formula II

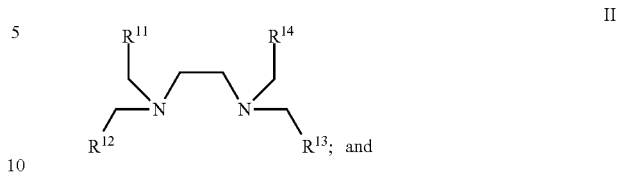

x is an integer between 6 and −6,
wherein R$^{11}$, R$^{12}$, R$^{13}$, and R$^{14}$ are independently a unsubstituted or substituted pyridinyl, pyrazinyl, pyrimidinyl, pyridazinyl, 1,2,3-triazinyl, 1,2,4-trazinyl, 1,3,5-triazinyl, quinolyl, phenolyl group, or an isomer thereof, at least one of R$^{11}$, R$^{12}$, R$^{13}$, and R$^{14}$ is a substituted or unsubstituted quinolyl group.

19. The method of claim 18, wherein the meta complex is [Mn(H$_2$qtp1)(MeCN)]$^{2+}$, wherein MeCN is acetonitrile and H$_2$qtp1 is

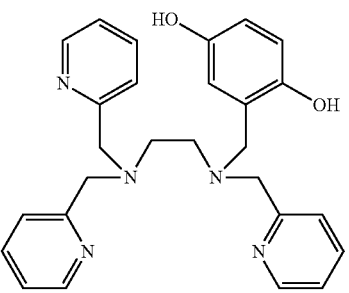 [SMILES: Oc1ccc(O)c(CN(CCN(Cc2ccccn2)Cc2ccccn2)Cc2ccccn2)c1]

or [Mn(H$_4$qtp2)Br$_2$], wherein H$_2$qtp2 is

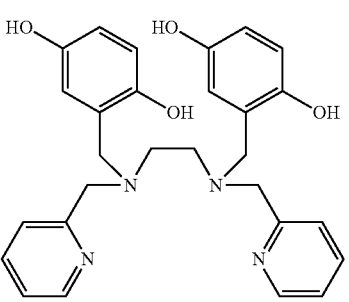

20. A pharmaceutical composition comprising a metal complex of a generic formula [M(A)(B)]$^x$, a stereoisomer thereof, a tautomer thereof, a tautomer of the stereoisomer, a pharmaceutically acceptable salt of any of the foregoing, as the active ingredient, and one or more pharmaceutically acceptable excipients,
wherein M is Mn$^{2+}$, Ni$^{2+}$, Co$^{2+}$, Fe$^{2+}$, or a combination thereof;
B is absent, acetonitrile, methanol, Cl$^-$, Br$^-$, I$^-$, water, perchlorate, triflate, a small inorganic or organic molecule or ion, monodentate, didentate, or a combination thereof;

A is a ligand of formula II

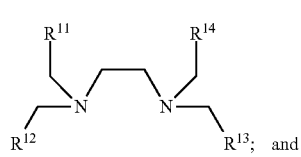

x is an integer between 6 and −6,
wherein $R^{11}$, $R^{12}$, $R^{13}$, and $R^{14}$ are independently a unsubstituted or substituted pyridinyl, pyrazinyl, pyrimidinyl, pyridazinyl, 1,2,3-triazinyl, 1,2,4-trazinyl, 1,3,5-triazinyl, quinolyl, phenolyl group, or an isomer thereof, at least one of $R^{11}$, $R^{12}$, $R^{13}$, and $R^{14}$ is a substituted or unsubstituted quinolyl group, and wherein the composition is a magnetic resonance imaging contrast agent composition and reduces reactive oxygen species in a subject or relieve oxidative stress of a subject.

* * * * *

UNITED STATES PATENT AND TRADEMARK OFFICE
CERTIFICATE OF CORRECTION

Page 1 of 2

PATENT NO. : 10,233,205 B2
APPLICATION NO. : 15/230030
DATED : March 19, 2019
INVENTOR(S) : Christian R. Goldsmith et al.

It is certified that error appears in the above-identified patent and that said Letters Patent is hereby corrected as shown below:

In the Specification

In Column 1, Line 15:
INSERT Heading and Paragraph before the Heading "FIELD OF THE INVENTION" as follows:
--GRANT REFERENCE
This invention was made with government support under EPS1158862 awarded by the National Science Foundation. The government has certain rights in the invention.--

In the Claims

In Column 47, Claim 1, Lines 11 and 17:
DELETE the Roman Numeral "II" above and to the right of the formula in Line 11
INSERT the Roman Numeral --II-- below and centered of the formula in Line 17

In Column 49, Claim 16, Line 1:
DELETE "H4qtp2" after the word wherein
INSERT --$H_4qtp2$-- after the word wherein In Column 49, Claim 17, Lines 30 and 36:
DELETE the Roman Numeral "II" above and to the right of the formula in Line 30
INSERT the Roman Numeral --II-- below and centered of the formula in Line 36

In Column 50, Claim 18, Lines 4 and 10:
DELETE the Roman Numeral "II" above and to the right of the formula in Line 4
INSERT the Roman Numeral --II-- below and centered of the formula in Line 10

In Column 50, Claim 19, Lines 20 and 22:
DELETE the word "meta" before the word complex in Line 20
INSERT the word --metal-- before the word complex in Line 20

Signed and Sealed this
Twenty-eighth Day of May, 2019

Andrei Iancu
*Director of the United States Patent and Trademark Office*

DELETE "h₂qtpl" after the word and in Line 22
INSERT --$H_4qtp2$-- after the word wherein in Line 22

<u>In Column 51, Claim 20, Lines 4 and 10:</u>
DELETE the Roman Numeral "II" above and to the right of the formula in Line 4
INSERT the Roman Numeral --II-- below and centered of the formula in Line 10